US008591898B2

(12) United States Patent
Mills et al.

(10) Patent No.: US 8,591,898 B2
(45) Date of Patent: Nov. 26, 2013

(54) TREATMENT OF INTERSTITIAL CYSTITIS

(75) Inventors: Ian William Mills, Sandwich (GB); Stephen Charles Phillips, Sandwich (GB); Arnon Rosenthal, Woodside, CA (US); David Peter Scholfield, Sandwich (GB); David Louis Shelton, Oakland, CA (US)

(73) Assignee: Pfizer Limited, Sandwich, Kent (GB)

( * ) Notice: Subject to any disclaimer, the term of this patent is extended or adjusted under 35 U.S.C. 154(b) by 266 days.

(21) Appl. No.: 12/747,262

(22) PCT Filed: Dec. 17, 2008

(86) PCT No.: PCT/IB2008/055383
§ 371 (c)(1),
(2), (4) Date: Jun. 10, 2010

(87) PCT Pub. No.: WO2009/077993
PCT Pub. Date: Jun. 25, 2009

(65) Prior Publication Data
US 2010/0260775 A1  Oct. 14, 2010

Related U.S. Application Data

(60) Provisional application No. 61/014,171, filed on Dec. 17, 2007, provisional application No. 61/061,149, filed on Jun. 13, 2008.

(51) Int. Cl.
*A61K 39/395* (2006.01)
*C07K 16/22* (2006.01)

(52) U.S. Cl.
USPC .............. 424/145.1; 424/130.1; 424/133.1; 424/141.1; 530/387.1; 530/387.3; 530/388.23

(58) Field of Classification Search
None
See application file for complete search history.

(56) References Cited

U.S. PATENT DOCUMENTS

| | | | |
|---|---|---|---|
| 5,503,986 A | 4/1996 | Steers et al. | |
| 6,008,003 A | 12/1999 | Haak-Frendscho et al. | |
| 7,252,822 B2 * | 8/2007 | Shelton et al. | 424/145.1 |
| 2003/0096753 A1 | 5/2003 | Robertson et al. | |
| 2003/0108597 A1 | 6/2003 | Chancellor et al. | |
| 2004/0121959 A1 | 6/2004 | Boone et al. | |
| 2004/0131615 A1 | 7/2004 | Shelton et al. | |
| 2004/0219144 A1 | 11/2004 | Shelton et al. | |
| 2005/0074821 A1 | 4/2005 | Wild, Jr. et al. | |
| 2006/0147932 A1 | 7/2006 | Davies et al. | |

FOREIGN PATENT DOCUMENTS

| | | |
|---|---|---|
| WO | WO 2004032870 | 4/2004 |
| WO | WO 2004058184 | 7/2004 |
| WO | WO 2006065234 | 6/2006 |
| WO | WO 2006131951 | 12/2006 |

OTHER PUBLICATIONS

Rudikoff et al. (1982). Single amino acid substitution altering antigen-binding specificity. Proc. Natl. Acad. Sci. USA. 79:1979-1983.*
Dimitrakov et al, Journal of Urology, vol. 171, No. 4 Supplement, 2004, p. 95.
Hefti et al., Trends in Pharmacological Sciences, vol. 27, No. 2, 2006, pp. 85-91.
Lowe et al., British Journal of Urology, vol. 79, No. 4, 1997, pp. 572-577.
Miller et al., Urology, vol. 59, No. 4, 2002, pp. 603-608.
Sevcik et al., Pain, vol. 115, No. 1-2, 2005, pp. 128-141.
Shelton et al., Pain, vol. 116, No. 1-2, 2005, pp. 8-16.
International Search Report, PCT/IB2008/055383, mailed Jun. 15, 2009.
Wakabayashi, et al., "Low-affinity nerve growth factor receptor immunoreactivity in the human urinary bladder," *Neuroscience letters*, 1995, 9-12, vol. 186, No. 1.
Dmitrieva, et al., "The role of nerve growth factor in a model of visceral inflammation," *Neuroscience*, 1997, 449-459, vol. 78, No. 2.
Faydaci, et al., "Role of nerve growth factor receptor on bladder outlet obstruction," Turk Uroloji Dergisi (Turkish Journal of Urology), 2004, 72-79. Abstract.
Goins, et al., "Herpes simplex virus mediated nerve growth factor expression in bladder and afferent neurons: potential treatment for diabetic bladder dysfunction," J. Urol., 2001, 1748-1754, vol. 165, No. 5.
Guerios, et al., "Nerve growth factor mediates peripheral mechanical hypersensitivity that accompanies experimental cystitis in mice," Neurosci. Lett., 2006, 193-197, vol. 392, No. 3.
Jaggar, et al., "Inflammation of the rat urinary bladder is associated with a referred thermal hyperalgesia which is nerve growth factor dependent," *Br. J. Anaesth.*, 1999, 442-448, vol. 83, No. 3.
Lipps, "Isolation of nerve growth factor (NGF) from human body fluids; saliva, serum and urine: comparison between cobra venom and cobra serum NGF," *J. Nat. Toxins*, 2000, 349-356, vol. 9, No. 4. Abstract.
Lowe, et al., "Increased nerve growth factor levels in the urinary bladder of women with idiopathic sensory urgency and interstitial cystitis," British journal of urology, 1997, 572-577, vol. 79, No. 4. Abstract.
Marchand, et al., "Increased NGF and TrkA Expression in Bladder Biopsies from Interstitial Cystitis Patients," Anesthesiology Abstracts of Scientific Papers Annual Meeting, 2003, No. 2003, p. Abstract No. A-1011.
Sato et al., "The Role of Urinary Bladder Nerve Growth Factor in Reconstruction of Micturition Function in Streptozotocin-Induced Diabetes and Physiological Polyuria," Journal of Nihon University Medical Association, 2002, 447-455, vol. 61, No. 12. Abstract.

(Continued)

*Primary Examiner* — Christine J Saoud
*Assistant Examiner* — Jon M Lockard
(74) *Attorney, Agent, or Firm* — Pfizer Inc.

(57) ABSTRACT

The present invention relates to the use of an anti-NGF antibody in the treatment or prevention of pain and/or a lower urinary tract symptom (LUTS) associated with interstitial cystitis and/or painful bladder syndrome and/or bladder pain syndrome.

7 Claims, No Drawings

(56) References Cited

OTHER PUBLICATIONS

Seki, et al., "Suppression of nerve growth factor (NGF) in bladder afferent pathways reduces detrusor hyperreflexia in spinal cord injured rats," American Urological Association Annual Meeting, May 25-30, 2002, Orlando, FL, Moderated Poster.

Seki, et al., "Immunoneutralization of nerve growth factor in lumbosacral spinal cord reduces bladder hyperreflexia in spinal cord injured rats," J. Urol., 2002, 2269-2274, vol. 168, No. 5.

Seki, et al., "Suppression of Detrusor-Sphincter Dyssynergia by Immunoneutralization of Nerve Growth Factor in Lumbosacral Spinal Cord in Spinal Cord Injured Rats.," J. Urol., 2004, 478-482, vol. 171, No. 1.

Steers, et al., "Mechanisms of disease: the role of nerve growth factor in the pathophysiology of bladder disorders," Nature Clinical Practice Urology, 2006, 101-110, vol. 3, No. 2.

Teng, et al., "Progesterone induces the proliferation of urothelial cells in an epidermal growth factor dependent manner," J. Urol., 2003, 2014-2018, vol. 170, No. 5.

Tyagi, et al., "Intravesical administration of antisense peptide nucleic acid down regulates urothelial NGF expression in rat model of cystitis," Conference Abstract for American Urological Association Annual Meeting, San Antonio, Texas, USA, May 21-26, 2005.

Vaidyanathan, et al., "p75 nerve growth factor receptor in the vesical urothelium of patients with neuropathic bladder: an immunohistochemical study," Spinal Cord, 1998, 541-547, vol. 36, No. 8. Abstract.

Wolf-Johnston, et al., "Increased NGF and TRPV1 expression in urinary bladder and sensory neurons from cats with feline interstitial cystitis," Society for Neuroscience Abstract Viewer and Itinerary Planner, 2003, vol. 2003, Abstract No. 608.4.

Chen, et al., "Treatment of Lower Urinary Tract Symptoms and Overactive Bladder—Focus on Bladder Sensory Innervation," *Tzu Chi Med J*, 2006, 333, vol. 18, No. 5.

* cited by examiner

TREATMENT OF INTERSTITIAL CYSTITIS

This application is a national stage filing of PCT/IB2008/055383 filed Dec. 17, 2008, which claims the benefit of Provisional Patent Application No. 61/061,149 filed Jun. 13, 2008, and the benefit of Provisional Patent Application No. 61/014,171 filed Dec. 17, 2007.

FIELD OF THE INVENTION

The present invention relates to the use of an anti-NGF antibody in the treatment or prevention of pain and/or a lower urinary tract symptom (LUTS) associated with interstitial cystitis and/or painful bladder syndrome and/or bladder pain syndrome.

BACKGROUND OF THE INVENTION

Interstitial cystitis (IC) is a chronic bladder disease, of unknown origin, characterized by symptoms of pain, such as pelvic pain, and lower urinary tract symptoms (LUTS) such as increased urinary frequency/urgency. More recently terminology has evolved to include painful bladder syndrome (PBS) (MacDiarmid S A et al. Rev Urol 2007; 9(1): 9-16) or bladder pain syndrome (BPS) (van der Merve et al. European Urology 53(2008) 60-67, along with IC, that is IC/PBS/BPS to collectively describe this symptom complex.

Prevalence rates of IC/PBS/BPS vary from 67 to 230 per 100,000 women having clinically confirmed disease, although the number is likely higher than this due to under- or mis-diagnosis, commonly as endometriosis, recurrent urinary tract infection, overactive bladder or vulvodynia (Forrest J B et al. Clinical Courier 2006; 24(3): 1-8). IC has a significant impact on quality of life, affecting travel, family relationships, and employment (Slade D et al. Urol 1997; 49 (5A Suppl): 10-3), as well as being associated with depressive symptoms (Rothrock N E et al. J Urol 2002; 167: 1763-1767).

There are few well performed, placebo-controlled, randomized trials of therapies aimed at IC, and treatment often consists of a multimodal trial-and-error approach, as evidenced by one review of patients in the Interstitial Cystitis Data Base study which reported 183 different types of treatment (Rovner E et al. J Urol 2000; 56: 940-5).

No single etiology has been identified, and it is most likely a multifactorial process with several urologic insults causing a self-perpetuating process of epithelial cell dysfunction, C-nerve fibre activation, and proliferation of mast cells, leading to worsening tissue damage, scarring and fibrosis. The repetitive stimulation of C fibres from inflammation, and upregulation of sensory nerves in the bladder, ultimately leads to permanent alterations (centralization) resulting in hyperalgesia, chronic bladder pain and voiding dysfunction (Forrest J B et al. Clinical Courier 2006; 24(3):1-8).

Although no consensus has been reached on the fundamental causes of IC, existing data have led to speculation that three pathophysiologic mechanisms may be implicated: epithelial dysfunction, mast cell activation, and neurogenic inflammation (Nazif O et al. Urol 2007; 69 (Suppl 4A): 24-33).

There is a continuing need to provide a novel, effective treatment for pain and/or a lower urinary tract symptom of interstitial cystitis and/or painful bladder syndrome and/or bladder pain syndrome without the adverse effects or limited efficacy of currently available therapies.

There has been a report that a recombinant human anti-NGF (nerve growth factor) antibody has been tested in patients with interstitial cystitis (Dimitrakov, et al., J. Urology. Vol 171(4), Supplement, 363 (2004)). Although the objective of the study was to evaluate the efficacy and safety "in a group of IC patients with significant nerve damage and neuropathic pain component who have failed numerous previous treatments", only effects on nerve damage were reported using urinary nerve damage marker levels. It is important to note that no efficacy is reported in treating pain and/or a lower urinary tract symptom of the condition.

The anti-NGF antibody E3 has previously been reported as being useful in the treatment of pain, including rheumatoid arthritis pain, osteoarthritis pain and post-surgical pain (see for example WO2004/058184). However, given the etiology of interstitial cystitis and poor mechanistic understanding of the condition, it cannot be easily predicted that an anti-NGF antibody, such as antibody E3, could be used for treating pain and/or a lower urinary tract symptom (LUTS) associated with interstitial cystitis and/or painful bladder syndrome and/or bladder pain syndrome.

BRIEF SUMMARY OF THE INVENTION

In an aspect of the invention there is provided a method for treating or preventing pain and/or a lower urinary tract symptom (LUTS) associated with interstitial cystitis and/or painful bladder syndrome and/or bladder pain syndrome, comprising administering an effective amount of an anti-NGF antagonist antibody. In one embodiment, the antibody:

(a) binds NGF with a $K_D$ of less than about 2 nM;

(b) inhibits human NGF-dependent survival of mouse E13.5 trigeminal neurons with an IC50 of about 100 pM or less, wherein the IC50 is measured in the presence of about 15 pM human NGF; and/or (c) inhibits human NGF-dependent survival of mouse E13.5 trigeminal neurons with an IC50 of about 10 pM or less, wherein the IC50 is measured in the presence of about 1.5 pM of NGF.

Pain associated with interstitial cystitis and/or painful bladder syndrome and/or bladder pain syndrome comprise lower abdominal (pelvic) pain; bladder pain; suprapubic pain; vaginal pain; pain in the penis, testicles, scrotum and perineum; urethral pain; dyspareneuria; pain, pressure or discomfort that may increase as the bladder fills.

Lower urinary tract symptoms comprise three groups of urinary symptoms, which may be defined as storage (irritative), voiding (obstructive) and post-micturition symptoms. Storage symptoms comprise urgency, frequency, nocturia, urgency incontinence and stress incontinence, which can be associated with overactive bladder (OAB) and benign prostatic hyperplasia (BPH). Voiding symptoms comprise hesitancy, poor flow, intermittency, straining and dysuria. Post-micturition symptoms comprise terminal dribbling, post-void dribbling and a sense of incomplete emptying.

Over Active Bladder (OAB) is defined as urgency, with or without urge incontinence, usually with frequency and nocturia [Abrams et al., Neurourology and Urodynamics 21:167-178 (2002)]. Prevalence of OAB in men and women is similar, with approximately 16% of the population of the USA suffering from the condition [Stewart et al, Prevalence of Overactive Bladder in the United States: Results from the NOBLE Program; Abstract Presented at the $2^{nd}$ International Consultation on Incontinence, July 2001, Paris, France].

The terms OAB Wet and OAB Dry describe OAB patients with or without urinary incontinence respectively. Previously, the cardinal symptom of OAB was believed to be urinary incontinence. However, with the advent of the new terms this is clearly not meaningful for the large number of sufferers who are not incontinent (i.e. OAB Dry patients). Thus, a 2001 study from Liberman et al ['Health Related Quality of Life Among Adults with Symptoms of Overactive Bladder: Results From A US Community-Based Survey'; Urology 57(6), 1044-1050, 2001] examined the impact of all OAB symptoms on the quality of life of a community-based sample of the US population. This study demonstrated that individuals suffering from OAB without any demonstrable loss of urine have an impaired quality of life when compared with controls.

BPH is a chronically progressive disease that can lead to complications such as acute urinary retention, recurrent urinary tract infections, bladder stones and renal dysfunction. The prevalence and average severity of LUTS associated with BPH in men increases with age.

BPH leads to an increase in prostate volume, creating urethral and bladder outflow obstruction as well as secondary changes in bladder function. The effects of this are manifested by both storage (irritative) and voiding (obstructive) symptoms.

It has been shown in accordance with the invention that an anti-NGF antagonist antibody is capable of inhibiting or blocking pain and/or a lower urinary tract symptom (LUTS) associated with interstitial cystitis and/or painful bladder syndrome and/or bladder pain syndrome. In some embodiments, the pain and/or lower urinary tract symptom is/are alleviated within about 24 hours after administering the anti-NGF antagonist antibody. In some embodiments, the pain and/or lower urinary tract symptom is/are alleviated within about 4 days after administering the anti-NGF antagonist antibody. In some embodiments, the pain and/or lower urinary tract symptom is/are alleviated before observing or in the absence of an indication of improvement of the condition in the individual.

In a further aspect of the invention there is provided a method for treating or preventing pain and/or a lower urinary tract symptom (LUTS) associated with interstitial cystitis and/or painful bladder syndrome and/or bladder pain syndrome, comprising administering an effective amount of an anti-NGF antagonist antibody comprising a heavy chain variable region comprising:
 (a) a CDR1 region shown in SEQ ID NO: 3;
 (b) a CDR2 region shown in SEQ ID NO:4; and
 (c) a CDR3 region shown in SEQ ID NO:5.

In a further aspect of the invention there is provided a method for treating or preventing pain and/or a lower urinary tract symptom (LUTS) associated with interstitial cystitis and/or painful bladder syndrome and/or bladder pain syndrome, comprising administering an effective amount of an anti-NGF antagonist antibody comprising a light chain variable region comprising:
 (a) a CDR1 region shown in SEQ ID NO: 6;
 (b) a CDR2 region shown in SEQ ID NO:7; and
 (c) a CDR3 region shown in SEQ ID NO:8.

The anti-NGF antagonist antibody may further comprise a heavy chain variable region comprising:
 (a) a CDR1 region shown in SEQ ID NO: 3;
 (b) a CDR2 region shown in SEQ ID NO:4; and
 (c) a CDR3 region shown in SEQ ID NO:5.

The anti-NGF antagonist antibody may comprise a heavy chain variable region comprising an amino acid sequence at least 80%, 85%, 90%, 91%, 92%, 93%, 94%, 95%, 96%, 97%, 98% or 99% identical to the amino acid sequence of SEQ ID No. 1 and a light chain variable region comprising an amino acid sequence at least 80%, 85%, 90%, 91%, 92%, 93%, 94%, 95%, 96%, 97%, 98% or 99% identical to the amino acid sequence of SEQ ID No. 2, wherein the antibody binds specifically to NGF.

The heavy chain variable region and/or light chain variable region of the anti-NGF antibody may comprise one or more respective framework mutations. In one aspect the framework mutation may replace a human framework residue with the complementary murine framework residue. The mutation may comprise the substitution V71K in the heavy chain variable region.

The anti-NGF antagonist antibody may comprise a heavy chain variable region comprising the amino acid sequence of SEQ ID NO: 1 and/or may comprise a light chain variable region comprising the amino acid sequence of SEQ ID NO: 2.

The anti-NGF antagonist antibody may be an antibody comprising the amino acid sequences shown in SEQ ID NOS: 1 and 2. The anti-NGF antagonist antibody may be an antibody comprising the amino acid sequences shown in SEQ ID NOS: 16 and 17.

The anti-NGF antagonist antibody may comprise a heavy chain comprising an amino acid sequence at least 80%, 85%, 90%, 91%, 92%, 93%, 94%, 95%, 96%, 97%, 98% or 99% identical to the amino acid sequence of SEQ ID No. 16 and a light chain comprising an amino acid sequence at least 80%, 85%, 90%, 91%, 92%, 93%, 94%, 95%, 96%, 97%, 98% or 99% identical to the amino acid sequence of SEQ ID No. 17, wherein the antibody binds specifically to NGF.

The anti-NGF antagonist antibody may compete for NGF binding with an anti-NGF antagonist antibody as defined herein. The anti-NGF antagonist antibody may compete for NGF binding with an antibody comprising a heavy chain variable region comprising the amino acid sequence of SEQ ID NO: 1 and a light chain variable region comprising the amino acid sequence of SEQ ID NO: 2.

The anti-NGF antagonist antibody may be a humanized. The antibody may be antibody E3, which specifically binds human and rodent NGF. Antibody E3 is described in WO2004/058184, the content of which is hereby incorporated by reference in its entirety. The amino acid sequences of the heavy chain and light chain variable regions of E3 are shown in SEQ ID Nos. 1 and 2 (FIGS. 1A and 1B of WO2004/058184), respectively. The CDR portions of antibody E3 (including Chothia and Kabat CDRs) are diagrammatically depicted in FIGS. 1A and 1B of WO2004/058184. The amino acid sequences of E3 heavy and light chains, and of the individual extended CDRs are also shown below (See, "antibody sequences", below). Antibody E3 is highly potent in sequestering NGF and preventing interaction with its receptor. E3 and its murine precursor antibody 911 have been shown to be an effective analgesic in non-clinical animal models of pathological pain including arthritis, cancer pain and post surgical pain.

In another aspect, the antibody comprises a fragment or a region of the antibody E3 (interchangeably termed "E3" herein). In one embodiment, the fragment is a light chain of the antibody E3 as shown in FIG. 1B of WO2004/058184 and SEQ ID No. 17 herein. In another embodiment, the fragment is a heavy chain of the antibody E3 as shown in FIG. 1A of WO2004/058184 and SEQ ID No. 16 herein. In yet another embodiment, the fragment contains one or more variable regions from a light chain and/or a heavy chain of the antibody E3. In yet another embodiment, the fragment contains one or more CDRs from a light chain and/or a heavy chain of the antibody E3 as shown in FIGS. 1A and 1B of WO2004/058184 and SEQ ID Nos. 17 and 16, respectively, herein.

In another aspect, the antibody comprises a light chain that is encoded by a polynucleotide that is produced by a host cell with a deposit number of ATCC No. PTA-4893 or ATCC No. PTA-4894. In another aspect, the antibody comprises a heavy chain that is encoded by a polynucleotide that is produced by a host cell with a deposit number of ATCC No. PTA-4895. In another aspect, the antibody comprises (a) a light chain that is encoded by a polynucleotide that is produced by a host cell with a deposit number of ATCC No. PTA-4894 or ATCC No. PTA-4893; and (b) a heavy chain that is encoded by a polynucleotide that is produced by a host cell with a deposit number of ATCC No. PTA-4895 (for convenience herein, the polynucleotide(s) produced by a deposited host cell are referred to as having a deposit number of ATCC NOs PTA-4894, PTA-4893 and PTA-4895). In another aspect, the antibody comprises a light chain variable region of a light chain that is encoded by a polynucleotide that is produced by a host cell with a deposit number of ATCC No. PTA-4894 or ATCC No. PTA-4893. In another aspect, the antibody comprises a heavy chain variable region of a heavy chain that that is encoded by a polynucleotide that is produced by a host cell with a deposit number of ATCC No. PTA-4895. In another aspect, the antibody comprises (a) a light chain variable region of a light chain that is encoded by a polynucleotide that is produced by a host cell with a deposit number of ATCC No. PTA-4894 or ATCC No. PTA-4893, and (b) a heavy chain variable region of a heavy chain that that is encoded by a polynucleotide that is produced by a host cell with a deposit number of ATCC No. PTA-4895. In still another aspect, the antibody comprises one or more CDR(s) encoded by (a) a polynucleotide that is produced by a host cell with a deposit number of ATCC No. PTA-4894; and/or (b) a heavy chain that is encoded by a polynucleotide that is produced by a host cell with a deposit number of ATCC No. PTA-4895.

In some embodiments, the antibody may be a full length antibody, which may be of the IgG2 subclass. The antibody may comprise the human heavy chain IgG2a constant region. In some embodiments the antibody comprises the human light chain kappa constant region. In some embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT WO9958572. The antibody may comprise a human heavy chain IgG2a constant region comprising the following mutations: A330P331 to S330S331 (amino acid numbering with reference to the wildtype IgG2a sequence).

In some embodiments, the antibody may be an antibody fragment, such as Fab or Fab'2 fragments, or a single chain antibody.

In another aspect, the antibody comprises any one or more of the following: a) one or more CDR(s) of antibody E3 shown in SEQ ID Nos. 1-8 (FIGS. 1A and 1B of WO2004/058184); b) CDR H3 from the heavy chain of antibody E3 shown in SEQ ID No. 1 and 5 (FIG. 1A of WO2004/058184); c) CDR L3 from the light chain of antibody E3 shown in SEQ ID No. 2 and 8 (FIG. 1B of WO2004/058184); d) three CDRs from the light chain of antibody E3 shown in SEQ ID No. 2, 6-8 (FIG. 1B of WO2004/058184); e) three CDRs from the heavy chain of antibody E3 shown in SEQ ID Nos. 1, 3-5 (FIG. 1A of WO2004/058184); and f) three CDRs from the light chain and three CDRs from the heavy chain, of antibody E3 shown in SEQ ID Nos. 1-8 (FIGS. 1A and 1B of WO2004/058184). In another aspect, the antibody may comprise any one or more of the following: a) one or more (one, two, three, four, five, or six) CDR(s) derived from antibody E3 shown in SEQ ID Nos. 1-8 (FIGS. 1A and 1B of WO2004/058184); b) a CDR derived from CDR H3 from the heavy chain of antibody E3 shown in SEQ ID Nos. 1 and 5 (FIG. 1A of WO2004/058184); and/or c) a CDR derived from CDR L3 from the light chain of antibody E3 shown in SEQ ID Nos. 2 and 8 (FIG. 1B of WO2004/058184). In some embodiments, the CDRs may be Kabat CDRs, Chothia CDRs, or a combination of Kabat and Chothia CDRs (termed "extended" or "combined" CDRs herein). In some embodiments, the polypeptides comprise any of the CDR configurations (including combinations, variants, etc.) described herein.

In one aspect, the antibody comprises a heavy chain variable region comprising SEQ ID NO:9, wherein I34 is S, L, V A, or I; and N35 is substituted with N, T or S. For convenience herein, "substituted" or "is" in this context or reference to an amino acid refers to choices of amino acid(s) for a given position. As is clear, the substitution, or choice, may be the amino acid depicted in a SEQ ID herein.

In another aspect, the antibody comprises a heavy chain variable region comprising SEQ ID NO:10, wherein M50 is M, I, G, Q, S, or L; A62 is A, or S; and L63 is L or V.

In another aspect, the antibody comprises a heavy chain variable region comprising SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T.

In another aspect, the antibody comprises a heavy chain variable region comprising SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the antibody comprises a heavy chain variable region comprising SEQ ID NO: 11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the antibody comprises a light chain variable region comprising SEQ ID NO:12, wherein S26 is S or F; D28 is D, S, A, or Y; and H32 is H, N, or Q.

In another aspect, the antibody comprises a light chain variable region comprising SEQ ID NO: 13, wherein I51 is I, T, V or A; and S56 is S or T.

In another aspect, the antibody comprises a light chain variable region comprising SEQ ID NO:14, wherein S91 is S or E; K92 is K, H, R, or S; and wherein Y96 is Y or R.

In another aspect, the antibody comprises a light chain variable region comprising SEQ ID NO:14, wherein S91 is S or E; K92 is any amino acid; T93 is any amino acid; and wherein Y96 is Y or R.

In one aspect, the antibody comprises an amino acid sequence shown in SEQ ID NO:9, wherein I34 is S, L, V A, or I; and N35 is N, T or S.

In another aspect, the antibody comprises an amino acid sequence shown in SEQ ID NO:10, wherein M50 is M, I, G, Q, S, or L; A62 is A, or S; and L63 is L or V.

In another aspect, the antibody comprises an amino acid sequence shown in SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T.

In another aspect, the antibody comprises an amino acid sequence shown in SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the antibody comprises an amino acid sequence shown in SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid.

In another aspect, the antibody comprises an amino acid sequence shown in SEQ ID NO:12, wherein S26 is S or F; D28 is D, S, A, or Y; and H32 is H, N, or Q.

In another aspect, the antibody comprises an amino acid sequence shown in SEQ ID NO: 13, wherein I51 is I, T, V or A; and S56 is S or T.

In another aspect, the antibody comprises an amino acid sequence shown in SEQ ID NO:14, wherein S91 is S or E; K92 is K, H, R, or S; and wherein Y96 is Y or R.

In another aspect, the antibody comprises an amino acid sequence shown in SEQ ID NO:14, wherein S91 is S or E; K92 is any amino acid; T93 is any amino acid; and wherein Y96 is Y or R.

In another aspect, the antibody comprises a heavy chain variable region comprising the CDR1 region of SEQ ID NO:9, wherein I34 is S, L, V A, or I; and N35 is N, T or S; the CDR2 region of SEQ ID NO:10, wherein M50 is M, I, G, Q, S, or L; A62 is A, or S; and L63 is L or V; and the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T. In some embodiments, the heavy chain variable region comprises the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the heavy chain variable region comprises the CDR3 region of SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, antibody further comprises an antibody light chain variable region.

In another aspect, the antibody comprises a light chain variable region comprising the CDR1 region of SEQ ID NO:12, wherein S26 is S or F; D28 is D, S, A, or Y; and H32 is H, N, or Q; the CDR2 region of SEQ ID NO:13, wherein I51 is I, T, V or A; and S56 is S or T; and the CDR3 region of SEQ ID NO:14, wherein S91 is S or E; K92 is K, H, R, or S; and wherein Y96 is Y or R. In some embodiments, the light chain variable region comprises the CDR3 region of SEQ ID NO:14, wherein S91 is S or E; K92 is any amino acid; T93 is any amino acid; and wherein Y96 is Y or R. In some embodiments, the antibody further comprises an antibody heavy chain.

In another aspect, the antibody comprises (a) a heavy chain variable region comprising the CDR1 region of SEQ ID NO:9, wherein I34 is S, L, V A, or I; and N35 is N, T or S; the CDR2 region of SEQ ID NO:10, wherein M50 is M, I, G, Q, S, or L; A62 is A, or S; and L63 is L or V; and the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T; and (b) a light chain variable region comprising the CDR1 region of SEQ ID NO:12, wherein S26 is S or F; D28 is D, S, A, or Y; and H32 is H, N, or Q; the CDR2 region of SEQ ID NO:13, wherein I51 is I, T, V or A; and S56 is S or T; and the CDR3 region of SEQ ID NO:14, wherein S91 is S or E; K92 is K, H, R, or S; and wherein Y96 is Y or R. In some embodiments, the light chain variable region comprises the CDR3 region of SEQ ID NO:14, wherein S91 is S or E; K92 is any amino acid; T93 is any amino acid; and wherein Y96 is Y or R. In some embodiments, the heavy chain variable region comprises the CDR3 region of SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the heavy chain variable region comprises the CDR3 region of SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the antibody further comprises an antibody light chain.

In another aspect, the antibody comprises an amino acid sequence shown in SEQ ID NO:9, wherein I34 is S, L, V A, or I; and N35 is N, T or S; an amino acid sequence shown in SEQ ID NO:10, wherein M50 is M, I, G, Q, S, or L; A62 is A, or S; and L63 is L or V; and an amino acid sequence shown in SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; wherein Y110 is Y, K, S, R or T. In some embodiments, the antibody comprises an amino acid sequence shown in SEQ ID NO:11, wherein Y100 is Y, L, or R; and wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In other embodiments, the polypeptide comprises an amino acid sequence shown in SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the antibody further comprises an antibody light chain variable region.

In another aspect, the antibody comprises an amino acid sequence shown in SEQ ID NO:12, wherein S26 is S or F; D28 is D, S, A, or Y; and H32 is H, N, or Q; an amino acid sequence shown in SEQ ID NO:13, wherein I51 is I, T, V or A; and S56 is S or T; and an amino acid sequence shown in SEQ ID NO:14, wherein S91 is S or E; K92 is K, H, R, or S; and wherein Y96 is Y or R. In some embodiments, the antibody comprises an amino acid sequence shown in SEQ ID NO:14, wherein S91 is S or E; K92 is any amino acid; T93 is any amino acid; and wherein Y96 is Y or R. In some embodiments, the antibody further comprises an antibody heavy chain variable region.

In another aspect, the antibody comprises (a) an amino acid sequence shown in SEQ ID NO:9, wherein I34 is S, L, V A, or I; and N35 is N, T or S; an amino acid sequence shown in SEQ ID NO:10, wherein M50 is M, I, G, Q, S, or L; A62 is A, or S; and L63 is L or V; and an amino acid sequence shown in SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T; and (b) an amino acid sequence shown in SEQ ID NO:12, wherein S26 is S or F; D28 is D, S, A, or Y; and H32 is H, N, or Q; an amino acid sequence shown in SEQ ID NO:13, wherein I51 is I, T, V or A; and S56 is S or T; and an amino acid sequence shown in SEQ ID NO:14, wherein S91 is S or E; K92 is K, H, R, or S; and wherein Y96 is Y or R. In some embodiments, the antibody comprises an amino acid sequence shown in SEQ ID NO:14, wherein S91 is S or E; K92 is any amino acid; T93 is any amino acid; and wherein Y96 is Y or R. In some embodiments, the antibody comprises an amino acid sequence shown in SEQ ID NO:11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; wherein Y110 is any amino acid. In other embodiments, the polypeptide comprises an amino acid sequence shown in SEQ ID NO:11, wherein G98 is G, S, A, C, V, N, D, or T; wherein G99 is G, S, A, C, V, N, D, or T; wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is S, A, C, G, D, N, T, or G; and wherein Y110 is any amino acid. In some embodiments, the antibody further comprises an antibody light chain variable region.

In another aspect, the antibody comprises a heavy chain variable region comprising: (a) a CDR1 region of SEQ ID NO:9, wherein I34 is S, L, V A, or I; and N35 is substituted with N, T or S; (b) a CDR2 region of SEQ ID NO:10, wherein M50 is I, G, Q, S, or L; A62 is A, or S; and L63 is L or V; and (c) a CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T; wherein the antibody binds NGF.

In another aspect, the antibody comprises a light chain variable region comprising: (a) a CDR1 region of SEQ ID NO:12, wherein S26 is S or F; D28 is D, S, A, or Y; and H32 is H, N, or Q; (b) a CDR2 region of SEQ ID NO: 13, wherein I51 is I, T, V or A; and S56 is S or T; and (c) a CDR3 region of SEQ ID NO:14, wherein K92 is K, H, R, or S; and wherein Y96 is Y or R; wherein the antibody binds NGF.

In another aspect, the antibody comprises (a) a heavy chain variable region comprising: (i) a CDR1 region of SEQ ID NO:9, wherein I34 is substituted with S, L, V A, or I; and N35 is substituted with N, T or S; (ii) a CDR2 region of SEQ ID NO:10, wherein M50 is I, G, Q, S, or L; A62 is A, or S; and L63 is L or V; and (iii) a CDR3 region of SEQ ID NO: 11, wherein Y100 is Y, L, or R; wherein Y101 is Y or W; wherein G103 is G, A, or S; wherein T104 is T or S; wherein S105 is S, A, or T; wherein Y106 is Y, R, T, or M; wherein Y107 is Y or F; wherein F108 is F or W; wherein D109 is D, N, or G; and wherein Y110 is Y, K, S, R or T; and (b) a light chain variable region comprising: (i) a CDR1 region of SEQ ID NO:12, wherein S26 is S or F; D28 is D, S, A, or Y; and H32 is H, N, or Q; (ii) a CDR2 region of SEQ ID NO: 13, wherein I51 is I, T, V or A; and S56 is S or T; and (iii) a CDR3 region of SEQ ID NO:14, wherein S91 is S or E; K92 is K, H, R, or S; and wherein Y96 is Y or R; wherein the antibody binds NGF.

Unless otherwise noted, choice (e.g., substitution) of an amino acid in one location is independently selected from selection of an amino acid in any other location.

In some embodiments, the antibodies comprise any of the CDR configurations (including combinations, variations, etc.) described herein.

As is evident from the description herein, the variable region numbering used herein is sequential numbering. One of skill in the art readily understands that a number of antibody numbering systems exist (such as Kabat and Chothia numbering), and how to convert sequential numbering into another numbering system, such as Kabat numbering or Chothia numbering.

In another aspect, the antibody comprises an amino acid sequence (such as a CDR3 sequence) selected from SEQ ID NO:46 or 50. In still other embodiments, the antibody further comprises one or more of the amino acid sequences shown in SEQ ID NOS:3, 4, 5, 6, 7, and 8. In still other embodiments, the antibody further comprises one of more of the amino acid sequences shown in SEQ ID NOS:9, 10, 11, 12, 13, 14, and 15.

In another aspect, the antibody comprises an amino acid sequence (such as a CDR region, such as a CDRH1 and/or CDR H2 region) selected from (a) SEQ ID NOS:28 and/or 29; (b) SEQ ID NOS:30 and/or 31; (c) SEQ ID NOS:32 and/or 33; (d) SEQ ID NOS:34 and/or 35; (e) SEQ ID NOS:36 and/or 37; (f) SEQ ID NOS:38 and/or 39; and (g) SEQ ID NOS:40 and 41. In some embodiments, the antibody comprises an amino acid sequence (such as a CDR H1 region) selected from SEQ ID NOS:28, 30, 32, 34, 36, 38, and 40. In some embodiments, the antibody comprises an amino acid sequence (such as a CDR H2 region) selected from SEQ ID NOS:29, 31, 33, 35, 37, 39 and 41. In still other embodiments, the antibody further comprises one or more of the amino acid sequences shown in SEQ ID NOS:3, 4, 5, 6, 7, and 8. In still other embodiments, the antibody further comprises one of more of the amino acid sequences shown in SEQ ID NOS:9, 10, 11, 12, 13, 14, and 15.

In another aspect, the antibody comprises an amino acid sequence (such as a CDR region, such as a CDRL1 and/or CDR L2 region) selected from (a) SEQ ID NOS:18 and/or 19; (b) SEQ ID NOS:20 and/or 21; and (c) SEQ ID NOS:22 and/or 23. In some embodiments, the polypeptide comprises an amino acid sequence (such as a CDR L1 region) selected from SEQ ID NOS:18, 20, and 22. In some embodiments, the antibody comprises an amino acid sequence (such as a CDR L2 region) selected from SEQ ID NOS:19, 21, and 23. In still other embodiments, the antibody further comprises one or more of the amino acid sequences shown in SEQ ID NOS:3, 4, 5, 6, 7, 8. In still other embodiments, the antibody further comprises one of more of the amino acid sequences shown in SEQ ID NOS:9, 10, 11, 12, 13, 14, and 15.

In another aspect, the antibody comprises an amino acid sequence (such as a CDR region, such as a CDRL3 and/or CDR H3 region) selected from (a) SEQ ID NOS:51 and/or 52; (b) SEQ ID NOS:55 and/or 56; (c) SEQ ID NOS:57 and/or 58; (c) SEQ ID NOS:59 and/or 60; (d) SEQ ID NOS:61 and/or 62; (e) SEQ ID NOS:63 and/or 64. In some embodiments, the antibody comprises an amino acid sequence (such as a CDR L3 region) selected from SEQ ID NOS:51, 55, 57, 59, 61, and 63. In some embodiments, the antibody comprises an amino acid sequence (such as a CDR H3 region) selected from SEQ ID NOS:52, 56, 58, 60, 62, and 64. In still other embodiments, the antibody further comprises an amino acid sequence shown in one or more of SEQ ID NOS:18, 19, 30 and 31. In still other embodiments, the antibody further comprises one or more of the amino acid sequences shown in SEQ ID NOS:3, 4, 5, 6, 7, and 8. In still other embodiments, the antibody further comprises one of more of the amino acid sequences shown in SEQ ID NOS:9, 10, 11, 12, 13, 14, and 15.

In another aspect, the antibody may comprise:
(a) a heavy chain variable region comprising:
(i) a CDR1 region of SEQ ID NO: 30;
(ii) a CDR2 region comprising the sequence of SEQ ID NO: 31;
(iii) a CDR3 region selected from the group consisting of SEQ ID NO: 11, 56, 58, 60, 62 and 64; and
(b) a light chain variable region comprising:
(i) a CDR1 region of SEQ ID NO: 18;
(ii) a CDR2 region of SEQ ID NO: 19;
(iii) a CDR3 region selected from the group consisting of SEQ ID NO: 14, 55, 57, 59, 61 and 63.

In another aspect, the antibody comprises one or more of an amino acid sequence (such as a CDR region) shown in SEQ ID NOS:61, 63, 18, 19, 30 and 31.

In another aspect, the antibody may be selected from an anti-NGF antibody known in the art, such as antibodies described in WO2005019266 (including antibodies 4D4, 14D10, 6G9, 7H2, 14F11 and 4G6) or WO2006131951 (including antibody Hu-αD11). The antibody may bind to the same epitope on NGF, particularly human NGF, as an anti-NGF antibody known in the art, such as antibodies described in WO2005019266 (including antibodies 4D4, 14D10, 6G9, 7H2, 14F11 and 4G6) or WO2006131951 (including antibody Hu-αD11), or an antibody defined herein, and/or may compete for binding to NGF with such an antibody.

In some embodiments, the C-terminal lysine of the heavy chain of any of the anti-NGF antibodies described herein is cleaved. In various cases, the heavy and light chains of the anti-NGF antibodies may optionally include a signal sequence.

In one aspect, the antibody is an anti-NGF antagonist antibody that binds NGF (such as human NGF) with a high affinity. In some embodiments, high affinity is (a) binding NGF with a $K_D$ of less than about 2 nM (such as any of about 1 nM, 800 pM, 600 pM, 400 pM, 200 pM, 100 pM, 90 pM, 80 pM, 70 pM, 60 pM, 50 pM, 40 pM, 30 pM, 20 pM, 10 pM 5 pM or less), and/or a $k_{off}$ of slower than about $6\times10^{-5}$ $s^{-1}$); and/or (b) inhibiting (reducing, and/or blocking) human NGF-dependent survival of mouse E13.5 trigeminal neurons with an IC50 (in the presence of about 15 pM of NGF) of about any of 200 pM, 150 pM, 100 pM, 80 pM, 60 pM, 40 pM, 20 pM, 10 pM, or less; and/or (c) inhibiting (reducing, and/or blocking) human NGF-dependent survival of mouse E13.5 trigeminal neurons with an IC50 (in the presence of about 1.5 pM of NGF) of about any of 50 pM, 40 pM, 30 pM, 10 pM, 20 pM, 10 pM, 5 pM, 2 pM, 1 pM, or less; and/or (d) inhibiting (reducing, and/or blocking) rat NGF-dependent survival of mouse E13.5 trigeminal neurons with an IC50 (in the presence of about 15 pM of NGF) of about any of 150 pM, 125 pM, 100 pM, 80 pM, 60 pM, 40 pM, 30 pM, 20 pM, 10 pM, 5 pM, or less; and/or (e) inhibiting (reducing, and/or blocking) rat NGF-dependent survival of mouse E13.5 trigeminal neurons with an IC50 (in the presence of about 1.5 pM of NGF) of about any of 30 pM, 25 pM, 20 pM, 15 pM, 10 pM, 5 pM, 4 pM, 3 pM, 2 pM, 1 pM, or less; and/or (f) and/or bind NGF with higher affinity than does the trkA receptor.

In another aspect, the antibodies (a) bind NGF (such as human NGF) with a $K_D$ of less than about 2 nM (such as any of about 1 nM, 800 pM, 600 pM, 400 pM, 200 pM, 100 pM, 90 pM, 80 pM, 70 pM, 60 pM, 50 pM, 40 pM, 30 pM, 20 pM, 10 pM, 5 pM or less), and/or a $k_{off}$ of slower than about $6\times10^{-5}$ $s^{-1}$); and/or (b) inhibit human NGF-dependent survival of mouse E13.5 trigeminal neurons with an IC50 (in the presence of about 15 pM of NGF) of about any of 200 pM, 150 pM, 100 pM, 80 pM, 60 pM, 40 pM, 20 pM, 10 pM, or less; and/or (c) inhibit human NGF-dependent survival of mouse E13.5 trigeminal neurons with an IC50 (in the presence of about 1.5 pM of NGF) of about any of 50 pM, 40 pM, 30 pM, 10 pM, 20 pM, 10 pM, 5 pM, 2 pM, 1 pM, or less; and/or bind NGF with higher affinity than does the trkA receptor. In some embodiments, the antibodies (a) bind NGF with a $K_D$ of less than about 2 nM; and/or (b) inhibit human NGF-dependent survival of mouse E13.5 trigeminal neurons with an IC50 of about 100 pM or less, wherein the IC50 is measured in the presence of about 15 pM NGF; and/or (c) inhibit human NGF-dependent survival of mouse E13.5 trigeminal neurons with an IC50 of about 10 pM or less, wherein the IC50 is measured in the presence of about 1.5 pM of NGF, wherein the IC50 is measured in the presence of about 15 pM NGF. In some embodiments, the antibodies (a) bind NGF with a $K_D$ of less than about 100 pM; and/or (b) inhibit human NGF-dependent survival of mouse E13.5 trigeminal neurons with an IC50 of about 20 pM or less, wherein the IC50 is measured in the presence of about 15 pM NGF; and/or (c) inhibit human NGF-dependent survival of mouse E13.5 trigeminal neurons with an IC50 of about 2 pM or less, wherein the IC50 is measured in the presence of about 1.5 pM of NGF.

In some embodiments, the above antibodies are isolated. In some embodiments, the antibody is substantially purified. In still other embodiments, the antibody is affinity matured. In some embodiments, the antibody comprises human framework sequences. In still other embodiments, the antibody comprises one or more non-human framework residues. In some embodiments, the antibody binds NGF (such as human NGF) with a $K_D$ of 2 nM or less. In some embodiments, the antibody comprises one or more (such as 2, 3, 4, 5, 6, 7, 8, or more) human amino acid substitutions relative to a non-human amino acid sequence (such as a variable region sequence, such as a CDR sequence, such as a framework sequence). In some embodiments, the antibody comprises at least 1, at least 2, or more such as at least 3, 4, 5, 6, or more amino acid substitutions relative to a parent polypeptide amino acid sequence (such as an antibody 911 amino acid sequence, such as any one or more of SEQ ID NOs 9-14). In some embodiments, the binding affinity of the antibody has been altered (in some embodiments, increased) relative to a parent antibody (such as Mab 911) affinity. In still other embodiments, the binding affinity of the antibody is lower than the binding affinity of trkA receptor for NGF (such as human NGF). In some embodiments, the antibodies are human antibodies. In other embodiments, the antibodies are humanized antibodies. In still other embodiments, the antibodies are monoclonal antibodies. In some embodiments, the antibody is an affinity matured antibody.

The invention utilises polynucleotides (including isolated polynucleotide) comprising polynucleotides encoding any of the antibodies of the embodiments above.

In another aspect, the invention provides an isolated polynucleotide comprising a polynucleotide encoding a fragment or a region of the antibody E3 (interchangeably termed "E3" herein). In one embodiment, the fragment is a light chain of the antibody E3 as shown in FIG. 1B of WO2004/058184. In another embodiment, the fragment is a heavy chain of the antibody E3 as shown in FIG. 1A of WO2004/058184. In yet another embodiment, the fragment contains one or more variable regions from a light chain and/or a heavy chain of the antibody E3. In yet another embodiment, the fragment contains one or more complementarity determining regions (CDRs) from a light chain and/or a heavy chain of the antibody E3 as shown in FIGS. 1A and 1B of WO2004/058184.

In another aspect, the invention is an isolated polynucleotide comprising a polynucleotide that encodes for antibody E3. In some embodiments, the polynucleotide comprises either or both of the polynucleotides shown in FIGS. 2 and 3 of WO2004/058184.

In another aspect, the invention utilises an isolated polynucleotide that encodes for an E3 light chain with a deposit number of ATCC No. PTA-4893 or ATCC No. PTA-4894. In another aspect, the invention is an isolated polynucleotide that encodes for an E3 heavy chain with a deposit number of ATCC No. PTA-4895. In yet another aspect, the isolated polynucleotide comprises (a) a variable region encoded in the polynucleotide with a deposit number of ATCC No. PTA-4893 or PTA-4894 and (b) a variable region encoded in the polynucleotide with a deposit number of ATCC No. PTA-4895. In another aspect, the isolated polynucleotide comprises (a) one or more CDR encoded in the polynucleotide with a deposit number of ATCC No. PTA-4893 or PTA-4894; and/or (b) one or more CDR encoded in the polynucleotide with a deposit number of ATCC No. PTA-4895.

In another aspect, the invention utilises polynucleotides encoding any of the antibodies (including antibody fragments) or polypeptides described herein.

In another aspect, the invention utilises vectors (including expression and cloning vectors) and host cells comprising any of the polynucleotides disclosed herein.

In another aspect, the invention utilises a host cell comprising a polynucleotide encoding E3 light chain and a polynucleotide encoding E3 heavy chain, wherein the polynucleotide(s) encoding E3 light chain has a deposit number of ATCC No. PTA-4893 and/or ATCC No. PTA-4894, and the polynucleotide encoding E3 heavy chain has a deposit number of ATCC No. PTA-4895. In some embodiments, the host cell comprises polynucleotide comprising (a) a variable region encoded in the polynucleotide with a deposit number of ATCC No. PTA-4893 or PTA-4894 and/or (b) a variable region encoded in the polynucleotide with a deposit number of ATCC No. PTA-4895. In some embodiments, the host cell comprises a polynucleotide encoding (a) one or more CDR encoded in the polynucleotide with a deposit number of ATCC No. PTA-4893 or PTA-4894; and/or (b) one or more CDR encoded in the polynucleotide with a deposit number of ATCC No. PTA-4895. In some embodiments, the host cell is a mammalian cell.

In another aspect, the invention provides an anti-NGF antagonist antibody for use in the treatment or prevention of pain and/or a lower urinary tract symptom (LUTS) associated with interstitial cystitis and/or painful bladder syndrome and/or bladder pain syndrome. The anti-NGF antagonist antibody may be as described herein.

Another aspect of the invention provides the use of an anti-NGF antagonist antibody in the manufacture of a medicament for the treatment or prevention of pain and/or a lower urinary tract symptom (LUTS) associated with interstitial cystitis and/or painful bladder syndrome and/or bladder pain syndrome. The anti-NGF antagonist antibody may be as described herein.

In another aspect, the invention is a pharmaceutical composition for use in the treatment or prevention of pain and/or a lower urinary tract symptom (LUTS) associated with interstitial cystitis and/or painful bladder syndrome and/or bladder pain syndrome, comprising any of the polypeptides (including antibodies such as antibody E3), polynucleotides or vectors described herein, such as pharmaceutical compositions comprising the antibody E3 or a fragment of the antibody E3, and a pharmaceutically acceptable excipient.

In another aspect, the invention provides kits and compositions comprising any one or more of the compositions described herein. These kits, generally in suitable packaging and provided with appropriate instructions, are useful for any of the methods described herein.

The invention also provides any of the compositions and kits described for any use described herein whether in the context of use as medicament and/or use for manufacture of a medicament.

Preferred features of each aspect of the invention apply equally to each other aspect mutatis mutandis.

DETAILED DESCRIPTION OF THE INVENTION

The invention disclosed herein provides methods for treating or preventing pain and/or a lower urinary tract symptom (LUTS) associated with interstitial cystitis and/or painful bladder syndrome and/or bladder pain syndrome in an individual by administration of a therapeutically effective amount of an anti-NGF antagonist antibody.

The invention disclosed herein also provides an anti-NGF antagonist antibody for use in the treatment or prevention of pain and/or a lower urinary tract symptom (LUTS) associated with interstitial cystitis and/or painful bladder syndrome and/or bladder pain syndrome. Further provided is the use of an anti-NGF antagonist antibody in the manufacture of a medicament for the treatment or prevention of pain and/or a lower urinary tract symptom (LUTS) associated with interstitial cystitis and/or painful bladder syndrome and/or bladder pain syndrome.

The invention disclosed herein provides the use of anti-NGF antagonist antibodies that bind NGF (such as human NGF) with high affinity. In some embodiments, the invention utilises a humanized antibody, E3, which binds to NGF. The invention also utilises E3 polypeptides (including antibodies) that bind NGF, and polynucleotides encoding E3 antibody and/or polypeptide. The invention further provides the use of antibodies and polypeptides derived from E3 that bind NGF.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv, dAb), single chain antibodies (ScFv), mutants thereof, chimeric antibodies, diabodies, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination. "Fv" is an antibody fragment that contains a complete antigen-recognition and -binding site. In a two-chain Fv species, this region consists of a dimer of one heavy and one light chain variable domain in tight, non-covalent association. In a single-chain Fv species, one heavy and one light chain variable domain can be covalently linked by a flexible peptide linker such that the light and heavy chains can associate in a dimeric structure analogous to that in a two-chain Fv species. It is in this configuration that the three CDRs of each variable domain interact to define an antigen-binding specificity on the surface of the VH-VL dimer. However, even a single variable domain (or half of a Fv comprising only 3 CDRs specific for an antigen) has the ability to recognize and bind antigen, although generally at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge regions. A F(ab)2 fragment is a bivalent fragment comprising two Fab fragments linked by a disulfide bridge at the hinge region.

A single chain antibody (scFc) is an antibody in which VL and VH regions are paired to form a monovalent molecule via a synthetic linker that enables them to be made as a single protein chain (Bird et al Science, 242: 423-426 (1988) and Huston et al., Proc. Natl. Acad. Sci. USA, 85:5879-5883 (1988)).

Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

An antibody can have one or more binding sites. If there is more than one binding site, the binding sites may be identical to one another or may be different. For instance, a naturally-occurring immunoglobulin has two identical binding sites, a single chain antibody or Fab fragment has one binding site, while a "bispecific" or "bifunctional" antibody (diabody) has two different binding sites.

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature.

A "monoclonal antibody" refers to a homogeneous antibody population wherein the monoclonal antibody is comprised of amino acids (naturally occurring and non-naturally occurring) that are involved in the selective binding of an antigen. A population of monoclonal antibodies is highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.).

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

"Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non human host organisms in combination with constant regions derived from, for example, human cell preparations. While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, PNAS (USA), 95:652-656.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

As used herein, the terms "E3", "3E", and "antibody E3" are used interchangeably to refer to an antibody comprising the amino acid sequence of the heavy chain and light chain variable regions shown in SEQ ID NO:1 and SEQ ID NO:2 (FIGS. 1A and 1B of WO2004/058184), respectively. The CDR portions of antibody E3 (including Chothia and Kabat CDRs) are diagrammatically depicted in FIGS. 1A and 1B of WO2004/058184. FIGS. 2 and 3 of WO2004/058184 show polynucleotides encoding heavy and light chains, respectively, comprising the heavy and light chain variable regions shown in FIGS. 1A and 1B, respectively. The generation and characterization of E3 is described in the Examples of WO2004/058184, the entire content of which is herein incorporated by reference. Different biological functions are associated with E3, including, but not limited to, ability to bind to NGF and inhibit NGF biological activity and/or downstream pathway(s) mediated by NGF signaling; and ability to inhibit NGF-dependent survival of mouse E13.5 trigeminal neurons. As discussed herein, antibodies for use in the invention may have any one or more of these characteristics. In some embodiments, the term "E3" refers to immunoglobulin encoded by (a) a polynucleotide encoding E3 light chain that has a deposit number of ATCC No. PTA-4893 or ATCC No. PTA-4894, and (b) a polynucleotide encoding E3 heavy chain that has a deposit number of ATCC No. PTA-4895.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

An epitope that "specifically binds", or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an NGF epitope is an antibody that binds this epitope with greater affinity, avidity, more readily, and/or with greater duration than it binds to other NGF epitopes or non-NGF epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "identity" refers to the percent "identity" of two amino acid sequences or of two nucleic acid sequences. The percent identity is generally determined by aligning the sequences for optimal comparison purposes (e.g. gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al (1990) J. Mol. Biol. 215:403-410 have incorporated such an algorithm. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) Nucliec Acids Res. 25:3389-3402. Alternatively, PSI-Blast can be used to perform an iterated search that detects distant relationships between molecules (Id.) When utilizing BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller, CABIOS (1989). The ALIGN program (version 2.0) which is part of the GCG sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

As used herein, the term "nerve growth factor" and "NGF" refers to nerve growth factor and variants thereof that retain at least part of the biological activity of NGF. As used herein, NGF includes all mammalian species of native sequence NGF, including human, canine, feline, equine, or bovine.

"NGF receptor" refers to a polypeptide that is bound by or activated by NGF. NGF receptors include the TrkA receptor and the p75 receptor of any mammalian species, including, but are not limited to, human, canine, feline, equine, primate, or bovine.

As used herein, an "anti-NGF antagonist antibody" (interchangeably termed "anti-NGF antibody") refers to an antibody which is able to bind to NGF and inhibit NGF biological activity and/or downstream pathway(s) mediated by NGF signaling. An anti-NGF antagonist antibody encompasses antibodies that block, antagonize, suppress or reduce (including significantly) NGF biological activity, including downstream pathways mediated by NGF signaling, such as receptor binding and/or elicitation of a cellular response to NGF. For purpose of the present invention, it will be explicitly understood that the term "anti-NGF antagonist antibody" encompass all the previously identified terms, titles, and functional states and characteristics whereby the NGF itself, an NGF biological activity (including but not limited to its ability to ability to mediate any aspect of post-surgical pain), or the consequences of the biological activity, are substantially nullified, decreased, or neutralized in any meaningful degree. In some embodiments, an anti-NGF antagonist antibody binds NGF and prevent NGF dimerization and/or binding to an NGF receptor (such as p75 and/or trkA). In other embodiments, an anti-NGF antibody binds NGF and prevents trkA receptor dimerization and/or trkA autophosphorylation. Examples of anti-NGF antagonist antibodies are provided herein.

"Biological activity" of NGF generally refers to the ability to bind NGF receptors and/or activate NGF receptor signaling pathways. Without limitation, a biological activity includes any one or more of the following: the ability to bind an NGF receptor (such as p75 and/or trkA); the ability to promote trkA receptor dimerization and/or autophosphorylation; the ability to activate an NGF receptor signaling pathway; the ability to promote cell differentiation, proliferation, survival, growth and other changes in cell physiology, including (in the case of neurons, including peripheral and central neuron) change in neuronal morphology, synaptogenesis, synaptic function, neurotransmitter and/or neuropeptide release and regeneration following damage; the ability to promote survival of mouse E13.5 trigeminal neurons; and the ability to mediate pain and/or lower urinary tract symptoms associated with interstitial cystitis and/or painful bladder syndrome and/or bladder pain syndrome.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "treatment" is an approach for obtaining beneficial or desired clinical results. For purposes of this invention, beneficial or desired clinical results include, but are not limited to, one or more of the following: improvement or alleviation of any aspect of pain and/or a lower urinary tract symptom associated with interstitial cystitis and/or painful bladder syndrome and/or bladder pain syndrome. For purposes of this invention, beneficial or desired clinical results include, but are not limited to, one or more of the following: including lessening severity, alleviation of pain and/or a lower urinary tract symptom associated with interstitial cystitis and/or painful bladder syndrome and/or bladder pain syndrome including any aspect of pain (such as shortening duration of pain, reduction of pain sensitivity or sensation).

An "effective amount" of drug, compound, or pharmaceutical composition is an amount sufficient to effect beneficial or desired results including clinical results such as alleviation or reduction in pain sensation. An effective amount can be administered in one or more administrations. For purposes of this invention, an effective amount of drug, compound, or pharmaceutical composition is an amount sufficient to treat, ameliorate, reduce the intensity of and/or prevent pain or a lower urinary tract symptom associated with interstitial cystitis and/or painful bladder syndrome and/or bladder pain syndrome. In some embodiments, the "effective amount" may reduce pain at rest (resting pain) or mechanically-induced pain (including pain following movement), or both, and it may be administered before, during or after painful stimulus. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

"Reducing incidence" of pain and/or a lower urinary tract symptom associated with interstitial cystitis and/or painful bladder syndrome and/or bladder pain syndrome means any of reducing severity (which can include reducing need for and/or amount of (e.g., exposure to) other drugs and/or therapies generally used for this conditions, including, for example, opiates), duration, and/or frequency (including, for example, delaying or increasing time pain in an individual). As is understood by those skilled in the art, individuals may vary in terms of their response to treatment, and, as such, for example, a "method of reducing incidence of pain and/or a lower urinary tract symptom associated with interstitial cystitis and/or painful bladder syndrome and/or bladder pain syndrome in an individual" reflects administering the anti-NGF antagonist antibody based on a reasonable expectation that such administration may likely cause such a reduction in incidence in that particular individual.

"Ameliorating" a pain and/or a lower urinary tract symptoms associated with interstitial cystitis and/or painful bladder syndrome and/or bladder pain syndrome means a lessening or improvement of one or more symptoms of pain and/or a lower urinary tract symptoms associated with interstitial cystitis and/or painful bladder syndrome and/or bladder pain syndrome as compared to not administering an anti-NGF antagonist antibody. "Ameliorating" also includes shortening or reduction in duration of a symptom.

"Palliating" pain and/or a lower urinary tract symptom associated with interstitial cystitis and/or painful bladder syndrome and/or bladder pain syndrome means lessening the extent of one or more undesirable clinical manifestations of pain and/or lower urinary tract symptoms in an individual or population of individuals.

As used therein, "delaying" the development of pain means to defer, hinder, slow, retard, stabilize, and/or postpone progression of pain and/or a lower urinary tract symptom associated with interstitial cystitis and/or painful bladder syndrome and/or bladder pain syndrome. This delay can be of varying lengths of time, depending on the history of the disease and/or individuals being treated. As is evident to one skilled in the art, a sufficient or significant delay can, in effect, encompass prevention, in that the individual does not develop pain. A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Pain" as used herein refers to pain of any etiology, including acute and chronic pain, and any pain with an inflammatory component. As used herein, "pain" includes nociception and the sensation of pain, and pain can be assessed objectively and subjectively, using pain scores and other methods well-known in the art. The pain can be primary or secondary pain, as is well-known in the art.

"Pain associated with interstitial cystitis and/or painful bladder syndrome and/or bladder pain syndrome" as used herein refers to lower abdominal (pelvic) pain; bladder pain; suprapubic pain; vaginal pain; pain in the penis, testicles, scrotum and perineum; urethral pain; dyspareneuria; pain, pressure or discomfort that may increase as the bladder fills.

"Lower urinary tract symptoms associated with interstitial cystitis and/or painful bladder syndrome and/or bladder pain syndrome" as used herein refers to three groups of urinary symptoms, which may be defined as storage (irritative), voiding (obstructive) and post-micturition symptoms. Storage symptoms comprise urgency, frequency, nocturia, urgency incontinence and stress incontinence, which can be associated with overactive bladder (OAB) and benign prostatic hyperplasia (BPH). Voiding symptoms comprise hesitancy, poor flow, intermittency, straining and dysuria. Post-micturition symptoms comprise terminal dribbling, post-void dribbling and a sense of incomplete emptying.

"Over Active Bladder (OAB)" is defined as urgency, with or without urge incontinence, usually with frequency and nocturia [Abrams et al., Neurourology and Urodynamics 21:167-178 (2002)]. Prevalence of OAB in men and women is similar, with approximately 16% of the population of the USA suffering from the condition [Stewart et al, Prevalence of Overactive Bladder in the United States: Results from the NOBLE Program; Abstract Presented at the 2$^{nd}$ International Consultation on Incontinence, July 2001, Paris, France].

The terms OAB Wet and OAB Dry describe OAB patients with or without urinary incontinence respectively. Previously, the cardinal symptom of OAB was believed to be urinary incontinence. However, with the advent of the new terms this is clearly not meaningful for the large number of sufferers who are not incontinent (i.e. OAB Dry patients). Thus, a 2001 study from Liberman et al ['Health Related Quality of Life Among Adults with Symptoms of Overactive Bladder: Results From A US Community-Based Survey'; Urology 57(6), 1044-1050, 2001] examined the impact of all OAB symptoms on the quality of life of a community-based sample of the US population. This study demonstrated that individuals suffering from OAB without any demonstrable loss of urine have an impaired quality of life when compared with controls.

"BPH" is a chronically progressive disease that can lead to complications such as acute urinary retention, recurrent urinary tract infections, bladder stones and renal dysfunction. The prevalence and average severity of LUTS associated with BPH in men increases with age. BPH leads to an increase in prostate volume, creating urethral and bladder outflow obstruction as well as secondary changes in bladder function. The effects of this are manifested by both storage (irritative) and voiding (obstructive) symptoms.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" or "subject" is a vertebrate, preferably a mammal, more preferably a human. Mammals include, but are not limited to, farm animals (such as cows), sport animals, pets (such as cats, dogs and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$K_{off}$", as used herein, is intended to refer to the off rate constant for dissociation of an antibody from the antibody-antigen interaction. The term "$K_{on}$", as used herein, is intended to refer to the on-rate or association rate of a particular antibody-antigen interaction. The term "$K_D$", as used herein, is intended to refer to the dissociation constant of an antibody-antigen interaction, which is obtained from the ratio of $K_{off}$ to $K_{on}$ and is expressed as a molar concentration (M). $K_D$ values for antibodies can be determined using methods well established in the art. One method for determining the $K_D$ of an antibody is by using surface plasmon resonance, typically using a biosensor system such as a Biacore® system.

Methods of Using Anti-NGF Antagonist Antibody for Treating or Preventing Pain and/or a Lower Urinary Tract Symptom Associated with Interstitial Cystitis and/or Painful Bladder Syndrome and/or Bladder Pain Syndrome The invention provides methods for treating or preventing pain and/or a lower urinary tract symptom associated with interstitial cystitis and/or painful bladder syndrome and/or bladder pain syndrome in individuals including mammals, both human and non-human. Accordingly, in one aspect, the invention provides methods of treating or preventing pain and/or a lower urinary tract symptom associated with interstitial cystitis and/or painful bladder syndrome and/or bladder pain syndrome in an individual comprising administering an effective amount of an anti-NGF antagonist antibody. Suitable anti-NGF antagonist antibodies are described herein.

In another aspect, the invention provides methods for reducing incidence of, ameliorating, suppressing, palliating, and/or delaying the onset, the development or the progression of pain and/or a lower urinary tract symptom associated with interstitial cystitis and/or painful bladder syndrome and/or bladder pain syndrome in an individual. Thus, in some embodiments, the anti-NGF antagonist antibody is administered prior to development of pain and/or a lower urinary tract symptom associated with interstitial cystitis and/or painful bladder syndrome and/or bladder pain syndrome in an individual having interstitial cystitis and/or painful bladder syndrome and/or bladder pain syndrome.

An anti-NGF antagonist antibody may be administered to an individual via any suitable route. Examples of different administration route are described herein.

In some embodiments, the anti-NGF antagonist antibody is administered once every week, once every two weeks, once every three weeks, once every four weeks, once every five weeks, once every six weeks, once every seven weeks, once every eight weeks, once every nine weeks, once every ten weeks, once every fifteen weeks, once every twenty weeks, once every twenty five weeks, or once every twenty six weeks. In some embodiments, the anti-NGF antagonist antibody is administered once every month, once every two months, once every three months, once every four months, once every five months, or once every six months.

Pain relief or relief from lower urinary tract symptoms may be characterized by time course of relief. Accordingly, in some embodiments, relief is observed within about 24 hours after administration of an anti-NGF antagonist antibody. In other embodiments, relief is observed within about 36, 48, 60, 72 hours or 4 days after administration of the anti-NGF antagonist antibody. In some embodiments, frequency and/or intensity of pain and/or lower urinary tract symptom is diminished, and/or quality of life of those suffering the disease is increased. In some embodiments, pain relief is provided for duration of at least about 7 days, at least about 14 days, at least about 21 days, at least about 28 days, at least about 35 days, at least about 42 days, at least about 49 days, at least about 56 days, at least about 63 days, at least about 70 days, at least about 77 days, at least about 84 days, at least about 180 days, or longer after a single dose of the anti-NGF antagonist antibody.

Pain relief or relief from lower urinary tract symptoms may be characterized by a change in a pain numerical rating scale (NRS), a change in the O'Leary-Sant Interstitial Cystitis Symptom Index (ICSI), a change in the O'Leary-Sant Interstitial Cystitis Problem Index (ICPI), a change in the Pelvic Pain and Urgency/Frequency (PUF) symptom score and/or changes in micturition variables including micturition frequency, nocturnal frequency, incontinence episode frequency, mean volume voided per micturition, mean interstitial cystitis pain severity, urinary urgency episodes, average sleep disturbance score, average pain associated with sexual activity pain score, global response assessment, patent reporting treatment impact assessment, treatment failure, biomarkers, safety endpoints and/or pharmacokinetic measures. Biomarkers may include NGF, glycoprotein-51 (GP-51), antiproliferative factor (APF) and HB-Epidermal growth factor (HB-EGF), amongst others.

Exemplary anti-NGF antibodies for use in the methods of the invention (pertaining to pain and/or lower urinary tract symptoms associated with interstitial cystitis and/or painful bladder syndrome and/or bladder pain syndrome) are anti-NGF antagonist antibodies, which refer to any antibody that blocks, suppresses or reduces (including significantly) NGF biological activity, including downstream pathways mediated by NGF signaling, such as receptor binding and/or elicitation of a cellular response to NGF. The term "antagonist" implies no specific mechanism of biological action whatsoever, and is deemed to expressly include and encompass all possible pharmacological, physiological, and biochemical interactions with NGF and its consequences which can be achieved by a variety of different, and chemically divergent, compositions. For purpose of the present invention, it will be explicitly understood that the term "antagonist" encompasses all the previously identified terms, titles, and functional states and characteristics whereby the NGF itself, an NGF biological activity (including but not limited to its ability to mediate any aspect of pain), or the consequences of the biological activity, are substantially nullified, decreased, or neutralized in any meaningful degree. In some embodiments, an anti-NGF antagonist antibody binds (physically interact with) NGF, binds to an NGF receptor (such as TrkA receptor and/or p75 receptor), and/or reduces (impedes and/or blocks) downstream NGF receptor signaling. In some embodiment, the anti-NGF antagonist antibody binds NGF (such as hNGF) and does not significantly bind to related neurotrophins, such as NT-3, NT4/5, and/or BDNF. In some embodiments, the anti-NGF antagonist antibody is not associated with an adverse immune response. In still other embodiments, the anti-NGF antibody is humanized (such as antibody E3 described herein). In some embodiments, the anti-NGF antibody is antibody E3 (as described herein). In other embodiments, the anti-NGF antibody comprises one or more CDR(s) of antibody E3 (such as one, two, three, four, five, or, in some embodiments, all six CDRs from E3). In other embodiments, the antibody is human. In still other embodiments, the anti-NGF antibody comprises the amino acid sequence of the heavy chain variable region shown in SEQ ID No. 1 (FIG. 1A of WO2004/058184) and/or the amino acid sequence of the light chain variable region shown in SEQ ID NO:2 (FIG. 1B of WO2004/058184). In still other embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in Eur. J. Immunol. (1999) 29:2613-2624; PCT WO9958752.

The antibodies for use in the methods of the invention are characterized by any (one or more) of the following characteristics: (a) ability to bind to NGF; (b) ability to reduce and/or inhibit NGF biological activity and/or downstream pathway(s) mediated by NGF signaling; (c) ability to reduce and/or inhibit NGF-dependent survival of mouse E13.5 trigeminal neurons; (d) absence of any significant cross-reactivity to NT3, NT4/5, and/or BDNF; (e) ability to treat and/or prevent pain and/or lower urinary tract symptoms associated with interstitial cystitis and/or painful bladder syndrome and/or bladder pain syndrome; (f) ability to increase clearance of NGF; (g) ability to reduce or inhibit activation of trkA receptor, as detected, for example, using kinase receptor activation assay (KIRA) (see U.S. Pat. No. 6,027,927).

For purposes of this invention, the antibody reacts with NGF in a manner that inhibits NGF and/or downstream pathways mediated by the NGF signaling function. In some embodiments, the anti-NGF antagonist antibody recognizes human NGF. In yet other embodiments, the anti-NGF antagonist antibody specifically binds human NGF. In some embodiment, the anti-NGF antagonist antibody does not significantly bind to related neurotrophins, such as NT-3, NT4/5, and/or BDNF. In still other embodiments, the anti-NGF antibody is capable of binding NGF and effectively inhibiting the binding of NGF to its TrkA and/or p75 receptor in vivo and/or effectively inhibiting NGF from activating its TrkA and/or p75 receptor. In still other embodiments, the anti-NGF antagonist antibody is a monoclonal antibody. In still other embodiments, the anti-NGF antibody is humanized (such as antibody E3 described herein). In some embodiments, the anti-NGF antibody is human. See for example, WO 2005/019266 which describes antibodies 4D4, 14D10, 6G9, 7H2, 14F11 and 4G6. In one embodiment, the antibody is a human antibody which recognizes one or more epitopes on human NGF. In another embodiment, the antibody is a mouse or rat antibody which recognizes one or more epitopes on human NGF. In another embodiment, the antibody recognizes one or more epitopes on an NGF selected from the group consisting of: primate, canine, feline, equine, and bovine. In still further embodiments, the anti-NGF antagonist antibody binds essentially the same NGF epitope as an antibody selected from any one or more of the following: MAb 911, MAb 912 and MAb 938 (See Hongo, et al., Hybridoma 19:215-227 (2000)); an antibody as defined herein (such as antibody E3); and/or an antibody described in WO20050019266 (including antibodies 4D4, 14D10, 6G9, 7H2, 14F11 and 4G6) or WO2006131951 (including antibody Hu-αD11). In other embodiments, the antibody binds the same epitope as Mab 911. In another embodiment, the antibody comprises a constant region that is immunologically inert (e.g., does not trigger complement mediated lysis or antibody dependent cell mediated cytotoxicity (ADCC)). ADCC activity can be assessed using methods disclosed in U.S. Pat. No. 5,500,362. In some embodiments, the constant region is modified as described in Eur. J. Immunol. (1999) 29:2613-2624; PCT WO9958752.

In some embodiments, the anti-NGF antagonist antibody is a humanized mouse anti-NGF monoclonal antibody termed antibody "E3", any of the E3 related antibodies described herein, or any fragments thereof.

The binding properties of antibody E3, which binds human NGF with high affinity and slow dissociation kinetics, compared with parent murine anti-NGF monoclonal antibody 911, are summarized below. E3 binds human NGF with an approximately 50-fold higher binding affinity than parent mouse antibody 911.

| antibody | $k_D$ | $K_{off}$ | $K_{on}$ |
|---|---|---|---|
| 911 (Fab) | 3.7 nM | $9 \times 10^{-5}$ s$^{-1}$ | $2.2 \times 10^4$ M$^{-1}$s$^{-1}$ |
| E3 (Fab) | 0.07 nM | $<4 \times 10^{-5}$ s$^{-1}$ | $6 \times 10^5$ M$^{-1}$s$^{-1}$ |

The E3 antibody and related antibodies also exhibit a strong capacity to antagonize human NGF, as assessed by in vitro assays described in Examples 2 and 3 of WO2004/058184 the content of which is incorporated herein by reference. For example, antibody E3 antagonizes the NGF-dependent survival of mouse E13 trigeminal neurons at an IC50 of about 21 pM in the presence of 15 pM of human NGF, and about 1.2 pM in the presence of 1.5 pM of human NGF.

Accordingly, in another aspect, the antibodies and polypeptides of the invention may be further identified and characterized by: (h) high affinity binding to human NGF with low dissociation kinetics (in some embodiments, with a $K_D$ of less than about 2 nM, and/or a koff of slower than about 6×10-5 s-1) and/or (i) ability to inhibit (block) NGF-dependent survival of mouse E13.5 trigeminal neurons with an IC50 of about 100 pM or less at about 15 pM of NGF (in some embodiments, human NGF) and/or an IC50 of about 20 pM or less at about 1.5 pM of NGF.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion, humanized antibodies, human antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the invention utilises an antibody comprising a light chain that is encoded by a polynucleotide that is produced by a host cell with a deposit number of ATCC No. PTA-4893 or ATCC No. PTA-4894. In another aspect, the antibody comprises a heavy chain that is encoded by a polynucleotide that is produced by a host cell with a deposit number of ATCC No. PTA-4895. The present invention also utilises various formulations of E3 and equivalent antibody fragments (e.g., Fab, Fab', F(ab')$_2$, Fv, Fc, etc.), single chain (ScFv), mutants thereof, fusion proteins comprising an antibody portion, and any other modified configuration of E3 that comprises an antigen (NGF) recognition site of the required specificity. The equivalent antibodies of E3, including antibody and polypeptide fragments (which may or may not be antibodies) of E3, and polypeptides comprising polypeptide fragments of E3 are identified and characterized by any (one or more) of the criteria described above.

Accordingly, the invention utilises any of the following, or compositions (including pharmaceutical compositions) comprising any of the following: (a) antibody E3; (b) a fragment or a region of the antibody E3; (c) a light chain of the antibody E3 as shown in SEQ ID No. 17 (FIG. 1B of WO2004/058184); (c) a heavy chain of the antibody E3 as shown in SEQ ID No. 16 (FIG. 1A of WO2004/058184); (d) one or more variable region(s) from a light chain and/or a heavy chain of the antibody E3; (e) one or more CDR(s) (one, two, three, four, five or six CDRs) of antibody E3 shown in SEQ ID Nos. 3-8 (FIGS. 1A and 1B of WO2004/058184); (f) CDR H3 from the heavy chain of antibody E3 shown in SEQ ID No. 5 (FIG. 1A of WO2004/058184); (g) CDR L3 from the light chain of antibody E3 shown in SEQ ID No. 8 (FIG. 1B of WO2004/058184); (h) three CDRs from the light chain of antibody E3 shown in SEQ ID Nos. 6-8 (FIG. 1B of WO2004/058184); (i) three CDRs from the heavy chain of antibody E3 shown in SEQ ID No. 3-5 (FIG. 1A of WO2004/058184); (j) three CDRs from the light chain and three CDRs from the heavy chain, of antibody E3 shown in SEQ ID Nos 3-8 (FIGS. 1A and 1B of WO2004/058184); and (k) an antibody comprising any one of (b) through (j).

The CDR portions of antibody E3 (including Chothia and Kabat CDRs) are diagrammatically depicted in FIGS. 1A and 1B of WO2004/058184), and consist of the following amino acid sequences:

```
                                              (SEQ ID NO: 3)
(a)  heavy chain CDR 1 ("CDR H1")  GFSLIGYDLN;

(SEQ ID NO: 4)
(b)  heavy chain CDR 2 ("CDR H2")  IIWGDGTTDYNSAVKS;

(SEQ ID NO: 5)
(c)  heavy chain CDR 3 ("CDR H3")  GGYWYATSYYFDY;

(SEQ ID NO: 6)
(d)  light chain CDR 1 ("CDR L1")  RASQSISNNLN;

(SEQ ID NO: 7)
(e)  light chain CDR 2 ("CDR L2")  YTSRFHS;
and (SEQ ID NO: 8)
(f)  light chain CDR 3 ("CDR L3")  QQEHTLPYT.
```

Determination of CDR regions is well within the skill of the art. It is understood that in some embodiments, CDRs can be a combination of the Kabat and Chothia CDR (also termed "combined CDRs" or "extended CDRs"). In some embodiments, the CDRs comprise the Kabat CDR. In other embodiments, the CDRs are the Chothia CDR.

In some embodiments, the antibody comprises at least one CDR that is substantially homologous to at least one CDR, at least two, at least three, at least four, at least 5 CDRs of E3 (or, in some embodiments substantially homologous to all 6 CDRs of E3, or derived from E3). Other embodiments include antibodies which have at least two, three, four, five, or six CDR(s) that are substantially homologous to at least two, three, four, five or six CDRs of E3 or derived from E3. It is understood that, for purposes of this invention, binding specificity and/or overall activity (which may be in terms of treating and/or preventing pain or inhibiting NGF-dependent survival of E13.5 mouse trigeminal neurons) is generally retained, although the extent of activity may vary compared to E3 (may be greater or lesser).

In some embodiments, the antibody may comprise an amino acid sequence of E3 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of E3, wherein at least 3 of the amino acids are from a variable region of E3. The extended CDR sequences of Mab 911 are shown in FIGS. 1A and 1B of WO2004/058184, and in SEQ ID NOS:9-14 herein. In one embodiment, the variable region is from a light chain of E3. In another embodiment, the variable region is from a heavy chain of E3. In another embodiment, the 5 (or more) contiguous amino acids are from a complementarity determining region (CDR) of E3 shown in SEQ ID Nos 3-8 (FIGS. 1A and 1B of WO2004/058184).

In another embodiment, the antibody comprises an amino acid sequence of E3 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of E3, wherein the E3 sequence comprises any one or more of: amino acid residue L29 of CDRH1, I50 of CDRH2, W101 of CDRH3, and/or A103 of CDRH3; and/or amino acid residue S28 of CDRL1, N32 of CDRL1, T51 of CDRL2, 91 E of CDRL3 and/or H92 of CDRL3.

As is evident, throughout this disclosure, a sequential amino acid numbering scheme is used to refer to amino acid residues in the variable regions (that is, the amino acid residues in each variable region are numbered in sequence). As is well known in the art, the Kabat and/or Chothia numbering systems are useful when comparing two antibodies or polypeptides, such as an E3 antibody and an E3 variant (or polypeptide suspected of being an E3 variant). It is well understood in the art how to convert sequential numbering to Chothia and/or Kabat numbering, if desired, for example, for use in making comparisons between E3 and another polypeptide. FIG. 23 of WO2004/058184 depicts the E3 variable regions numbered using sequential, Chothia and Kabat numbering. In addition, to facilitate comparison, generally it is understood that framework residues generally, but not always, have approximately the same number of residues. However, the CDRs may vary in size (i.e., it is possible to have insertions and/or deletions of one or more amino acid residues). When comparing an E3 antibody and a candidate E3 variant (for example, in the case of a CDR region from a candidate sequence which is longer in the sequence in antibody E3 to which is aligned), one may follow the following steps (though other methods are known in the art). The candidate antibody sequence is aligned with E3 antibody heavy chain and light chain variable regions. Alignment may be done by hand, or by computer using commonly accepted computer programs. Alignment may be facilitated by using some amino acid residues which are common to most Fab sequences. For example, the light and heavy chains each typically have two cysteines, which are often found at a conserved position. It is understood that the amino acid sequence of a candidate variant antibody may be longer (i.e. have inserted amino acid residues) or shorter (have deleted amino acid residues). Suffixes may be added to the residue number to indicate the insertion of additional residues, e.g., residue 34 abc. For candidate sequences which, for example, align with a E3 sequence for, e.g., residues 33 and 35, but have no residue between them to align with residue 35, the residue 35 is simply not assigned to a residue. In another approach, it is generally well known that comparison may be made between structural equivalent (e.g., same position in the antigen-antibody complex) amino acids when comparing CDRs of different lengths. For example, the Chothia numbering (Al-Lazikani et al, supra) generally (but not in all cases), places insertions and deletions at the structurally correct positions. Structural equivalence may also be deduced or demonstrated using X-ray crystallography or double mutant cycle analysis (see Pons et al. (1999) Prot. Sci. 8:958-968).

The binding affinity of an anti-NGF antibody to NGF (such as hNGF) can be, in terms of $K_D$, about 0.10 to about 0.80 nM, about 0.15 to about 0.75 nM and about 0.18 to about 0.72 nM.

In some embodiments, the $K_D$ is about 2 pM, about 5 pM, about 10 pM, about 15 pM, about 20 pM, about 40 pM, or greater than about 40 pM. In one embodiment, the $K_D$ is between about 2 pM and 22 pM. In other embodiments, the $K_D$ is less than about 10 nM, about 5 nM, about 4 nM, about 3.5 nM, about 3 nM, about 2.5 nM, about 2 nM, about 1.5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM, about 5 pM. In some embodiments, the $K_D$ is about 10 nM. In other embodiments, the $K_D$ is less than about 10 nM. In other embodiments, the $K_D$ is about 0.1 nM or about 0.07 nM. In other embodiments, the $K_D$ is less than about 0.1 nM or less than about 0.07 nM. In other embodiments, the $K_D$ is any of about 10 nM, about 5 nM, about 4 nM, about 3.5 nM, about 3 nM, about 2.5 nM, about 2 nM, about 1.5 nM, about 1 nM, about 900 pM, about 800 pM, bout 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM to any of about 2 pM, about 5 pM, about 10 pM, about 15 pM, about 20 pM, or about 40 pM. In some embodiments, the $K_D$ is any of about 10 nM, about 5 nM, about 4 nM, about 3.5 nM, about 3 nM, about 2.5 nM, about 2 nM, about 1.5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In still other embodiments, the $K_D$ is about 2 pM, about 5 pM, about 10 pM, about 15 pM, about 20 pM, about 40 pM, or greater than about 40 pM.

The binding affinity of the antibody to NGF can be determined using methods well known in the art. One way of determining binding affinity of antibodies to NGF is by measuring binding affinity of monofunctional Fab fragments of the antibody. To obtain monofunctional Fab fragments, an antibody (for example, IgG) can be cleaved with papain or expressed recombinantly. The affinity of an anti-NGF Fab fragment of an antibody can be determined by surface plasmon resonance (BIAcore3000™ surface plasmon resonance (SPR) system, BIAcore, INC, Piscaway N.J.). CM5 chips can be activated with N-ethyl-N'-(3-dimethylaminopropyl)-carbodiimide hydrochloride (EDC) and N-hydroxysuccinimide (NHS) according to the supplier's instructions. Human NGF (or any other NGF) can be diluted into 10 mM sodium acetate pH 4.0 and injected over the activated chip at a concentration of 0.005 mg/mL. Using variable flow time across the individual chip channels, two ranges of antigen density can be achieved: 100-200 response units (RU) for detailed kinetic studies and 500-600 RU for screening assays. The chip can be blocked with ethanolamine. Regeneration studies have shown that a mixture of Pierce elution buffer (Product No. 21004, Pierce Biotechnology, Rockford Ill.) and 4 M NaCl (2:1) effectively removes the bound Fab while keeping the activity of hNGF on the chip for over 200 injections. HBS-EP buffer (0.01M HEPES, pH 7.4, 0.15 NaCl, 3 mM EDTA, 0.005% Surfactant P29) is used as running buffer for the BIAcore assays. Serial dilutions (0.1-10× estimated $K_D$) of purified Fab samples are injected for 1 min at 100 μL/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6.99-110) using the BIAevaluation program. Equilibrium dissociation constant ($K_D$) values are calculated as $k_{off}/k_{on}$. This protocol is suitable for use in determining binding affinity of an antibody to any NGF, including human NGF, NGF of another vertebrate (in some embodiments, mammalian) (such as mouse NGF, rat NGF, primate NGF), as well as for use with other neurotrophins, such as the related neurotrophins NT3, NT4/5, and/or BDNF.

In some embodiments, the antibody binds human NGF, and does not significantly bind an NGF from another vertebrate species (in some embodiment, mammalian). In some embodiments, the antibody binds human NGF as well as one or more NGF from another vertebrate species (in some embodiments, mammalian). In still other embodiments, the antibody binds NGF and does not significantly cross-react with other neurotrophins (such as the related neurotrophins, NT3, NT4/5, and/or BDNF). In some embodiments, the antibody binds NGF as well as at least one other neurotrophin. In some embodiments, the antibody binds to a mammalian species of NGF, such as horse or dog, but does not significantly bind to NGF from anther mammalian species.

The epitope(s) can be continuous or discontinuous. In one embodiment, the antibody binds essentially the same human NGF epitopes as an antibody selected from the group consisting of MAb 911, MAb 912, and MAb 938 as described in Hongo et al., Hybridoma, 19:215-227 (2000); an antibody defined herein (such as antibody E3); and/or an antibody described in WO2005019266 (including antibodies 4D4, 14D10, 6G9, 7H2, 14F11 and 4G6) or WO2006131951 (including antibody Hu-αD11), the entire contents of which are herein incorporated by reference. In another embodiment, the antibody binds essentially the same hNGF epitope as MAb 911. In still another embodiment, the antibody binds essentially the same epitope as MAb 909. Hongo et al., supra. For example, the epitope may comprise one or more of: residues K32, K34 and E35 within variable region 1 (amino acids 23-35) of hNGF; residues F79 and T81 within variable region 4 (amino acids 81-88) of hNGF; residues H84 and K88 within variable region 4; residue R103 between variable region 5 (amino acids 94-98) of hNGF and the C-terminus (amino acids 111-118) of hNGF; residue E11 within pre-variable region 1 (amino acids 10-23) of hNGF; Y52 between variable region 2 (amino acids 40-49) of hNGF and variable region 3 (amino acids 59-66) of hNGF; residues L112 and S113 within the C-terminus of hNGF; residues R59 and R69 within variable region 3 of hNGF; or residues V18, V20, and G23 within pre-variable region 1 of hNGF. In addition, an epitope can comprise one or more of the variable region 1, variable region 3, variable region 4, variable region 5, the N-terminus region, and/or the C-terminus of hNGF. In still another embodiment, the antibody significantly reduces the solvent accessibility of residue R103 of hNGF. It is understood that although the epitopes described above relate to human NGF, one of ordinary skill can align the structures of human NGF with the NGF of other species and identify likely counterparts to these epitopes.

In some embodiments, the antibodies for use in the invention may inhibit (reduce, and/or block) human NGF-dependent survival of mouse E13.5 trigeminal neurons with an IC50 (in the presence of about 15 pM of NGF) of about any of 200 pM, 150 pM, 100 pM, 80 pM, 60 pM, 40 pM, 20 pM, 10 pM, or less. In some embodiments, the antibodies or peptides of the invention may inhibit (reduce, and/or block) human NGF-dependent survival of mouse E13.5 trigeminal neurons with an IC50 (in the presence of about 1.5 pM of NGF) of about any of 50 pM, 40 pM, 30 pM, 10 pM, 20 pM, 10 pM, 5 pM, 2 pM, 1 pM, or less. In some embodiments, the antibodies or peptides of the invention may inhibit (reduce, and/or block) rat NGF-dependent survival of mouse E13.5 trigeminal neurons with an IC50 (in the presence of about 15 pM of NGF) of about any of 150 pM, 125 pM, 100 pM, 80 pM, 60 pM, 40 pM, 30 pM, 20 pM, 10 pM, 5 pM, or less. In some embodiments, the antibodies may inhibit (reduce, and/or block) rat NGF-dependent survival of mouse E13.5 trigeminal neurons with an IC50 (in the presence of about 1.5 pM of NGF) of about any of 30 pM, 25 pM, 20 pM, 15 pM, 10 pM, 5 pM, 4 pM, 3 pM, 2 pM, 1 pM, or less. Methods for measurement of the NGF-dependent survival of mouse E13 trigeminal neurons are known in the art, and described, e.g., in Example 2 of WO2004/058184).

Identification of Anti-NGF Antagonist Antibodies

Anti-NGF antagonist antibodies for use in the invention can be identified or characterized using methods known in the art, whereby reduction, amelioration, or neutralization of an NGF biological activity is detected and/or measured. Methods described in PCT WO 04/065560 can be used. Another method, for example, a kinase receptor activation (KIRA) assay described in U.S. Pat. Nos. 5,766,863 and 5,891,650, can be used to identify anti-NGF agents. This ELISA-type assay is suitable for qualitative or quantitative measurement of kinase activation by measuring the autophosphorylation of the kinase domain of a receptor protein tyrosine kinase (hereinafter "rPTK"), e.g. TrkA receptor, as well as for identification and characterization of potential antagonists of a selected rPTK, e.g., TrkA. The first stage of the assay involves phosphorylation of the kinase domain of a kinase receptor, for example, a TrkA receptor, wherein the receptor is present in the cell membrane of an eukaryotic cell.

The receptor may be an endogenous receptor or nucleic acid encoding the receptor, or a receptor construct, may be transformed into the cell. Typically, a first solid phase (e.g., a well of a first assay plate) is coated with a substantially homogeneous population of such cells (usually a mammalian cell line) so that the cells adhere to the solid phase. Often, the cells are adherent and thereby adhere naturally to the first solid phase. If a "receptor construct" is used, it usually comprises a fusion of a kinase receptor and a flag polypeptide. The flag polypeptide is recognized by the capture agent, often a capture antibody, in the ELISA part of the assay. An analyte, such as a candidate NGF antagonist (including anti-NGF antagonist antibody) is then added together with NGF to the wells having the adherent cells, such that the tyrosine kinase receptor (e.g. TrkA receptor) is exposed to (or contacted with) NGF and the analyte. This assay enables identification of antagonists (including antibodies) that inhibit activation of TrkA by its ligand NGF. Following exposure to NGF and the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate.

The cell lysate thus prepared is then ready to be subjected to the ELISA stage of the assay. As a first step in the ELISA stage, a second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used. The cell lysate obtained is then exposed to, or contacted with, the adhering capture agent so that the receptor or receptor construct adheres to (or is captured in) the second solid phase. A washing step is then carried out, so as to remove unbound cell lysate, leaving the captured receptor or receptor construct. The adhering or captured receptor or receptor construct is then exposed to, or contacted with, an anti-phosphotyrosine antibody which identifies phosphorylated tyrosine residues in the tyrosine kinase receptor. In one embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule. Finally, binding of the anti-phosphotyrosine antibody to the captured receptor or receptor construct is measured, e.g., by a color change in the color reagent.

Anti-NGF antagonist antibodies can also be identified by incubating a candidate agent with NGF and monitoring any one or more of the following characteristics: (a) binding to NGF and inhibiting NGF biological activity or downstream pathways mediated by NGF signaling function; (b) inhibiting, blocking or decreasing NGF receptor activation (including TrkA dimerization and/or autophosphorylation); (c) increasing clearance of NGF; (d) treating or preventing any aspect of pain and/or lower urinary tract symptoms associated with interstitial cystitis and/or painful bladder syndrome and/or bladder pain syndrome; (e) inhibiting (reducing) NGF synthesis, production or release. In some embodiments, an NGF antagonist (e.g., an anti-NGF antagonist antibody) is identified by incubating an candidate agent with NGF and monitoring binding and/or attendant reduction or neutralization of a biological activity of NGF. The binding assay may be performed with purified NGF polypeptide(s), or with cells naturally expressing, or transfected to express, NGF polypeptide(s). In one embodiment, the binding assay is a competitive binding assay, where the ability of a candidate agent (such as an antibody) to compete with a known anti-NGF antagonist antibody for NGF binding is evaluated. The assay may be performed in various formats, including the ELISA format. In other embodiments, an NGF antagonist (such as anti-NGF antagonist antibody) is identified by incubating a candidate agent with NGF and monitoring binding and attendant inhibition of trkA receptor dimerization and/or autophosphorylation.

Following initial identification, the activity of a candidate anti-NGF antagonist antibody can be further confirmed and refined by bioassays, known to test the targeted biological activities. Alternatively, bioassays can be used to screen candidates directly. For example, NGF promotes a number of morphologically recognizable changes in responsive cells. These include, but are not limited to, promoting the differentiation of PC12 cells and enhancing the growth of neurites from these cells (Greene et al., Proc Natl Acad Sci USA. 73(7):2424-8, 1976), promoting neurite outgrowth from explants of responsive sensory and sympathetic ganglia (Levi-Montalcini, R. and Angeletti, P. Nerve growth factor. Physiol. Rev. 48:534-569, 1968) and promoting the survival of NGF dependent neurons such as embryonic dorsal root ganglion, trigeminal ganglion, or sympathetic ganglion neurons (e.g., Chun & Patterson, Dev. Biol. 75:705-711, (1977); Buchman & Davies, Development 118:989-1001 (1993). Thus, the assay for inhibition of NGF biological activity entail culturing NGF responsive cells with NGF plus an analyte, such as a candidate NGF antagonist (including anti-NGF antagonist antibody). After an appropriate time the cell response will be assayed (cell differentiation, neurite outgrowth or cell survival).

The ability of a candidate NGF antagonist antibody to block or neutralize a biological activity of NGF can also be assessed by monitoring the ability of the candidate agent to inhibit NGF mediated survival in the embryonic rat dorsal root ganglia survival bioassay as described in Hongo et al., Hybridoma 19:215-227 (2000).

The antibodies for use in this invention can be made by procedures known in the art, some of which are illustrated in the Examples of WO2004/058184. The antibodies can be produced by proteolytic or other degradation of the antibodies, by recombinant methods (i.e., single or fusion polypeptides) as described in WO2004/058184 or by chemical synthesis. Polypeptides of the antibodies, especially shorter polypeptides up to about 50 amino acids, are conveniently made by chemical synthesis. Methods of chemical synthesis are known in the art and are commercially available. For example, a E3 antibody could be produced by an automated polypeptide synthesizer employing the solid phase method. See also, U.S. Pat. Nos. 5,807,715; 4,816,567; and 6,331,415. Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

In another alternative, the antibodies can be made recombinantly using procedures that are well known in the art. In one embodiment, a polynucleotide comprising a sequence encoding the variable and light chain regions of antibody E3 is cloned into a vector for expression or propagation in a host cell (e.g., CHO cells). In another embodiment, the polynucleotide sequences shown in FIGS. 2 and 3 of WO2004/058184 are cloned into one or more vectors for expression or propagation. The sequence encoding the antibody of interest may be maintained in a vector in a host cell and the host cell can then be expanded and frozen for future use. Vectors (including expression vectors) and host cells are further described herein. Methods for expressing antibodies recombinantly in plants or milk have been disclosed. See, for example, Peeters et al. (2001) Vaccine 19:2756; Lonberg, N. and D. Huszar (1995) Int. Rev. Immunol 13:65; and Pollock et al. (1999) J Immunol Methods 231:147. Methods for making derivatives of antibodies, e.g., humanized, single chain, etc. are known in the art.

The invention also encompasses single chain variable region fragments ("scFv") of antibodies of this invention, such as E3. Single chain variable region fragments are made by linking light and/or heavy chain variable regions by using a short linking peptide. Bird et al. (1988) Science 242:423-426. An example of a linking peptide is (GGGGS)3 (SEQ ID NO:15), which bridges approximately 3.5 nm between the carboxy terminus of one variable region and the amino terminus of the other variable region. Linkers of other sequences have been designed and used (Bird et al. (1988)). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad Sci. USA 90:6444-6448; Poljak, R. J., et al. (1994) Structure 2:1121-1123).

The antibody may be a bispecific antibody, a monoclonal antibody that has binding specificities for at least two different antigens. A bispecific antibody can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods.

Suitable cross-linking agents and techniques are well known in the art, and are described in U.S. Pat. No. 4,676,980.

The antibody may be a humanized antibody, for example, as known in the art, and as described herein.

The invention encompasses modifications to antibody E3, including functionally equivalent antibodies which do not significantly affect their properties and variants which have enhanced or decreased activity. Modification of polypeptides is routine practice in the art and is further exemplified in the Examples. Examples of modified polypeptides include polypeptides with substitutions (including conservative substitutions) of amino acid residues, one or more deletions or additions of amino acids which do not significantly deleteriously change the functional activity, or use of chemical analogs.

A polypeptide "variant," as used herein, is a polypeptide that differs from a native protein in one or more substitutions, deletions, additions and/or insertions, such that the immunoreactivity of the polypeptide is not substantially diminished. In other words, the ability of a variant to specifically bind antigen may be enhanced or unchanged, relative to the native protein, or may be diminished by less than 50%, and preferably less than 20%, relative to the native protein. Polypeptide variants preferably exhibit at least about 80%, more preferably at least about 90% and most preferably at least about 95% identity (determined as described herein) to the identified polypeptides.

Amino acid sequence variants of the antibodies may be prepared by introducing appropriate nucleotide changes into the antibody DNA, or by peptide synthesis. Such variants include, for example, deletions from, and/or insertions into and/or substitutions of, residues within the amino acid sequences of SEQ ID NO:1 or 2 described herein. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis or modification is called "alanine scanning mutagenesis," and is described by Cunningham and Wells, 1989, Science, 244:1081-1085. A residue or group of target residues is identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity. Library scanning mutagenesis, as described herein, may also be used to identify locations in an antibody that are suitable for mutagenesis or modification.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Hydrophobic: Norleucine, Met, Ala, Val, Leu, Ile;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro; and
(6) Aromatic: Trp, Tyr, Phe.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiment, no more than one to five conservative amino acid substitutions are made within a CDR domain. In other embodiments, no more than one to three conservative amino acid substitutions are made within a CDR3 domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of $\beta(1,4)$-N-acetyl-glucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetyl-galactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified E3 polypeptides are made using established procedures in the art and can be screened using standard assays known in the art, some of which are described below and in the Examples.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The invention also utilises fusion proteins comprising one or more fragments or regions from the antibodies or polypeptides of this invention. In one embodiment, a fusion polypeptide is provided that comprises at least 10 contiguous amino acids of the variable light chain region shown in SEQ ID No. 2 (FIG. 1B of WO2004/058184) and/or at least 10 amino acids of the variable heavy chain region shown in SEQ ID No. 1 (FIG. 1A of WO2004/058184). In another embodiment, the fusion polypeptide comprises a light chain variable region and/or a heavy chain variable region of E3, as shown in SEQ ID Nos. 1 and 2 (FIGS. 1A and 1B of WO2004/058184). In another embodiment, the fusion polypeptide comprises one or more CDR(s) of E3. In still other embodiments, the fusion polypeptide comprises CDR H3 and/or CDR L3 of antibody E3. In another embodiment, the fusion polypeptide comprises any one or more of: amino acid residue L29 of CDRH1, 150 of CDRH2, W101 of CDRH3, and/or A103 of CDRH3; and/or amino acid residue S28 of CDRL1, N32 of CDRL1, T51 of CDRL2, 91 E of CDRL3 and/or H92 of CDRL3. For purposes of this invention, a E3 fusion protein contains one or more E3 antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A E3 fusion polypeptide can be created by methods known in the art, for example, synthetically or recombinantly. Typically, the E3 fusion proteins are made by preparing an expressing a polynucleotide encoding them using recombinant methods described herein, although they may also be prepared by other means known in the art, including, for example, chemical synthesis.

The ability of the antibodies and polypeptides of this invention, such as binding NGF; reducing or inhibiting a NGF biological activity; reducing and/or blocking NGF-induced survival of E13.5 mouse trigeminal neurons, may be tested using methods known in the art, some of which are described in the Examples of WO2004/058184 and in particular in Examples 2 and 3 of WO2004/058184.

The invention also utilises compositions (including pharmaceutical compositions) and kits comprising antibody E3, and, as this disclosure makes clear, any or all of the antibodies and/or polypeptides described herein. Such compositions and kits may be for use in treating and/or preventing one or more pain and/or lower urinary tract symptoms associated with interstitial cystitis and/or painful bladder syndrome and/or bladder pain syndrome in an individual.

Polynucleotides, Vectors and Host Cells

The invention also provides isolated polynucleotides encoding the antibodies and polypeptides of the invention (including an antibody comprising the polypeptide sequences of the light chain and heavy chain variable regions shown in FIGS. 1A and 1B of WO2004058184), and vectors and host cells comprising the polynucleotide for use in the methods of the invention.

Accordingly, the polynucleotides (or compositions, including pharmaceutical compositions), may comprise polynucleotides encoding any of the following: (a) antibody E3; (b) a fragment or a region of the antibody E3; (c) a light chain of the antibody E3 as shown in SEQ ID No. 17 (FIG. 1B of WO2004/058184); (d) a heavy chain of the antibody E3 as shown in SEQ ID No. 16 (FIG. 1A of WO2004/058184); (e) one or more variable region(s) from a light chain and/or a heavy chain of the antibody E3; (f) one or more CDR(s) (one, two, three, four, five or six CDRs) of antibody E3 shown in SEQ ID Nos. 3-8 (FIGS. 1A and 1B of WO2004/058184); (g) CDR H3 from the heavy chain of antibody E3 shown SEQ ID No. 5 (FIG. 1A of WO2004/058184; (h) CDR L3 from the light chain of antibody E3 shown in SEQ ID No. 8 (FIG. 1B of WO2004/058184); (i) three CDRs from the light chain of antibody E3 shown in SEQ ID No. 6-8 (FIG. 1B of WO2004/058184); (j) three CDRs from the heavy chain of antibody E3 shown in SEQ ID Nos. 3-5 (FIG. 1A of WO2004/058184); (k) three CDRs from the light chain and three CDRs from the heavy chain, of antibody E3 shown in SEQ ID Nos. 3-8 (FIGS. 1A and 1B of WO2004/058184; or (l) an antibody comprising any of (b) to (k). In some embodiments, the polynucleotide comprises either or both of the polynucleotide(s) shown in SEQ ID Nos. 76 and 77 (FIGS. 2 and 3 of WO2004/058184).

In another aspect, the invention utilises an isolated polynucleotide that encodes for an E3 light chain with a deposit number of ATCC No. PTA-4893 or ATCC No. PTA-4894. In another aspect, the invention utilises an isolated polynucleotide that encodes for an E3 heavy chain with a deposit number of ATCC No. PTA-4895. In yet another aspect, the invention utilises an isolated polynucleotide comprising (a) a variable region encoded in the polynucleotide with a deposit number of ATCC No. PTA-4894 and (b) a variable region encoded in the polynucleotide with a deposit number of ATCC No. PTA-4895. In another aspect, the invention utilises an isolated polynucleotide comprising (a) one or more CDR encoded in the polynucleotide with a deposit number of ATCC No. PTA-4894; and/or (b) one or more CDR encoded in the polynucleotide with a deposit number of ATCC No. PTA-4895. The deposits under ATCC Accession Nos. PTA-4893, PTA-4894 and PTA-4895 are described in WO2004/058184, the content of which is incorporated herein in its entirety.

The polynucleotides encoding any of the antibodies (including antibody fragments) and polypeptides described herein can be made by procedures known in the art In another aspect, the invention provides compositions (such as a pharmaceutical compositions) comprising any of the polynucleotides of the invention for use in treating or preventing pain and/or a lower urinary tract symptom associated with interstitial cystitis and/or painful bladder syndrome and/or bladder pain syndrome. In some embodiments, the composition comprises an expression vector comprising a polynucleotide encoding the E3 antibody as described herein. In other embodiment, the composition comprises an expression vector comprising a polynucleotide encoding any of the antibodies or polypeptides described herein. In still other embodiments, the composition comprises either or both of the polynucleotides shown in FIGS. 2 and 3 of WO2004/058184. Expression vectors, and administration of polynucleotide compositions are further described herein.

In another aspect, the invention provides a method of making any of the polynucleotides described herein for use in methods for treating or preventing pain and/or a lower urinary tract symptom associated with interstitial cystitis and/or painful bladder syndrome and/or bladder pain syndrome.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645

Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides for use in the invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also utilises host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to NGF is effected by an immunoassay or FACS. A cell overexpressing the antibody or protein of interest can be identified.

Compositions for Use in the Methods of the Invention

The compositions for use in the methods of the invention (pertaining to pain and/or lower urinary tract symptoms associated with interstitial cystitis and/or painful bladder syndrome and/or bladder pain syndrome) comprise an effective amount of an anti-NGF antagonist antibody, and, in some embodiments, further comprise a pharmaceutically acceptable excipient. Examples of such compositions, as well as how to formulate, are also described herein. In some embodiments, the anti-NGF antagonist antibody binds NGF and does not significantly cross-react with related neurotrophins (such as NT3, NT4/5, and/or BDNF). In some embodiments, the anti-NGF antagonist antibody is not associated with an adverse immune response. In other embodiments, the anti-NGF antibody recognizes human NGF. In some embodiments, the anti-NGF antibody is human. In still other embodiments, the anti-NGF antibody is humanized (such as antibody E3 described herein). In still other embodiment, the anti-NGF antibody comprises a constant region that does not trigger an unwanted or undesirable immune response, such as antibody-mediated lysis or ADCC. In other embodiments, the anti-NGF antibody comprises one or more CDR(s) of antibody E3 (such as one, two, three, four, five, or, in some embodiments, all six CDRs from E3).

It is understood that the compositions can comprise more than one NGF antagonist. For example, a composition can comprise more than one member of a class of NGF antagonist (e.g., a mixture of anti-NGF antibodies that recognize different epitopes of NGF), as well as members of different classes of NGF antagonists (e.g., an anti-NGF antibody and an NGF inhibitory compound). Other exemplary compositions comprise more than one anti-NGF antibodies that recognize the same epitope(s), different species of anti-NGF antibodies that bind to different epitopes of NGF, or different NGF inhibitory compounds.

The composition used in the present invention can further comprise pharmaceutically acceptable carriers, excipients, or stabilizers (Remington: The Science and Practice of Pharmacy 20th Ed. (2000) Lippincott Williams and Wilkins, Ed. K. E. Hoover.), in the form of lyophilized formulations or aqueous solutions. Pharmaceutically acceptable excipients are further described herein.

The anti-NGF antagonist antibody and compositions thereof can also be used in conjunction with other agents that serve to enhance and/or complement the effectiveness of the agents, for example with agents used in the treatment or prevention of pain and/or lower urinary tract symptoms. The anti-NGF antagonist antibody may be administered simultaneously, sequentially or separately in combination with one or more of such agents.

The anti-NGF antibody may be administered in combination with one or more other drugs (or as any combination thereof). The anti-NGF antibody may be usefully combined with another pharmacologically active compound, or with two or more other pharmacologically active compounds, for the treatment of a pain and/or a lower urinary tract symptom (LUTS) associated with interstitial cystitis and/or painful bladder syndrome and/or bladder pain syndrome. For example, an anti-NGF antibody, as defined above, may be administered simultaneously, sequentially or separately, in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, terazosin, indoramin, alfuzosin, silodosin or 4-amino-6,7- dimethoxy-2-(5-methane-sulfonamido-1,2,3,4-tetrahydroisoquinol-2-yl)-5-(2-pyridyl)quinazoline; prazosin a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g oxybutynin, tolterodine, fesoterodine, 5-hydroxymethyltolterodine, propiverine, trospium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular acetaminophen/paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist (eg pizotifen), and particularly a $5-HT_{1B/1D}$ agonist such as eletriptan, sumatriptan, naratriptan, zolmitriptan or rizatriptan;

a $5-HT_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol (trade mark);

a PDE-5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2'1',1:6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-amino-5-methyl-nonanoic acid, (3R,4R,5R)-3-amino-4,5-dimethyl-heptanoic acid and (3R,4R,5R)-3-amino-4,5-dimethyl-octanoic acid; (3S,5R)-3-aminomethyl-5-methyloctanoic acid;

a cannabinoid;

metabotropic glutamate subtype 1 receptor (mGluR1) antagonist;

a serotonin reuptake inhibitor such as sertraline, sertraline metabolite desmethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin $E_2$ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl),1,4-benzoquinone (CV-6504);

a sodium channel blocker, such as lidocaine; or bupivicaine a 5-HT3 antagonist, such as ondansetron;

glycosaminoglycan layer replacer and anti-inflammatory, such as pentosan polysulphate (Elmiron—trade mark);

a beta-3 agonist, such as YM-178 (mirabegron or 2-amino-N-[4-[2-[[(2R)-2-hydroxy-2-phenylethyl]amino]ethyl] phenyl]-4-thiazoleacetamide), solabegron, KUC-7483 (ritobegron or 2-[4-[2-[[(1S,2R)-2-hydroxy-2-(4-hydroxyphenyl)-1-methylethyl]amino]ethyl]-2,5-dimethylphenoxy]-acetic acid) or AK-134;

an anti-histamine, such as hydroxyzine;

a $H_2$-antagonist, such as cimetidine; or ranitidine silver nitrate;

a steroid;

doxorubicin;

chondroitin sulphate;

disodium chromoglycate;

oxychlorosene (Clorpactin—trade mark); and an immunosuppressant, such as cyclosporine and the pharmaceutically acceptable salts and solvates thereof.

Administration of an Anti-NGF Antagonist Antibody

The anti-NGF antagonist antibody can be administered to an individual (for pain and/or lower urinary tract symptoms associated with interstitial cystitis and/or painful bladder syndrome and/or bladder pain syndrome) via any suitable route. It should be apparent to a person skilled in the art that the examples described herein are not intended to be limiting but to be illustrative of the techniques available. Accordingly, in some embodiments, the anti-NGF antagonist antibody is administered to an individual in accord with known methods, such as intravenous administration, e.g., as a bolus or by continuous infusion over a period of time, by intramuscular, intraperitoneal, intracerebrospinal, subcutaneous, intra-articular, sublingually, intrasynovial, via insufflation, intrathecal, oral, inhalation transdermal or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-NGF antagonist antibody can be aerosolized using a fluorocarbon formulation and a metered dose inhaler, or inhaled as a lyophilized and milled powder.

In one embodiment, an anti-NGF antagonist antibody is administered via site-specific or targeted local delivery techniques. Examples of site-specific or targeted local delivery techniques include various implantable depot sources of the anti-NGF antagonist antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of antibodies such as E3 or fragments thereof (e.g., Fab, Fab', F(ab')2, Fv, Fc, etc.), such as single chain (ScFv), mutants thereof, fusion proteins comprising an antibody portion, and any other modified configuration that comprises an antigen NGF recognition site of the required specificity, may be used for administration. In some embodiments the anti-NGF antagonist antibody may be administered neat. In some embodiments, anti-NGF antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-NGF antibody can be administered using any suitable method, including by injection (e.g., intraperitoneally, intravenously, subcutaneously, intramuscularly, etc.). Anti-NGF antibodies can also be administered via inhalation or by other forms of administration (e.g. oral, mucosal, sublingually), as described herein. Generally, for administration of anti-NGF antibodies, an initial candidate dosage can be about 2 mg/kg.

In a preferred embodiment, the concentration of the antibody to be administered can range from about 0.1 to about 200 mg/ml. Preferably the concentration of antibody is about 0.5 mg/ml, about 1 mg/ml, about 2 mg/ml, about 3 mg/ml, about 4 mg/ml, about 5 mg/ml, about 6 mg/ml, about 7 mg/ml, about 8 mg/ml, about 9 mg/ml, about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, about 30 mg/ml, about 31 mg/ml, about 32 mg/ml, about 33 mg/ml, about 34 mg/ml, about 35 mg/ml, about 36 mg/ml, about 37 mg/ml, about 38 mg/ml, about 39 mg/ml, about 40 mg/ml, about 41 mg/ml, about 42 mg/ml, about 43 mg/ml, about 44 mg/ml, about 45 mg/ml, about 46 mg/ml, about 47 mg/ml, about 48 mg/ml, about 49 mg/ml, about 50 mg/ml, about 51 mg/ml, about 52 mg/ml, about 53 mg/ml, about 54 mg/ml, about 55 mg/ml, about 56 mg/ml, about 57 mg/ml, about 58 mg/ml, about 59 mg/ml, about 60 mg/ml, about 70 mg/ml, about 80 mg/ml, about 90 mg/ml, about 100 mg/ml or about 110 mg/ml.

Most preferably the concentration of antibody is selected from the group comprising about 2 mg/ml, about 2.5 mg/ml, about 5 mg/ml, about 10 mg/ml, about 20 mg/ml, about 22 mg/ml and about 50 mg/ml.

In some embodiments, the administration pattern of the anti-NGF antibody comprises administration of a dose once every week, once every 2 weeks, every 3 weeks, every 4 weeks, every 5 weeks, every 6 weeks, every 7 weeks, every 8 weeks, every 9 weeks, every 10 weeks, every 15 weeks, every 20 weeks, every 25 weeks, or longer. In some embodiments, the antibody is administered once every 1 month, every 2 months, every 3 months, every 4 months, every 5 months, every 6 months, or longer. Most preferably, the anti-NGF antibody is administered once every 8 weeks. The progress of this therapy may be monitored by conventional techniques and assays. The dosing regimen (including the NGF antagonist(s) used) can vary over time.

In some embodiments the volume of a dose is less than or equal to about 20 ml, about 15 ml, about 10 ml, about 5 ml, about 2.5 ml, about 1.5 ml, about 1.0 ml, about 0.75 ml, about 0.5 ml, about 0.25 ml or about 0.01 ml. In some embodiments the volume of a dose is about 20 ml, about 19 ml, about 18 ml, about 17 ml, about 16 ml, about 15 ml, about 14 ml, about 13 ml, about 12 ml, about 11 ml, about 10 ml, about 9 ml, about 8 ml, about 7 ml, about 6 ml, about 5 ml, about 4 ml, about 3 ml, about 2 ml or about 1 ml. Alternatively about 20.5 ml, about 19.5 ml, about 18.5 ml, about 17.5 ml, about 16.5 ml, about 15.5 ml, about 14.5 ml, about 13.5 ml, about 12.5 ml, about 11.5 ml, about 10.5 ml, about 9.5 ml, about 8.5 ml, about 7.5 ml, about 6.5 ml, about 5.5 ml, about 4.5 ml, about 3.5 ml, about 2.5 ml, about 1.5 ml, or about 0.5. Alternatively about 900 µl, about 800 µl, about 700 µl, about 600 µl, about 500 µl, about 400 µl, about 300 µl, about 200 µl, or about 100 µl, alternatively about 950 µl, about 850 µl, about 750 µl, about 650 µl, about 550 µl, about 450 µl, about 350 µl, about 250 µl, about 150 µl, or about 50 µl. Most preferably the volume of the dose is less than or equal to about 2.5 ml.

According to a preferred embodiment the dose contains less than or equal to about 0.5 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 70 mg, about 80 mg, about 90 mg, about 100 mg, or about 110 mg of antibody. Most preferably the dose contains less than or equal to about 50 mg of antibody.

According to a preferred embodiment the dose contains an amount of antibody that is about 1 µg/kg, about 10 µg/kg, about 20 µg/kg, about 50 µg/kg, about 100 µg/kg, about 200 µg/kg, about 500 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, or about 11 mg/kg (of mass of the mammal to which the dose it to be administered).

For repeated administrations over several days or longer, depending on the condition, the treatment is sustained until a desired suppression of symptoms occurs or until sufficient therapeutic levels are achieved to reduce pain. In an embodiment a dosing regimen may comprise administering an initial dose of about 2 mg/kg, followed by a weekly maintenance dose of about 1 mg/kg of the anti-NGF antibody, or followed by a maintenance dose of about 1 mg/kg every other week. However, other dosing regimens may be useful, depending on the pattern of pharmacokinetic decay that the practitioner wishes to achieve. For example, in some embodiments, dosing from one-four times a week is contemplated. Even less frequent dosing may be used.

For the purpose of the present invention, the appropriate dosage of an anti-NGF antagonist antibody will depend on the antibody (or compositions thereof) employed, the type and severity of the pain or lower urinary tract symptom to be treated, whether the agent is administered for preventative or therapeutic purposes, previous therapy, the patient's clinical history and response to the agent, and the discretion of the attending physician. Typically the clinician will administer an anti-NGF antagonist antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of pain. Alternatively, sustained continuous release formulations of anti-NGF antagonist antibodies may be appropriate. Various formulations and devices for achieving sustained release are known in the art.

In some individuals, more than one dose may be required. Frequency of administration may be determined and adjusted over the course of therapy. For example, frequency of administration may be determined or adjusted based on the type and severity of the pain and/or lower urinary tract symptom to be treated, whether the agent is administered for preventive or therapeutic purposes, previous therapy, the patient's clinical history and response to the agent, and the discretion of the attending physician. Typically the clinician will administer an anti-NGF antagonist antibody (such as E3), until a dosage is reached that achieves the desired result. In some cases, sustained continuous release formulations of E3 antibodies may be appropriate. Various formulations and devices for achieving sustained release are known in the art.

In one embodiment, dosages for an anti-NGF antagonist antibody may be determined empirically in individuals who have been given one or more administration(s) of an NGF antagonist. Individuals are given incremental dosages of an anti-NGF antagonist antibody. To assess efficacy of an anti-NGF antagonist antibody, an indicator of pain or lower urinary tract symptoms may be followed, such as a change in a pain numerical rating scale (NRS), a change in the O'Leary-Sant Interstitial Cystitis Symptom Index (ICSI), a change in the O'Leary-Sant Interstitial Cystitis Problem Index (ICPI), a change in the Pelvic Pain and Urgency/Frequency (PUF) symptom score and/or changes in micturition variables including micturition frequency, nocturnal frequency, incontinence episode frequency, mean volume voided per micturition, mean interstitial cystitis pain severity, urinary urgency episodes, average sleep disturbance score, average pain associated with sexual activity pain score, global response assessment, patent reporting treatment impact assessment, treatment failure, biomarkers, safety endpoints and/or pharmacokinetic measures. Biomarkers may include NGF, glycoprotein-51 (GP-51), antiproliferative factor (APF) and HB-Epidermal growth factor (HB-EGF) amongst others.

Administration of an anti-NGF antagonist antibody in accordance with the method in the present invention can be continuous or intermittent, depending, for example, upon the recipient's physiological condition, whether the purpose of the administration is therapeutic or prophylactic, and other factors known to skilled practitioners. The administration of an anti-NGF antagonist antibody may be essentially continuous over a preselected period of time or may be in a series of spaced dose, e.g., either before, during, or after developing pain and/or lower urinary tract symptoms associated with interstitial cystitis and/or painful bladder syndrome and/or bladder pain syndrome; before; during; before and after; during and after; before and during; or before, during, and after developing pain and/or lower urinary tract symptoms associated with interstitial cystitis and/or painful bladder syndrome and/or bladder pain syndrome.

Therapeutic formulations of the anti-NGF antagonist antibody used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions. In some embodiments, more than one anti-NGF antagonist antibody may be present. At least one, at least two, at least three, at least four, at least five different, or more anti-NGF antagonist antibodies can be present. Generally, those anti-NGF antagonist antibodies have complementary activities that do not adversely affect each other. NGF antagonists can also be used in conjunction with other agents that serve to enhance and/or complement the effectiveness of the agents.

Pharmaceutically acceptable carriers include any and all solvents, dispersion media, coatings, antibacterial and antifungal agents, isotonic and absorption delaying agents, and the like that are physiologically compatible. Typically, the carrier is suitable for intravenous, intramuscular, subcutaneous, parenteral, spinal or epidermal administration (e.g., by injection or infusion). Depending on the route of administration, the active compound, i.e., antibody, antigen-binding portion thereof, immunoconjuage, or bispecific molecule, may be coated in a material to protect the compound from the action of acids and other natural conditions that may inactivate the compound.

Acceptable carriers, excipients, or stabilizers are nontoxic to recipients at the dosages and concentrations employed, and may comprise buffers such as phosphate, citrate, acetate and other organic acids including amino acid buffers; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polysorbate, Tween™, PLURONICS™ or polyethylene glycol (PEG).

In certain embodiments, the antibodies of the present disclosure may be present in a neutral form (including zwitter ionic forms) or as a positively or negatively-charged species. In some cases, the antibodies may be complexed with a counterion to form a pharmaceutically acceptable salt. Thus, the pharmaceutical compounds of the disclosure may include one or more pharmaceutically acceptable salts.

A "pharmaceutically acceptable salt" refers to a salt that retains the desired biological activity of the parent compound (e.g. antibody) and does not impart undesired toxicological effects (see e.g., Berge, S. M., et al. (1977) *J. Pharm. Sci.* 66:1-19). For example, the term "pharmaceutically acceptable salt" includes a complex comprising one or more antibodies and one or more counterions, where the counterions are derived from pharmaceutically acceptable inorganic and organic acids and bases.

Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

Furthermore, pharmaceutically acceptable inorganic bases include metallic ions. Metallic ions include, but are not limited to, appropriate alkali metal salts, alkaline earth metal salts and other physiological acceptable metal ions. Salts derived from inorganic bases include aluminum, ammonium, calcium, cobalt, nickel, molybdenum, vanadium, manganese, chromium, selenium, tin, copper, ferric, ferrous, lithium, magnesium, manganic salts, manganous, potassium, rubidium, sodium, and zinc, and in their usual valences.

Pharmaceutically acceptable acid addition salts of the antibodies of the present disclosure can be prepared from the following acids, including, without limitation formic, acetic, acetamidobenzoic, adipic, ascorbic, boric, propionic, benzoic, camphoric, carbonic, cyclamic, dehydrocholic, malonic, edetic, ethylsulfuric, fendizoic, metaphosphoric, succinic, glycolic, gluconic, lactic, malic, tartaric, tannic, citric, nitric, ascorbic, glucuronic, maleic, folic, fumaric, propionic, pyruvic, aspartic, glutamic, benzoic, hydrochloric, hydrobromic, hydroiodic, lysine, isocitric, trifluoroacetic, pamoic, propionic, anthranilic, mesylic, orotic, oxalic, oxalacetic, oleic, stearic, salicylic, aminosalicylic, silicate, p-hydroxybenzoic, nicotinic, phenylacetic, mandelic, embonic, sulfonic, methanesulfonic, phosphoric, phosphonic, ethanesulfonic, ethanedisulfonic, ammonium, benzenesulfonic, pantothenic, naphthalenesulfonic, toluenesulfonic, 2-hydroxyethanesulfonic, sulfanilic, sulfuric, nitric, nitrous, sulfuric acid monomethyl ester, cyclohexylaminosulfonic, β-hydroxybutyric, glycine, glycylglycine, glutamic, cacodylate, diaminohexanoic, camphorsulfonic, gluconic, thiocyanic, oxoglutaric, pyridoxal 5-phosphate, chlorophenoxyacetic, undecanoic, N-acetyl-L-aspartic, galactaric and galacturonic acids.

Pharmaceutically acceptable organic bases include trimethylamine, diethylamine, N,N'-dibenzylethylenediamine, chloroprocaine, choline, dibenzylamine, diethanolamine, ethylenediamine, meglumine (N-methylglucamine), procaine, cyclic amines, quaternary ammonium cations, arginine, betaine, caffeine, clemizole, 2-ethylaminoethanol, 2-diethylaminoethanol, 2-dimethylaminoethanol, ethanediamine, butylamine, ethanolamine, ethylenediamine, N-ethylmorpholine, N-ethylpiperidine, ethylglucamine, glucamine, glucosamine, histidine, hydrabamine, imidazole, isopropylamine, methylglucamine, morpholine, piperazine, pyridine, pyridoxine, neodymium, piperidine, polyamine resins, procaine, purines, theobromine, triethylamine, tripropylamine, triethanolamine, tromethamine, methylamine, taurine, cholate, 6-amino-2-methyl-2-heptanol, 2-amino-2-methyl-1,3-propanediol, 2-amino-2-methyl-1-propanol, aliphatic mono- and dicarboxylic acids, phenyl-substituted alkanoic acids, hydroxy alkanoic acids, aromatic acids, aliphatic and aromatic sulfonic acids, strontium, tricine, hydrazine, phenylcyclohexylamine, 2-(N-morpholino)ethanesulfonic acid, bis(2-hydroxyethyl)amino-tris(hydroxymethyl)methane, N-(2-acetamido)-2-aminoethanesulfonic acid, 1,4-piperazinediethanesulfonic acid, 3-morpholino-2-hydroxypropanesulfonic acid, 1,3-bis[tris(hydroxymethyl)methylamino]propane, 4-morpholinepropanesulfonic acid, 4-(2-hydroxyethyl)piperazine-1-ethanesulfonic acid, 2-[(2-hydroxy-1,1-bis(hydroxymethyl)ethyl)amino]ethanesulfonic acid, N,N-bis(2-hydroxyethyl)-2-aminoethanesulfonic acid, 4-(N-morpholino)butanesulfonic acid, 3-(N,N-bis[2-hydroxyethyl]amino)-2-hydroxypropanesulfonic acid, 2-hydroxy-3-[tris(hydroxymethyl)methylamino]-1-propanesulfonic acid, 4-(2-hydroxyethyl)piperazine-1-(2-hydroxypropanesulfonic acid), piperazine-1,4-bis(2-hydroxypropanesulfonic acid)dihydrate, 4-(2-hydroxyethyl)-1-piperazinepropanesulfonic acid, N,N-bis(2-hydroxyethyl)glycine, N-(2-hydroxyethyl)piperazine-N'-(4-butanesulfonic acid), N-[tris(hydroxymethyl)methyl]-3-aminopropanesulfonic acid, N-tris(Hydroxymethyl)methyl-4-aminobutanesulfonic acid, N-(1,1-dimethyl-2-hydroxyethyl)-3-amino-2-hydroxypropanesulfonic acid, 2-(cyclohexylamino)ethanesulfonic acid, 3-(cyclohexylamino)-2-hydroxy-1-propanesulfonic acid, 3-(cyclohexylamino)-1-propanesulfonic acid, N-(2-acetamido)iminodiacetic acid, 4-(cyclohexylamino)-1-butanesulfonic acid, N-[tris(hydroxymethyl)methyl]glycine, 2-amino-2-(hydroxymethyl)-1,3-propanediol, and trometamol.

Other formulations include suitable delivery forms known in the art including, but not limited to, carriers such as liposomes. See, for example, Mahato et al. (1997) Pharm. Res. 14:853-859. Liposomal preparations include, but are not limited to, cytofectins, multilamellar vesicles and unilamellar vesicles.

Liposomes containing the anti-NGF antagonist antibody are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antagonist (such as the antibody), which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The formulations to be used for in vivo administration must be sterile. This is readily accomplished by, for example, filtration through sterile filtration membranes.

Therapeutic anti-NGF antagonist antibody compositions are generally placed into a container having a sterile access port, for example, an intravenous solution bag or vial having a stopper pierceable by a hypodermic injection needle.

Therapeutic compositions can be administered with medical devices known in the art. For example, a therapeutic composition of the disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .lm, particularly 0.1 and 0.5 .lm, and have a pH in the range of 5.5 to 8.0.

The emulsion compositions can be those prepared by mixing an anti NGF antibody) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Treatment efficacy can be assessed by methods well-known in the art.

A polynucleotide encoding any of the antibodies or polypeptides of the invention (such as antibody E3) may also be used for delivery and expression of any of the antibodies or polypeptides of the invention (such as antibody E3) in a desired cell. It is apparent that an expression vector can be used to direct expression of an E3 antibody or polypeptide. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding any of the antibodies or polypeptides of the invention (such as antibody E3) can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent NO. 0 524 968. Additional approaches are described in Philip, Mol. Cell Biol. (1994) 14:2411 and in Woffendin, Proc. Natl. Acad. Sci. (1994) 91:1581.

Diagnostic Methods and Uses

The antibodies described herein may also be used in the detection, diagnosis and monitoring of pain and/or a lower urinary tract symptom associated with interstitial cystitis and/or painful bladder syndrome and/or bladder pain syndrome associated with altered or aberrant NGF expression (in some embodiments, increased or decreased NGF expression (relative to a normal sample), and/or inappropriate expression, such as presence of expression in tissue(s) and/or cell(s) that normally lack NGF expression, or absence of NGF expression in tissue(s) or cell(s) that normally possess NGF expression). In some embodiments, NGF expression is detected in a sample from an individual suspected of having pain and/or lower urinary tract symptoms associated with interstitial cystitis and/or painful bladder syndrome and/or bladder pain syndrome.

Thus, in some embodiments, the invention provides methods comprising contacting a specimen (sample) of an individual suspected of having altered or aberrant NGF expression with an antibody or polypeptide of the invention and determining whether the level of NGF differs from that of a control or comparison specimen.

In other embodiments, the invention provides methods comprises contacting a specimen (sample) of an individual and determining level of NGF expression. In some embodiments, the individual is suspected of having pain and/or a lower urinary tract symptom associated with interstitial cystitis and/or painful bladder syndrome and/or bladder pain syndrome.

For diagnostic applications, the antibody typically will be labeled with a detectable moiety including but not limited to radioisotopes, fluorescent labels, and various enzyme-substrate labels. Methods of conjugating labels to an antibody are known in the art. In other embodiments of the invention, antibodies of the invention need not be labeled, and the presence thereof can be detected using a labeled antibody which binds to the antibodies of the invention.

The antibodies of the present invention may be employed in any known assay method, such competitive binding assays, direct and indirect sandwich assays, and immunoprecipitation assays. Zola, Monoclonal Antibodies: A Manual of Techniques, pp. 147-158 (CRC Press, Inc. 1987).

The antibodies may also be used for in vivo diagnostic assays, such as in vivo imaging. Generally, the antibody is labeled with a radionuclide (such as 111In, 99Tc, 14C, 131I, 125I, or 3H) so that the cells or tissue of interest can be localized using immunoscintiography.

The antibody may also be used as staining reagent in pathology, following techniques well known in the art.

With respect to all methods described herein, reference to anti-NGF antagonist antibodies also includes compositions comprising one or more of these agents. These compositions may further comprise suitable excipients, such as pharmaceutically acceptable excipients including buffers, which are well known in the art. The present invention can be used alone or in combination with other conventional methods of treatment.

Kits Comprising Anti-NGF Antagonist Antibodies for Use in Detection and/or Therapy The invention also provides kits comprising antibodies for use in detection and/or therapy. Accordingly, in some embodiments, the kits comprise an antibody E3. In some embodiments, the kit comprises any antibody or polypeptide described herein. In other aspects, the kits may be used for any of the methods described herein, including, for example, to treat an individual with pain and/or a lower urinary tract symptom associated with interstitial cystitis and/or painful bladder syndrome and/or bladder pain syndrome. The kits of this invention are in suitable packaging, and may optionally provide additional components such as, buffers and instructions for use of the antibody in any of the methods described herein. In some embodiments, the kits include instructions for treating pain or lower urinary tract symptoms. In some embodiments, the kit comprises an anti-NGF antagonist antibody described herein and instructions for treating and/or preventing pain and/or lower urinary tract symptoms associated with interstitial cystitis and/or painful bladder syndrome and/or bladder pain syndrome in an individual. In some of the embodiments, the anti-NGF antagonist antibody is antibody E3.

In another aspect, the invention provides kits comprising a polynucleotide encoding an E3 polypeptide as described herein. In some embodiments, the kits further comprise instructions for use of the polynucleotide in any of the methods described herein.

The following examples are provided to illustrate, but not to limit, the invention. The Examples in WO2004/058184 are referred to illustrate the antibodies for use in the present invention. The entire content of WO2004/058184 is hereby incorporated by reference.

EXAMPLES

Example 1

Humanization and Affinity Maturation of Mouse Antagonist Anti-NGF Antibody 911

A. General Methods

The following general methods were used in this example.

Library Generation

Libraries were generated by PCR cassette mutagenesis with degenerate oligonucleotides as described in Kay et al. (1996), *Phage display of peptides and proteins: a laboratory manual*, San Diego, Academic Press (see, pages pg 277-291). The doping codon NNK was used to randomize one amino acid position to include 20 possible amino acids. To randomize one amino acid position to include only a subset of amino acids with specific properties, doping codons were used as described in Balint et al, (1993) *Gene* 137(1):109-18). Site directed mutagenesis was performed using recombinant PCR as described in Innis et al, (1990) PCR protocols: A guide to methods and applications (see, pp. 177-183).

Small Scale Fab Preparation

Small scale Fab expression in 96 well plates was optimized for screening Fab libraries. Starting from *E. coli* transformed with a Fab library, colonies were picked to inoculate both a master plate (agar LB+Ampicillin (50 µg/ml)+2% Glucose) and a working plate (2 ml/well, 96 well/plate containing 1.5 mL of LB+Ampicillin (50 µg/ml)+2% Glucose). Both plates were grown at 30° C. for 8-12 hours. The master plate was stored at 4° C. and the cells from the working plate were pelleted at 5000 rpm and resuspended with 1 mL of LB+Ampicillin (50 µg/ml)+1 mM IPTG to induce expression of Fabs. Cells were harvested by centrifugation after 5 h expression time at 30° C., then resuspended in 500 µL of buffer HBS-EP (100 mM HEPES buffer pH 7.4, 150 mM NaCl, 0.005% P20, 3 mM EDTA). Lysis of HBS-EP resuspended cells was attained by one cycle of freezing (−80° C.) then thawing at 37° C. Cell lysates were centrifuged at 5000 rpm for 30 min to separate cell debris from supernatants containing Fabs. The supernatants were then injected into the BIAcore plasmon resonance apparatus to obtain affinity information for each Fab. Clones expressing Fabs were rescued from the master plate to sequence the DNA and for large scale Fab production and detailed characterization as described below.

Large Scale Fab Preparation

To obtain detailed kinetic parameters, Fabs were expressed and purified from large cultures. Erlenmeyer flasks containing 200 mL of LB+Ampicillin (50 μg/ml)+2% Glucose were inoculated with 5 mL of over night culture from a selected Fab-expressing *E. coli* clone. Clones were incubated at 30° C. until an $OD_{550\ nm}$ of 1.0 was attained and then induced by replacing the media for 200 ml, of LB+Ampicillin (50 μg/ml)+1 mM IPTG. After 5 h expression time at 30° C., cells were pelleted by centrifugation, then resuspended in 10 mL PBS (pH 8). Lysis of the cells was obtained by two cycles of freeze/thaw (at −80° C. and 37° C., respectively). Supernatant of the cell lysates were loaded onto Ni-NTA superflow sepharose (Qiagen, Valencia. CA) columns equilibrated with PBS, pH 8, then washed with 5 column volumes of PBS, pH 8. Individual Fabs eluted in different fractions with PBS (pH 8)+300 mM Imidazol. Fractions containing Fabs were pooled and dialized in PBS, then quantified by ELISA prior to affinity characterization.

Full Antibody Preparation

For expression of full antibodies, heavy and light chain variable regions were cloned in 2 mammalian expression vectors (Eb.911.E3 or Eb.pur.911.3E for light chain and Db.911.3E for heavy chain; described herein) and transfected using lipofectemine into HEK 293 cells for transient expression. Antibodies were purified using protein A using standard methods.

Biacore Assay

Affinities of anti-NGF Fabs and monoclonal antibodies were determined using the BIAcore3000™ surface plasmon resonance (SPR) system (BIAcore, INC, Piscaway N.J.). CM5 chips were activated with N-ethyl-N'-(3-dimethylaminopropyl)-carbodiimide hydrochloride (EDC) and N-hydroxysuccinimide (NHS) according to the supplier's instructions. Human NGF was diluted into 10 mM sodium acetate pH 4.0 and injected over the activated chip at a concentration of 0.005 mg/mL. Using variable flow time across the individual chip channels, two ranges of antigen density were achieved: 100-200 response units (RU) for detailed kinetic studies and 500-600 RU for screening assays. The chip was blocked with ethanolamine. Regeneration studies showed that a mixture of Pierce elution buffer (Product No. 21004, Pierce Biotechnology, Rockford, Ill.) and 4 M NaCl (2:1) effectively removed the bound Fab while keeping the activity of hNGF on the chip for over 200 injections. HBS-EP buffer (0.01M HEPES, pH 7.4, 0.15 NaCl, 3 mM EDTA, 0.005% Surfactant P29) was used as running buffer for all the BIAcore assays.

Screening Assay

A screening BIAcore assay was optimized to determine the affinity of Fab clones from libraries. Supernatants of small culture lysates were injected at 50 μl/min for 2 min. Dissociation times of 10 to 15 minutes were used for determination of a single exponential dissociation rate ($k_{off}$) using BIAevaluation software. Samples that showed $k_{off}$ rates in the same range as the template used to create the library (clone 8L2-6D5, $k_{off}$ $1\times10^{-3}$ $s^{-1}$) were injected for confirmation and dissociation times of up to 45 min were allowed to obtain better $k_{off}$ values. Clones showing improved (slower) $k_{off}$ values were expressed at large scale and full kinetic parameters, $k_{on}$ and $k_{off}$ were determined on purified protein. The assay was capable of detecting differences in affinity that were approximately 2-fold or larger.

Affinity Determination Assay

Serial dilutions (0.1-10× estimated $K_D$) of purified Fab samples were injected for 1 min at 100 μL/min and dissociation times of up to 2 h were allowed. The concentrations of the Fab proteins were determined by ELISA and/or SDS-PAGE electrophoresis using as a standard a Fab of known concentration (as determined by amino acid analysis). Kinetic association rates ($k_{on}$) and dissociation rates ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values were calculated as $k_{off}/k_{on}$.

B. Humanization and Affinity Maturation of Mouse Antagonist Anti-NGF Antibody 911

The mouse antagonist anti-NGF antibody, 911 (see Hongo et al, (2000) Hybridoma 19(3):215-227) was selected for humanization and affinity maturation. Mab 911 binds human and rat NGF with high affinity and exhibits no significant cross-reactivity with the neurotrophins NT3, NT4/5 or BDNF. See Hongo, id. The affinity of the papain-cleaved Fab fragment of mouse Mab 911 was determined using BIAcore analysis as described above. The papain-cleaved Fab fragment of mouse Mab 911 bound human NGF with a $K_D$ of approximately 10 nM.

Humanization and affinity maturation was conducted in several steps, as follows:

(1) Preparation of CDR-Grafted Template.

The light chain extended CDRs of antibody 911 (i.e., including both the Kabat and Chothia CDR regions) were grafted into the human germline acceptor sequences O8 with JK2 and the heavy chain extended CDRs of antibody 911 were grafted in to human germline acceptor sequence VH4-59 with JH4. The amino acid sequences of the human germline acceptor sequences are shown in FIGS. 1A and 1B of WO2004/058184. Amino acid numbering is sequential. Using the protein frameworks noted above, DNA sequences were designed for synthetic genes encoding human framework with the murine CDRs. These humanized heavy and light variable domains were termed hVH and hVL respectively. Codons were optimized for *E. coli* and hamster usage. Several overlapping oligonucleotides (69-90 bases in length) extending the full length of the hVL and hVH with two short flanking primers for each chain were used to separately synthesize the two genes by recursive PCR essentially as described in Prodromou et al, (1992) *Protein Eng* 5(8): 827-9. Resulting DNA fragments of the correct length were gel purified and then cloned into an *E. coli* bicistronic expression plasmid (ampicillin resistant). Expression of the antibodies was under control of an IPTG inducible lacZ promoter similar to that described in Barbas (2001) Phage display: a laboratory manual, Cold Spring Harbor, N.Y., Cold Spring Harbor Laboratory Press (see Vector pComb3X, at pg 2.10), however, modifications included addition and expression of the following additional domains: the human Kappa light chain constant domain (see GenBank Accession No. CAA09181) and the CHI constant domain of IgG2a human immunoglobulin (GenBank Accession No. P01859).

The amino acid sequences of the variable regions of the CDR-grafted antibody (also termed the "template"), termed 8L2-4D5, are also shown in FIGS. 1A and 1B of WO2004/058184. The affinity of 8L2-4D5 was determined using BIAcore analysis as described above. 8L2-4D5 bound human NGF with a $K_D$ of approximately 38 nM.

(2) Introduction of a Point Mutation into the Framework Sequence.

The V71K substitution was introduced into the CDR-grafted heavy chain using recombinant PCR site directed mutagenesis as described in Innis et al, (1995) *PCR strategies*, San Diego, Academic Press. This substitution replaced the human framework residue with the corresponding mouse framework residue. The resulting antibody was termed 8L2-

6D5, and the amino acid sequence of the heavy chain variable region of 8L2-6D5 is shown in FIG. 1A of WO2004/058184. The affinity of 8L2-6D5 was determined using BIAcore analysis as described above. The Fab fragment of 8L2-6D5 bound human NGF with a Kd of approximately 15 nM. 8L2-6D5 was chosen as template for affinity maturation.

(3) Humanization and Affinity Maturation of CDRs L1, L2, H1 and H2.

CDRs L1, L2, H1 and H2 were subjected to humanization and affinity maturation. Amino acid positions in CDRs L1, L2, H1, and H2 were identified that are not essential for the structure of the CDRs based on the Chothia canonical structure (see Al-Lazikani et al (1997) *J. Mol. Biol.* 273(4):927-48); and subjected to randomization as follows. Two libraries were prepared containing the light chain mutations or heavy chain mutations shown in Table 2, and the grafted (mouse) CDR L3 or CDR H3, respectively, using PCR cassette mutagenesis with degenerate oligonucleotides as described in Kay et al. (1996), *Phage display of peptides and proteins: a laboratory manual*, San Diego, Academic Press, using doping codons as described in Balint et al, (1993) *Gene* 137(1): 109-18). Generally, the amino acid residues were altered to residues that are more common in human antibodies, based on alignments of antibody 911 light chain and heavy chain amino acid sequences with human germline antibody sequences. The wildtype (unsubstituted) amino acid residue was also represented in the library with the exception of CDR H2 residue 50, a methionine, in which the wildtype methionine was not represented in the library. Methionine residues are subject to oxidation; thus, replacement of that residue was expected to improve stability of the resulting antibody. The libraries of Fabs were cloned into vector pComb3X plus the human CH1 and CK regions, as described above.

TABLE 2

1. Heavy chain H1/H2 library:
CDR-H1

I34 was changed to F, L, V, S, P, T, A, or I
N35 was changed to N, T, S, or Y
CDR-H2

M50 was changed to all 20 natural amino acids
A62 was changed to A or S
L63 was changed to L or V
2. Light chain L1/L2 library
CDR-L1

S26 was changed to S, A, V, or F
D28 was changed to D, A, S, or Y
H32 was changed to H, N, K, D, E, Q, or Y
CDR-L2

Y50 was changed to Y, D, A, or S
I51 was changed to I, T, A, or V
F54 was changed to F or L
S56 was changed to S and T For affinity screening experiments, each library was further paired with the corresponding CDR-grafted light or heavy chain (for example, the H1/H2 library was paired with CDR-grafted light chain), the antibody was expressed, and affinity to human NGF of the individual clones was screened using the BIACORE surface plasmon resonance (SPR) system (BIAcore, Inc. Piscataway, N.J.) according to the manufacturer's instructions and as described above. $k_{off}$, $k_{on}$ and $K_D$ were determined. Antibody clones were ranked based on $k_{off}$ rates, since generally most variation in affinity is seen in $k_{off}$ rates, and further because $k_{off}$ rates are independent of antibody concentration.

The sequence of clones that bound was determined and the sequence of clones that bound is shown in table 3.

TABLE 3

L1 and L2 amino acid sequences, H1 and H2 amino acid sequences, and kinetic data for clones that bound following affinity screening of H1/H2 or L1/L2 library clones.

CDR 1-2
mutants
kinetic data

| Light chain library clones Paired with 8L2 heavy chain | CDRL1 AA sequence | CDRL2 AA sequence | $k_{off}$ (s-1) | *$K_D$ (nM) |
|---|---|---|---|---|
| 8L2-6D5 (control) | RASQDISNHLN (SEQ ID NO: 12) | YISRFHS (SEQ ID NO: 13) | **1e-3 | 25 |
| L129 | RASQSISNNLN (SEQ ID NO: 18) | YTSRFHS (SEQ ID NO: 19) | 4.5e-4 | 11 |
| L208 | RASQYISNHLN (SEQ ID NO: 20) | YTSRFHS (SEQ ID NO: 21) | 4.6e-4 | 11 |
| L97 | RASQSISNQLN (SEQ ID NO: 22) | YVSRFHS (SEQ ID NO: 23) | 5.6e-4 | 14 |
| L81 | RAFQAISNQLN (SEQ ID NO: 24) | YISRFHT (SEQ ID NO: 25) | 7.4e-4 | 18 |

TABLE 3-continued

L1 and L2 amino acid sequences, H1 and H2 amino acid sequences, and kinetic data for clones that bound following affinity screening of H1/H2 or L1/L2 library clones.

CDR 1-2 mutants kinetic data

| | | | | |
|---|---|---|---|---|
| L6 | RAFQSISNQLN (SEQ ID NO: 26) | YASRFHS (SEQ ID NO: 27) | 8.2e-4 | 20 |

| Heavy chain library clones Paired with 6D5 Light chain | CDRH1 AA sequence | CDRH2 AA sequence | $k_{off}$ (s-1) | *$K_D$ (nM) |
|---|---|---|---|---|
| 8L2-6D5 (control) | GFSLIGYDIN (SEQ ID NO: 9) | MIWGDGTTDYNSAL (SEQ ID NO: 10) | 1e-3 | 25 |
| H109 | GFSLIGYDSN (SEQ ID NO: 28) | IIWGDGTTDYNSAL (SEQ ID NO: 29) | 1.6e-4 | 4 |
| H19 | GFSLIGYDLN (SEQ ID NO: 30) | IIWGDGTTDYNSAV (SEQ ID NO: 31) | 2.4e-4 | 6 |
| H222 | GFSLIGYDVT (SEQ ID NO: 32) | GIWGDGTTDYNSAV (SEQ ID NO: 33) | 3.8e-4 | 9.5 |
| H225 | GFSLIGYDVT (SEQ ID NO: 34) | GIWGDGTTDYNSSV (SEQ ID NO: 35) | 3.8e-4 | 9.5 |
| H18 | GFSLIGYDAT (SEQ ID NO: 36) | GIWGDGTTDYNSAV (SEQ ID NO: 37) | 4.2e-4 | 10.5 |
| H9 | GFSLIGYDVS (SEQ ID NO: 38) | IIWGDGTTDYNSSV (SEQ ID NO: 39) | 4.1e-4 | 10.2 |
| H227 | GFSLIGYDIS (SEQ ID NO: 40) | QIWGDGTTDYNSSV (SEQ ID NO: 41) | 5.4e-4 | 13.5 |
| H17 | GFSLIGYDAS (SEQ ID NO: 42) | GIWGDGTTDYNSSV (SEQ ID NO: 43) | 6.1e-4 | 15.2 |
| H28 | GFSLIGYDST (SEQ ID NO: 44) | SIWGDGTTDYNSAL (SEQ ID NO: 45) | 7.5e-4 | 18.7 |

AA in bold were randomized as indicated above
*KD calculated using $k_{on}$ 4e4 $M^{-1}s^{-1}$
**For convenience, "e" as used herein denotes "x10." Thus, 4e4 interchangeably means $4 \times 10^4$.

CDRs containing the following substitutions retained binding:
CDR-H1
  I34: S, L, V, I and A bound.
  N35: N, T and S bound.
CDR-H2
  M50: M, I, G, Q, S, L bound.
  A62: A and S bound.
  L63: L and V bound.
CDR-L1
  S26: S, and F bound.
  D28: D, S, A, Y bound.
  H32: H, N, Q bound.
CDR-L2
  Y50: Y bound.
  I51: I, T, V, A, bound.
  F54: F bound
  S56: S and T bound CDRs containing the following substitutions were selected generally based on binding affinity and combined into a single clone, termed H19-L129:
  CDR-H1: I34L; N35N (no change)
  CDR-H2: M50I; A62A (no change); L63V
  CDR-L1: S26S (no change); D28S; H32N
  CDR-L2: Y50Y (no change); I51 T; F54F (no change); S56S (no change)

These mutations were combined (by amplifying the H and L chains by PCR, cutting the PCR products and vector (pRN8) with restriction enzyme and performing a 3 fragment ligation) into a single clone, termed H19-L129, which also included the grafted H3 and L3 CDRs. The sequence of the heavy chain and light chain variable regions of H19-L129 is shown in FIGS. 1A and 1B of WO2004/058184, and Table 4 shows the amino acid sequence of CDRs L1, L2, H1 and H2. H19-L129 bound NGF with a KD of approximately 1 nM, as determined using BIAcore analysis as described herein.

TABLE 4

Amino acid sequence of CDRs H1, H2, L1 and L2 and kinetic data for combined clone H19-L129.

| Combination clone: mutations in CDRs H1, H2, L1, L2 | CDRL1 CDRH1 AA sequence | CDRL2 CDRH2 AA sequence | $k_{off}$ (s-1) | *$K_D$ (nM) |
|---|---|---|---|---|
| H19-L129 | CDR-L1: RASQSISNNLN (SEQ ID NO: 18) | CDRL2: YTSRFHS (SEQ ID NO: 19) | 1.1e-4 | 3.5 |
| | CDR H1: GFSLIGYDLN (SEQ ID NO: 30) | CDR-H2: IIWGDGTTDYNSAV (SEQ ID NO: 31) | | |

*KD calculated using $k_{on}$ 4e4 $M^{-1}s^{-1}$ (4) Affinity Maturation of H3 and L3 CDRs.

Affinity maturation of the H3 and L3 CDRs was carried out in two steps. First, in a process termed "library scanning mutagenesis", each amino acid residue in H3 and L3 was individually prescreened in order to identify amino acid positions at which a mutation resulted in increased binding affinity to human NGF. Based on the results of the library scanning mutagenesis (also termed "small library randomization analysis"), a subset of amino acid positions in H3 and L3 were selected for preparation of the affinity maturation library, and the affinity maturation library was screened for affinity to human NGF using BIAcore analysis as described herein. It is appreciated that these techniques can be generally applied.

(a) Library Scanning Mutagenesis

Each amino acid position in the H3 and L3 CDRs was individually pre-screened for substitutions which resulted in increased binding affinity to human NGF. The frequency of amino acid substitutions at any given position that resulted in improved binding, the same binding, worse binding or no binding provided information relating to relating to positions in the CDRs that can be changed to many different amino acid (including all 20 amino acids), and positions in the CDRs which cannot be changed or which can only be changed to a few amino acids. Amino acid substitutions resulting in increased binding affinity were also identified. Based on the results of this screening, a subset of amino acid positions in CDRs H3 and L3 were selected for preparation of an affinity maturation library.

Individual Fab libraries were prepared in which each amino acid of L3 and H3 CDRs was randomized to all 20 amino acids, one at a time, resulting in several (5 libraries for the light chain and 13 libraries for the heavy chain) small libraries, each with a complexity of 20 amino acid possibilities at each amino acid position. In all cases, the native (i.e., unchanged) amino acid was represented in the library. Libraries were prepared by PCR cassette mutagenesis with degenerate oligonucleotides as described in Kay et al. (1996), *Phage display of Peptides and Proteins: a laboratory manual*, San Diego, Academic Press, using the doping codon NNK to randomize one amino acid position to include 20 possible amino acids. The 8L2-6D5 (the CDR grafted antibody, having the framework mutation V71K) served as the template for library construction because the lower affinity of the CDR grafted antibody permitted easier detection of differences in affinity in H3 and L3 mutants during screening. Thus, each member of a library contained a CDR3 (either H3 or L3) with one amino acid substitution, and 5 grafted CDRs.

20-80 clones from each small library were screened using BIAcore analysis as described herein. Samples were simultaneously analyzed by BIAcore for binding affinity to NGF in one channel of the BIAcore chip and for presence of Fab by binding to a penta-histag antibody in another channel of the sensor chip, to detect the his tag at the C terminus of the heavy chain. Clones that expressed protein were classified as having the same affinity, worse affinity, better affinity or no binding, using koff to classify: The results of this analysis are shown in Table 5.

TABLE 5

Clones that expressed protein were classified as having the same affinity, worse affinity, better affinity or no binding, based on koff.

| | mutation | better 1e-3< | same ≥1e-3, 2e-3< | Worse ≥2e-3 | no bind | Percentage of AAs that retain binding capacity |
|---|---|---|---|---|---|---|
| Light chain | L_S91X | 13% | 40% | 20% | 26% | 50% |
| | L_K92X | | 100% | | | ~100% |
| | L_T93X | | 93% | 7% | | 93% |
| | L_L94X | | 40% | 60% | | 40% |
| | L_Y96X | | 13% | 80% | 7% | 13% |
| Heavy chain | H_G98X | | 50% | 37% | 13% | 50% |
| | H_G99X | | 46% | 54% | | 46% |
| | H Y100X | | 26% | | 73% | 26% |
| | H Y101X | 6% | | 12% | 82% | 6% |
| | H_Y102X | | 7% | 25 | 68% | 7% |
| | H_G103X | 4% | 21% | 16% | 58% | 25% |
| | H_T104X | | 20% | 30% | 50% | 20% |
| | H_S105X | 10% | 25% | 26% | 39% | 35% |
| | H_Y106X | | 75% | 25% | | 75% |
| | H_Y107X | | 8% | 46% | 46% | 8% |
| | H_F108X | | 23% | 27% | 50% | 23% |
| | H_D109X | | 29% | 46% | 25% | 29% |
| | H_Y110X | | 90% | 5% | 5% | 90% |

The sequence of all clones with improved affinity was determined, revealing the frequency and identity of amino acid substitutions that resulted in increased affinity. In addition, a few clones that retained an affinity similar to the 8I2-6D5 clone were selected from each library, in order to ascertain amino acid sequence substitutions that were permitted at a given position, even though the substitution did not necessarily increase binding affinity. The results of this analysis are summarized in Table 6.

TABLE 6

| CDR H3 mutations (8L2-6D5 template, including antibody 911 CDR-H3 amino acid sequence: GGYYYGTSYYFDY (SEQ ID NO: 11) | $k_{off}$ (s-1) 1E-3 | $K_D$* (nM) 25 |
|---|---|---|
| Y100L | 1.2E-3 | 30 |
| Y100R | 1.1E-3 | 27 |
| Y101W | 5.6E-4 | 14 |
| G103A | 1.6E-4 | 4 |
| T104S | 2.2E-3 | 55 |
| S105A | 5.1E-4 | 13 |
| S105T | 6.4E-4 | 16 |
| Y106R | 1.6E-3 | 40 |
| Y106T | 2.0E-3 | 50 |
| Y106M | 2.7E-3 | 67 |
| Y107F | 1.4E-3 | 35 |
| F108W | 1.22E-3 | 30 |
| D109N | 1.5E-3 | 37 |
| D109G | 1E-3 | 25 |
| Y110K | 1.4E-3 | 35 |
| Y110S | 1.5E-3 | 37 |
| Y110R | 1.6E-3 | 40 |
| Y110T | 1.7E-3 | 42 |
| CDR L3 mutations (8L2-6D5 template, including wildtype (unsubstituted) CDR-L3 amino acid sequence: QQSKTLPYT (SEQ ID NO:_14) | $k_{off}$ (s-1) 1E-3 | $K_D$* (nM) 25 |
| S91E | 2.5E-4 | 6 |
| Y96R | 1.7E-3 | 42 |

*KD calculated using $k_{on}$ 4e4 $M^{-1}s^{-1}$

Several mutations resulted in increased binding affinity. At least the following mutations resulted in significantly increased binding affinity as compared with the 8L2-6D5 template: (H_Y101W (CDR sequence GGYWYGTSYY-FDY (SEQ ID NO:46)); H_S105A (CDR sequence GGYYYGTAYYFDY (SEQ ID NO:47)); H_S105T (CDR sequence GGYYYGTTYYFDY (SEQ ID NO:48)); H_G103A (CDR sequence GGYYYATSYYFDY (SEQ ID NO:49); and L_S91 E (CDR sequence QQEKTLPYT (SEQ ID NO:50)).

The results of this experiment were used to guide selection of amino acid positions for generation of the affinity maturation libraries.

This experiment also provided information regarding the frequency of amino acid substitutions at any given position that resulted in improved binding, the same binding, worse binding or no binding, as shown in Table 5. This information permitted identification of amino acid positions in the CDRs that could be changed to many different amino acid (including all 20 amino acids), and positions in the CDRs which could be changed to a few amino acids or a very few amino acids (in some embodiments, no amino acids). These results also demonstrated amino acid substitutions that increased binding affinity.

(b) Affinity Maturation

Next, the results of the small library randomization analysis (above) were used to select residues for production of the H3 and L3 libraries for affinity maturation of the H3 and L3 CDRs. Residues Y101 and G103 of CDR H3 and residues S91 and K92 of CDR L3 were selected for production of the H3 and L3 libraries for affinity maturation of the H3 and L3 CDRs.

This library combined mutations in H3 and L3 at the same time in CDR-grafted clone 8L2-6D5, and separately in the background of H19-L129, and had a diversity of 80 different clones. Table 7 shows the amino acid residues selected for substitution and the amino acids that were substituted at each position.

TABLE 7

Amino acid residues in H3 and L3 selected for substitution and the amino acids that were substituted at each position

CDR-H3:

Y101 was changed to Y and W, C. (Note that C was included because use of codon TRS in one degenerated oligonucleotide also generated codon C).
G103 was changed to A, P, S

CDR-L3:

S91 was changed to E.
K92 was changed to all twenty amino acids. A, R, K, and H bound.

Each polypeptide was expressed as a Fab, and affinity to human NGF of 96 individual clones was screened for each library using BIACORE analysis according to the manufacturer's instructions and described above. The results of this analysis are shown in Table 8.

TABLE 8

| CDR L3 H3 COMBINATION mutations (8L2-6D5 template) | $k_{off}$ (s-1) 1E-3 | $K_D$* (nM) 25 |
|---|---|---|
| L_S91E; L_K92A (CDR sequence QQEATLPYT (SEQ ID NO: 51)) H_Y101W; H_G103A (CDR sequence GGYWYATSYYFDY (SEQ ID NO: 52)) | 5.5E-4 | 13 |
| L_S91E; L_K92R (CDR sequence QQERTLPYT (SEQ ID NO: 53)) H_Y101W; H_G103A (CDR sequence GGYWYATSYYFDY (SEQ ID NO: 54)) | 1.0E-4 | 25 |
| CDR L3 H3 COMBINATION mutations (H19-L129 template, H1H2L1L2 matured) | $k_{off}$ (s-1) 1.1e-4 | $K_D$* (nM) |
| L_S91E; L_K92H (CDR sequence QQEHTLPYT (SEQ ID NO: 55)) H_Y101W; H_G103A (CDR sequence GGYWYATSYYFDY (SEQ ID NO: 56)) | 1.2E-5 | 0.3 |

TABLE 8-continued (CLONE E3)

| | | |
|---|---|---|
| L_S91E; L_K92S<br>(CDR sequence QQESTLPYT (SEQ ID NO: 57))<br>H_Y101W; H_G103S<br>(CDR sequence GGYWYSTSYYFDY (SEQ ID NO: 58)) | 4.7E-5 | 1.1 |
| L_S91E; L_K92K<br>(CDR sequence QQEKTLPYT (SEQ ID NO: 59))<br>H_Y101Y; H_G103A<br>(CDR sequence GGYYYATSYYFDY (SEQ ID NO: 60)) | 2E-5 | 0.5 |
| L_S91E; L_K92R<br>(CDR sequence QQERTLPYT (SEQ ID NO: 61))<br>H_Y101W; H_G103A<br>(CDR sequence GGYWYATSYYFDY (SEQ ID NO: 62))<br>(CLONE 3C) | 1.4E-5 | 0.35 |
| L_S91E; L_K92R<br>(CDR sequence QQERTLPYT (SEQ ID NO: 63))<br>H_Y101Y; H_G103A<br>(CDR sequence GGYYYATSYYFDY (SEQ ID NO: 64)) | 1.5E-5 | 0.37 |

*KD calculated using $k_{on}$ 4e4 $M^{-1}s^{-1}$

Based on binding affinity, the best clones, E3 (interchangeably termed "3E") and 3C, were selected for further characterization. E3 comprised the following CDR substitutions: CDR-H3: Y101W, G103A; and CDR-L3: S91E, K92H, which were combined into a single clone which also included the following L1, L2, H1 and H2 mutations:
CDR-H1: I34L;
CDR-H2: M50I; L63V;
CDR-L1: D28S; H32N;
CDR-L2: I51T.

The sequence of the heavy chain and light chain variable regions of E3 is shown in SEQ ID Nos. 1 and 2 (see also FIGS. 1A and 1B of WO2004/058184). 3C comprised the following CDR substitutions: CDR-L3: S91E; K92R; CDRH3: Y101W; G103A, which were combined into a single clone which also included the L1, L2, H1 and H2 mutations described for clone 3E.

3E and 3C sequences were cloned into mammalian expression vectors for production of Fab and full antibody, and expressed in HEK293 cells and purified using Ni-NTA or protein A chromatography. Pure protein was accurately quantified by amino acid analysis.

The binding affinities to human NGF of Fabs E3 and 3C were measured using BIAcore analysis according to the manufacturer's instructions and as described above, except that 100 RU NGF was used on chip to prevent a rebinding effect. Briefly, several concentrations of antibodies (Fabs) were injected for 2 minutes onto a CM5 chip with 100 RU of immobilized human NGF on it, and permitted to dissociate for 1800 seconds. Mouse antibody 911 (Fab) was analyzed as a control. Data was analyzed using BIAevaluation software following the manufacturer's instructions. The results of the analysis of antibody E3 and 911 are shown in FIGS. 9 and 10 of WO2004/058184. E3 bound human NGF with a KD of approximately 0.07 nM (and with a kon of about 6.0e5 M-1s-1, and a $k_{off}$ of about 4.2e-5 s-1). 3C bound human NGF with a KD of approximately 0.35 nM (with a $k_{off}$ of about 1.4E-5). By contrast, mouse antibody 911 bound NGF with a KD of 3.7 nM, $k_{off}$ of $8.4×10^{-5} s^{-1}$ and $k_{on}$ of $2.2×10^4 Ms^{-1}$.

Antibody E3 (interchangeably termed 3E) was selected for further analysis based on the high binding affinity. To test the ability of E3 to prevent the interaction of NGF with the NGF receptors trkA and p75, 2.5 nM of human NGF was premixed and incubated for one hour with 0 to 50 nM of antibody E3 (Fab). After the incubation, samples were injected at 10 ul/minute on a BIAcore CM5 chip containing 260 RU of p75 (channel 2) and 600 RU of trkA (channel 3), and percent binding was determined. The results of this analysis are shown in FIG. 11 of WO2004/058184. Increased concentrations of Fab E3 blocked the interaction of NGF with both p75 and trkA, as shown by decreased signal (measured in RU), indicating that Fab E3 blocks the interaction of human NGF with both trkA and p75. When antibody E3 (Fab) concentration equaled NGF concentration (at about 2.5 nM NGF concentration), no NGF binding was observed (as shown by a signal of zero). The fact that zero percent NGF-receptor binding occurred when concentration of NGF was equal to antibody 3E concentration suggested that 2.5 nM NGF was at least ten-fold higher than the kD of E3 for NGF and at equilibrium.

Example 2

Evaluation of NGF-Blocking Ability of Anti-NGF Antibodies using Mouse E13.5 Trigeminal Neuron Survival Assay The ability of Fab E3 or full antibody E3 to block NGF activity was evaluated by measurement of the capacity of the antibody to inhibit NGF-dependent survival of mouse E13.5 trigeminal neurons in vitro. The trigeminal ganglion is comprised of cutaneous sensory neurons that innervate the facial region. The survival of mouse E13.5 trigeminal neurons is a sensitive assay to evaluate the NGF-blocking activity of anti-NGF antagonist antibodies because NGF is required to support survival of these neurons. For example, at saturating concentrations of NGF, the survival is close to 100% by 48 hours in culture. By contrast, less than 5% of the neurons survive by 48 hours in absence of NGF.

The survival assay was conducted as follows: time-mated pregnant Swiss Webster female mice were euthanised by CO2 inhalation. The uterine horns were removed and the embryos at embryonic stage E13.5 were extracted and decapitated. The trigeminal ganglia were dissected using electrolytically sharpened tungsten needles. The ganglia were then trypsinized, mechanically dissociated and plated at a density of 200-300 cells per well in defined, serum-free medium in 96-well plates coated with poly-L-ornithine and laminin.

The blocking activity of anti-NGF Fabs or antibodies was assessed by adding to the trigeminal neurons varying doses of anti-NGF antibodies Mab 911 (Fab), 8L2-6D5; H19-L129; E3 and 3C; and human or rat NGF at the following concentrations: 0.4 ng/ml (~15 pM; this concentration represented a saturating concentration of NGF for survival) and 0.04 ng/ml (~1.5 pM; this concentration is around the IC50). After 48 hours in culture, the cells were subjected to an automated immunocytochemistry protocol performed on a Biomek FX liquid handling workstation (Beckman Coulter) as follows: fixation using 4% formaldehyde, 5% sucrose, and PBS; permeabilization using 0.3% Triton X-100 in PBS); blocking of unspecific binding sites using 5% normal goat serum, 0.11% BSA in PBS; and sequential incubation with a primary and secondary antibodies to detect neurons. The primary antibody was rabbit polyclonal antibody against the protein gene product 89.5 (PGP9.5, Chemicon), an established neuronal phenotypic marker. The secondary antibody was Alexa Fluor 488 goat anti-rabbit (Molecular Probes), together with the nuclear dye Hoechst 33342 (Molecular Probes) to label the nuclei of all the cells present in the culture. Image acquisition and image analysis were performed on a Discovery-I/GenII Imager (Universal Imaging Corporation). Images were automatically acquired at two wavelengths for Alexa Fluor 488 and Hoechst 33342, with the nuclear staining being used as reference point for the image-based auto-focus system of the Imager, since nuclear staining is present in all of the wells. Appropriate objectives and number of sites imaged per well were selected to cover the entire surface of each well. Automated image analysis was set up to count the number of neurons present in each well after 48 hours in culture based on their specific staining with the anti-PGP9.5 antibody. Careful thresholding of the image and application of morphology and fluorescence intensity based selectivity filter resulted in an accurate count of neurons per well.

The results of this experiment demonstrated that Fab E3 blocked NGF activity with a high affinity. The results are shown in FIGS. 4-6 of WO2004/058184, and Table 9.

FIG. 4 of WO2004/058184 is a graph showing NGF-dependent survival of E13.5 neurons in the presence of varying concentration of human and rat NGF.

FIG. 5 of WO2004/058184 is a graph comparing the NGF blocking effect of various Fabs in the presence of either 0.04 ng/ml of human NGF (approximately 1.5 pM; shown in the lower panel) or 0.4 ng/ml human NGF (approximately 15 pM; shown in the upper panel). 1.5 pM of NGF was around the EC50 of NGF promoting survival, while 15 pM represented a saturating concentration of NGF. Survival of E13.5 mouse trigeminal neurons in various concentrations of Fab E3; murine 911 Fab; and Fab H19-L129 and Fab 8L2-6D5 was assessed as described above. The IC50 (in pM) was calculated for each Fab at each NGF concentration, and is shown in Table 9. Fab E3 strongly blocked human NGF-dependent trigeminal neuron survival, with an IC50 of approximately 21 pM in the presence of 15 pM human NGF, and an IC50 of approximately 1.2 pM in the presence of 1.5 pM human NGF. Fabs 3C and H19-L129 also strongly blocked human NGF-dependent trigeminal neuron survival. FIG. 6 is a graph comparing the NGF blocking effect of various Fabs in the presence of either 0.04 ng/ml of rat NGF (approximately 1.5 pM; shown in the lower panel) or 0.4 ng/ml rat NGF (approximately 15 pM; shown in the upper panel). 1.5 pM of NGF was around the EC50, while 15 pM represented a saturating concentration of NGF. Survival of E13.5 mouse trigeminal neurons in various concentrations of Fab E3; murine Fab 911; and Fab H19-L129 and 8L2-6D5 was assessed as described above. The EC50 (in pM) was calculated for each Fab at each NGF concentration, and is shown in Table 9. Fab E3 strongly blocked human NGF-dependent trigeminal neuron survival, with an IC50 of approximately 31.6 pM in the presence of 15 pM rat NGF, and an IC50 of approximately 1.3 pM in the presence of 1.5 pM rat NGF. Fabs 3C and H19-L129 also strongly blocked rat NGF-dependent trigeminal neuron survival.

TABLE 9

| Human NGF | IC50 (in the presence of 15 pM NGF) pM | IC50 (in the presence of 1.5 pM NGF) pM |
| --- | --- | --- |
| 8L2-6D5 Fab | 1580.5 | 461.8 |
| H19-L129 Fab | 60.1 | 9.6 |
| 3E Fab | <21.0 | <1.2 |
| 3C Fab | 80.9 | 5.6 |
| 911 Fab | 322.3 | 63.5 |

| Rat NGF | IC50 (15 pM NGF) pM | IC50 (1.5 pM NGF) pM |
| --- | --- | --- |
| 8L2-6D5 Fab | 730.3 | 169.4 |
| H19-L129 Fab | 31.0 | 6.0 |
| 3E Fab | <8.3 | <1.3 |
| 3C Fab | 31.6 | 6.0 |
| 911 Fab | 161.0 | 34.6 |

In a different experiment, we compared the ability of full antibody E3 and Fab 3E to inhibit NGF-dependent survival of E13.5 neurons in the presence of 0.4 ng/ml saturating concentration) of human NGF. The results of the analysis are shown in FIG. 10 of WO2004/058184. Full antibody E3 and Fab 3E showed similar levels of inhibition of NGF-dependent survival when the concentration of whole antibody and Fab were normalized to the number of NGF binding sites (Fab has one binding site and whole antibody has two binding sites). These results demonstrated that there was no avidity effect due to the binding of a full antibody to the NGF dimer.

In another experiments, we compared the ability of various concentrations (20, 4, 0.8, 0.16, 0.032, 0.0064, 0.00128, and 0.0 nM) of antibody E3, antibody 911, and a trkA receptor immunadhesin (consisting of the extracellular domain of the NGF receptor trkA fused with the immunoglobulin Fc domain, CH2-CH3) to inhibit NGF-dependent survival of E13.5 neurons in the presence of 0.4 ng/ml (saturating conditions). These results are shown in FIG. 11 of WO2004/058184. These results demonstrated that antibody E3 blocked NGF better than either antibody 911 or the trkA immunoadhesin.

Example 3

Evaluation of the Specificity of Anti-NGF Antibody E3 Using Mouse Trigeminal and Nodose Neuron Survival Assays The ability of antibody E3 to specifically block NGF activity was evaluated by measurement of the capacity of the antibody to inhibit survival of mouse E17/18 trigeminal neurons in vitro in the presence of saturating concentrations of NGF, the NGF-related neurotrophin NT3, or the NGF-unrelated neurotrophic factor, macrophage stimulating protein (MSP). The survival of mouse E17/18 trigeminal neurons is a sensitive assay to evaluate the NGF-blocking activity of anti-NGF antagonist antibodies because NGF is required to support survival of these neurons at higher concentrations than the level of NGF required to support survival of E13.5 TG neurons. Survival of these neurons is also supported by NT3 or MSP; therefore, the survival of these neurons is also a sensitive assay to evaluate whether the anti-NGF antagonist antibody also blocked NT3 or MSP.

The ability of antibody E3 to specifically block NGF activity was also evaluated by measurement of the capacity of the antibody to inhibit survival of mouse nodose E17 neurons in the presence of saturating concentrations of BDNF or NT4/5. Survival of nodose neurons is supported by BDNF or NT4/5; therefore, survival of these neurons is a sensitive assay to evaluate the BDNF or NT4/5-blocking ability of the anti-NGF antagonist antibody.

The survival assay was conducted as follows: time mated pregnant Swiss Webster female mice were euthanised by CO2 inhalation. The uterine horns were removed and the embryos (at embryonic day 17 or 18) were extracted and decapitated. The trigeminal and nodose ganglia were dissected and cleaned. The ganglia were then trypsinised, mechanically dissociated and plated at a density of 100-300 cells per well in defined, serum-free medium in 4-well plates (Greiner) coated with poly-L-ornithine and laminin.

E17/18 trigeminal neurons were grown either without added neurotrophic factors (negative control) or in the presence of saturating concentrations of human NGF (400 pM and 15 pM) (positive control); NT3 (400 pM); or MSP (600 pM). Duplicate cultures were set up that included varying concentrations of E3 and 911 Fabs and full antibodies. Concentration of Fab and full antibodies was indicated per binding site (e.g., a full antibody contains two binding sites, while a Fab contains one binding site).

E17 nodose neurons were grown either in the absence of added neurotrophic factors (negative control), or with saturating concentrations of BDNF (400 pM) (positive control) or NT4/5 (400 pM) or NGF unrelated growth factor ILF (interleukin inhibitory factor). High concentrations of neurotrophins were used, as the goal of this experiment was to test specificity of the antibodies. Duplicate cultures were set up that included varying again with and without the addition of antibodies E3 and 911. After 48 hours in culture the total number of neurons surviving in each well under each condition was ascertained by manual counting using a phase-contrast microscope.

The results of these experiments demonstrated that E3 and 911 antibodies completely blocked the survival promoting effects of NGF on E18 trigeminal neurons. By contrast, E3 and 911 antibodies had no effect on survival of trigeminal neurons promoted by NT3 or MSP, or survival of nodose neurons promoted by BDNF or NT4/5 or LIF. These results demonstrated that antibody E3 possessed selective specificity for NGF, as there was no detected interaction between these antibodies and other NGF related neurotrophins (NT3, NT4/5, BDNF) at concentrations 1000-fold to 10,000-fold higher than effective concentration for NGF blocking. Further, these results demonstrated that the neuronal death seen in NGF-supplemented cultures of NGF-dependent neurons on addition of antibody or Fab E3 was due to a specific interaction between these antibodies and NGF and was not due to a generalized toxic effect. Mouse anti-NGF antagonist antibody 911 was also tested, and similar results were observed. Note that due to the high concentrations of neurotrophins used, both antibody E3 and 911 are very close to their titration conditions and were expected to bind NGF at similar levels because the differences in binding affinity of these antibodies to NGF would to be less apparent under these conditions.

The results of these experiments are shown in FIGS. 12, 13, 14, and 15 of WO2004/058184. The data showed mean percent survival after 48 hours in culture (±standard error of mean, n=3 for each data point) relative to the survival seen in the positive control for each experiment (e.g., 100% survival of trigeminal neurons grown in the presence of saturating NGF concentration, and 100% survival of nodose neurons grown in the presence of saturating BDNF concentration, respectively). FIGS. 12-13 of WO2004/058184 are graphs showing that anti-NGF antagonist antibody E3 or Fab E3 did not inhibit the survival promoted by NT3, and MSP, even at antibody concentrations as high as 200 nM. By contrast, 20 nM of antibody E3 or Fab 3E and Fab 911 totally blocked NGF-elicited survival. Mouse anti-NGF antagonist antibody 911 was also tested, and similar results were observed. Specifically, FIG. 12 of WO2004/058184 is a graph showing comparison of the effect of various concentrations (20 nM, 2 nM, or 0.2 nM) of E3 Fab (termed "3E" in the figure) and mouse antibody 911 Fab on survival of E18 trigeminal neurons in the presence of no added neurotrophin (termed "control"), 400 pM NGF (termed "NGF-400 pM), 10 nM NT3 (termed "NT3-10 nM) or 600 pM MSP (termed "MSP-600 pM). FIG. 13 of WO2004/058184 is a graph depicting comparison of the effect of various concentrations (200 nM and 80 nM) of E3 Fab and full antibody and mouse antibody 911 full antibody and Fab of survival of E17 trigeminal neurons in the presence of no added neurotrophins (termed "no factor"), 400 pM NGF (termed "NGF-400 pM), 10 nM NT3 (termed "NT3-10 nM) or 600 pM MSP (termed "MSP-600 pM).

FIG. 14-15 of WO2004/058184 are graphs showing that anti-NGF antagonist antibody E3 or Fab E3 did not inhibit survival of E17 nodose neurons promoted by BDNF, NT4/5 or LIF. Mouse anti-NGF antagonist antibody 911 was also tested, and similar results were observed. Specifically, FIG. 14 of WO2004/058184 is a graph showing comparison of the effect of various concentrations (200 nM or 80 nM) of full antibody E3 (termed "3E in the figure"), Fab E3, full antibody 911, or Fab 911 on the survival of E17 nodose neurons in the presence of no added neurotrophins (termed "no factors"), 400 pM BDNF (termed "BDNF-400 pM), 400 pM NT4/5 (termed "NT4/5-400 pM), or 2.5 nM LIF (termed "LIP-2.5 nM). FIG. 15 of WO2004/058184 is a graph showing comparison of the effect of various concentrations (200 nM, 20 nM, 2 nM) of Fab E3 (termed "3E in the figure"), or Fab 911 on the survival of E17 nodose neurons in the presence of no added neurotrophins (termed "control"), 400 pM BDNF (termed "BDNF-400 pM), 400 pM NT4/5 (termed "NT4/5-400 pM), or 2.5 nM LIF (termed "LIP-2.5 nM).

Example 4

Preparation of Mammalian Expression Vectors and Expression of Antibody E3 in Mammalian Cells Three mammalian expression vectors were designed and constructed for use in the expression of antibody E3 in mammalian cells.

Vector Db.911.3E is an expression vector comprising the heavy chain variable region of the E3 antibody and the human IgG2a constant region, and is suitable for transient or stable expression of the heavy chain. Db.911.3E consists of nucleotide sequences corresponding to the following regions: the murine cytomegalovirus promoter region (nucleotides 1-612); a synthetic intron (nucleotides 619-1507); the DHFR coding region (nucleotides 707-1267); human growth hormone signal peptide (nucleotides 1525-1602); antibody 3E heavy chain variable region (nucleotides 1603-1965); human heavy chain IgG2a constant region containing the following mutations: A330P331 to S330S331 (amino acid numbering with reference to the wildtype IgG2a sequence; see Eur. J. Immunol. (1999) 29:2613-2624); SV40 late polyadenylation signal (nucleotides 2974-3217); SV40 enhancer region (nucleotides 3218-3463); phage f1 region (nucleotides 3551-4006) and beta lactamase (AmpR) coding region (nucleotides 4443-5300). Db.911.3E was deposited at the ATCC on Jan. 8, 2003, and was assigned ATCC Accession No. PTA-4895.

Vector Eb.911.3E is an expression vector comprising the light chain variable region of the E3 antibody and the human kappa chain constant region, and is suitable for transient expression of the light chain. Eb.911.3E consists of nucleotide sequences corresponding to the following regions: the murine cytomegalovirus promoter region (nucleotides 1-612); human EF-1 intron (nucleotides 619-1142); human growth hormone signal peptide (nucleotides 1173-1150);

antibody E3 light chain variable region (nucleotides 1251-1571); human kappa chain constant region (nucleotides 1572-1892); SV40 late polyadenylation signal (nucleotides 1910-2153); SV40 enhancer region (nucleotides 2154-2399); phage f1 region (nucleotides 2487-2942) and beta lactamase (AmpR) coding region (nucleotides 3379-4236). Eb.911.3E was deposited at the ATCC on Jan. 8, 2003, and was assigned ATCC Accession No. PTA-4893.

Vector Eb.pur.911.3E is an expression vector comprising the light chain variable region of the E3 antibody and the human kappa constant region, and is suitable for stable expression of the light chain. Eb.pur.911.3E consists of nucleotide sequences corresponding to the following regions: the murine cytomegalovirus promoter region (nucleotides 1-612); human EF-1 intron (nucleotides 619-1758); pac gene (puromycinR) coding region (nucleotides 739-1235); human hsp70 5'UTR region (nucleotides 1771-1973); human growth hormone signal peptide (nucleotides 1985-2062); antibody E3 light chain variable region (nucleotides 2063-2383); human kappa chain constant region (nucleotides 2384-2704); SV40 late polyadenylation signal (nucleotides 2722-2965); SV40 enhancer region (nucleotides 2966-3211); phage f1 region (nucleotides 3299-3654) and beta lactamase (AmpR) coding region (nucleotides 4191-5048). Eb.pur.911.E3 was deposited at the ATCC on Jan. 8, 2003, and was assigned ATCC Accession No. PTA-4894.

Transient cell expression was performed as follows: CHO and HEK293T cells in 150 mm dishes were transiently co-transfected with 25 ug of each plasmid (i.e., one plasmid containing the heavy chain and one plasmid containing the light chain). DNA was mixed with 100 ul lipofectamine 2000 (Invitrogen) according to the manufacturer's instructions. The DNA-lipid complexes were allowed to contact the cells in DMEM/F12 medium without serum or antibiotics for 5 hours. Following this incubation, the media was changed for expression to Opti-MEM (Invitrogen) without any additives for two days. Cell supernatants containing antibody were harvested sequentially up to four times with subsequent media replacement. Supernatants were purified by affinity chromatography using MapSelect Protein A resin (Amersham biosciences 17-5199-02). Antibody was bound to the protein A resin in 0.3M glycine, 0.6M NaCl buffer at pH 8, then eluted with 0.1 M citrate buffer at pH 3. Fractions containing antibody were immediately neutralized with 1M Tris buffer at pH 8.0, Antibody fractions were then dialyzed and concentrated in PBS.

Example 5

Clinical Study

Patients with clinical diagnosis of interstitial cystitis are treated with anti-NGF antagonist antibody E3 to confirm the safety and efficacy of anti-NGF antibody E3 in treating one or more pain and lower urinary tract symptoms associated with interstitial cystitis and/or painful bladder and/or bladder pain syndrome. The patients to be treated will have moderate to severe interstitial cystitis as defined by a Pelvic Pain and Urgency/Frequency (PUF—Parsons et al. Urology 2002; 60:573-578)) score of at least 16 and an O'Leary-Sant Interstitial Cystitis Symptom Index (ICSI—O'Leary et al. Urology 1997; 49(Suppl 5A):58-63) score of at least 8 at pre-treatment screening. Other inclusion criteria are to be met. Patients who do not meet all of the inclusion criteria or meet one or more exclusion criteria will be considered a screen failure and will not be randomized into the study.

The efficacy of a single dose of the antibody via infusion compared to a placebo in the treatment in pain and lower urinary tract symptoms associated with interstitial cystitis and/or painful bladder syndrome and/or bladder pain syndrome is evaluated. The E3 antibody is administered intravenously to the patients at a dosage of 200 μg/kg. In addition to efficacy, the magnitude of effect of treatment compared with placebo; the response of biomarkers to interstitial cystitis to treatment with the antibody; and the treatment response rate is evaluated, amongst other measurements. The biomarkers include NGF, glycoprotein-51 (GP-51), antiproliferative factor (APF) and HB-Epidermal growth factor (HB-EGF), amongst others.

The primary endpoint is analysed 6 weeks after intravenous infusion of the single dose of E3 antibody. Assessments at 2, 10 and 16 weeks post-dose are included as secondary endponts. The primary endpoint will be a change in an 11-point pain numerical rating scale (NCS). O'Leary-Sant Interstitial Cystitis Symptom Index (ICSI) score is used as a secondary endpoint. Other secondary endpoints include O'Leary-Sant Interstitial Cystitis Problem Index (ICPI—O'Leary et al. Urology 1997; 49(Suppl 5A):58-63), ICSI plus ICPI, Pelvic Pain and Urgency/Frequency (PUF), average daily pain, micturition diary variables recorded by the patient during the study period including including micturition frequency, nocturnal frequency, incontinence episode frequency, mean volume voided per micturition, mean interstitial cystitis pain severity, urinary urgency episodes, average sleep disturbance score, average pain associated with sexual activity pain score, global response assessment, patent reporting treatment impact assessment, treatment failure, biomarkers, safety endpoints and/or pharmacokinetic measures. Biomarkers may include NGF, glycoprotein-51 (GP-51), antiproliferative factor (APF) and HB-Epidermal growth factor (HB-EGF), amongst others.

The following data are derived from an interim analysis of an ongoing clinical trial utilising the above protocol to evaluate the safety and efficacy of E3 antibody in patients with interstitial cystitis/painful bladder syndrome/bladder pain syndrome (IC/PBS/BPS). Data from 24 patients was used in the interim analysis. A clear improvement (reduction) is seen in both the pain NRS and ICSI scores. The observed improvement in patients receiving E3 antibody is greater than that seen in patients receiving placebo. These data provide support for the fact that E3 antibody may be effective in the treatment of the pain and other lower urinary tract symptoms (LUTS) associated with IC/PBS/BPS. However, the final study result will need to be evaluated.

|  | E3 antibody 200 mcg/kg | Placebo |
|---|---|---|
| Change from baseline to Week 6 in average pain intensity | | |
| N | 13 | 11 |
| LS Mean* (90% CI) | −1.6 (−5.1, 1.8) | −0.9 (−4.1, 2.2) |
| Difference vs Placebo* | −0.7 (−2.3, 0.9) | |
| Change from baseline to Week 6 in ICSI total score | | |
| N | 11 | 9 |
| LS Mean*(90% CI) | −3.9 (−11.5, 3.6) | −2.0 (−8.9, 4.9) |
| Difference vs Placebo* | −1.9 (−5.6, 1.7) | |

Pain was assessed using an 11 point (0-10) numerical rating scale (NRS). This scale is validated and widely used in the assessment of treatments directed towards the relief of pain.

The Interstitial Cystitis Symptom Index (ICSI) assesses global IC symptom severity, with scores ranging from 0 to 20. This is based on 4 questions relating to pain and LUTS associated with IC/PBS/BPS. These include measurement of the severity of day and night-time urinary frequency, urinary urgency, and bladder pain over the preceding 4 weeks.

Deposit of Biological Material

The following materials have been deposited with the American Type Culture Collection, 10801 University Boulevard, Manassas, Va., USA (ATCC):

| Material | | ATCC Accession No. | Date of Deposit |
|---|---|---|---|
| Eb.911.3E | E3 light chain | PTA-4893 | Jan. 8, 2003 |
| Eb.pur.911.3E | E3 light chain | PTA-4894 | Jan. 8, 2003 |
| Db.911.3E | E3 heavy chain | PTA-4895 | Jan. 8, 2003 |

Details concerning these deposits can be found in WO2004058184, the content of which is herein incorporated by reference in its entirety.

```
Antibody sequences
Heavy chain variable region (Kabat CDRs are under-
lined; Chothia CDRs are BOLD AND ITALICIZED)
                                       (SEQ ID NO: 1)
QVQLQESGPGLVKPSETLSLTCTVSGFSLIGYDLNWIRQPPGKGLEWIG

IIWGDGTTDYNSAVKSRVTISKDTSKNQFSLKLSSVTAADTAVYYCAR

GGYWYATSYYFDYWGQGTLV

TVS

Light chain variable region (Kabat CDRs are under-
lined; Chothia CDRs are BOLD AND ITALICIZED)
                                       (SEQ ID NO: 2)
DIQMTQSPSSLSASVGDRVTITCRASQSISNNLNWYQQKPGKAPKLLIY

YTSRFHSGVPSRFSGSGSGTDFTFTISSLQPEDIATYYCQQEHTLP

YTFGQGTKLEIKRT

E3 heavy chain extended CDRs
                                       (SEQ ID NO: 3)
CDRH1: GFSLIGYDLN (SEQ ID NO: 4)
CDRH2: IIWGDGTTDYNSAVKS (SEQ ID NO: 5)
CDRH3: GGYWYATSYYFDY E3 light chain extended CDRs
                                       (SEQ ID NO: 6)
CDRL1: RASQSISNNLN (SEQ ID NO: 7)
CDRL2: YTSRFHS (SEQ ID NO: 8)
CDRL3: QQEHTLPYT Mouse monoclonal antibody 911 extended CDRs
911 heavy chain extended CDRs
                                       (SEQ ID NO: 9)
CDRH1: GFSLIGYDIN (SEQ ID NO: 10)
CDRH2: MIWGDGTTDYNSALKS (SEQ ID NO: 11)
CDRH3: GGYYYGTSYYFDY 911 light chain extended CDRs
                                       (SEQ ID NO: 12)
CDRL1: RASQDISNHLN (SEQ ID NO: 13)
CDRL2: YISRFHS (SEQ ID NO: 14)
CDRL3: QQSKTLPYT E3 heavy chain amino acid sequence (full)
                                       (SEQ ID NO: 16)
QVQLQESGPGLVKPSETLSLTCTVSGFSLIGYDLNWIRQPPGKGLEWIGI

IWGDGTTDYNSAVKSRVTISKDTSKNQFSLKLSSVTAADTAVYYCARGGY

WYATSYYFDYWGQGTLVTVSSASTKGPSVFPLAPCSRSTSESTAALGCLV

KDYFPEPVTVSWNSGALTSGVHTFPAVLQSSGLYSLSSVVTVPSSNFGTQ

TYTCNVDHKPSNTKVDKTVERKCCVECPPCPAPPVAGPSVFLFPPKPKDT

LMISRTPEVTCVVVDVSHEDPEVQFNWYVDGVEVHNAKTKPREEQFNSTF

RVVSVLTVVHQDWLNGKEYKCKVSNKGLPSSIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK 3E light chain amino acid sequence (full antibody)
                                       (SEQ ID NO: 17)
DIQMTQSPSSLSASVGDRVTITCRASQSISNNLNWYQQKPGKAPKLLIYY

TSRFHSGVPSRFSGSGSGTDFTFTISSLQPEDIATYYCQQEHTLPYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC 3E heavy chain nucleotide sequence (full antibody)
                                       (SEQ ID NO: 65)
CAGGTGCAGCTGCAGGAGTCTGGCCCAGGACTGGTGAAGCCTTCCGAGAC

CCTGTCCCTCACCTGCACTGTCTCTGGGTTCTCACTTATCGGCTATGATC

TTAACTGGATCCGACAGCCTCCAGGGAAGGGACTGGAGTGGATTGGGATT

ATCTGGGGTGATGGAACCACAGACTATAATTCAGCTGTCAAATCCCGCGT

CACCATCTCAAAAGACACCTCCAAGAACCAGTTCTCCCTGAAGCTGAGCT

CTGTGACCGCCGCGGACACGGCCGTGTATTACTGTGCGAGAGGAGGTTAT

TGGTACGCCACTAGCTACTACTTTGACTACTGGGGCCAGGGCACCCTGGT

CACCGTCTCCTCAGCCTCCACCAAGGGCCCATCTGTCTTCCCACTGGCCC

CATGCTCCCGCAGCACCTCCGAGAGCACAGCCGCCCTGGGCTGCCTGGTC

AAGGACTACTTCCCAGAACCTGTGACCGTGTCCTGGAACTCTGGCGCTCT

GACCAGCGGCGTGCACACCTTCCCAGCTGTCCTGCAGTCCTCAGGTCTCT

ACTCCCTCAGCAGCGTGGTGACCGTGCCATCCAGCAACTTCGGCACCCAG

ACCTACACCTGCAACGTAGATCACAAGCCAAGCAACACCAAGGTCGACAA

GACCGTGGAGAGAAAGTGTTGTGTGGAGTGTCCACCTTGTCCAGCCCCTC

CAGTGGCCGGACCATCCGTGTTCCTGTTCCCTCCAAAGCCAAAGGACACC

CTGATGATCTCCAGAACCCCAGAGGTGACCTGTGTGGTGGTGGACGTGTC

CCACGAGGACCCAGAGGTGCAGTTCAACTGGTATGTGGACGGAGTGGAGG
```

-continued

TGCACAACGCCAAGACCAAGCCAAGAGAGGAGCAGTTCAACTCCACCTTC

AGAGTGGTGAGCGTGCTGACCGTGGTGCACCAGGACTGGCTGAACGGAAA

GGAGTATAAGTGTAAGGTGTCCAACAAGGGACTGCCATCCAGCATCGAGA

AGACCATCTCCAAGACCAAGGGACAGCCAAGAGAGCCACAGGTGTATACC

CTGCCACCATCCAGAGAGGAGATGACCAAGAACCAGGTGTCCCTGACCTG

TCTGGTGAAGGGATTCTATCCATCCGACATCGCCGTGGAGTGGGAGTCCA

ACGGACAGCCAGAGAACAACTATAAGACCACCCCTCCAATGCTGGACTCC

GACGGATCCTTCTTCCTGTATTCCAAGCTGACCGTGGACAAGTCCAGATG

GCAGCAGGGAAACGTGTTCTCTTGTTCCGTGATGCACGAGGCCCTGCACA

ACCACTATACCCAGAAGAGCCTGTCCCTGTCTCCAGGAAAGTAA 3E heavy chain variable domain nucleotide sequence
(SEQ ID NO: 66)
CAGGTGCAGCTGCAGGAGTCTGGCCCAGGACTGGTGAAGCCTTCCGAGAC

CCTGTCCCTCACCTGCACTGTCTCTGGGTTCTCACTTATCGGCTATGATC

TTAACTGGATCCGACAGCCTCCAGGGAAGGGACTGGAGTGGATTGGGATT

ATCTGGGGTGATGGAACCACAGACTATAATTCAGCTGTCAAATCCCGCGT

CACCATCTCAAAAGACACCTCCAAGAACCAGTTCTCCCTGAAGCTGAGCT

CTGTGACCGCCGCGGACACGGCCGTGTATTACTGTGCGAGAGGAGGTTAT

TGGTACGCCACTAGCTACTACTTTGACTACTGGGGCCAGGGCACCCTGGT

CACCGTCTCCTCA 3E light chain nucleotide sequence (full antibody)
(SEQ ID NO: 67)
GATATCCAGATGACACAGTCCCCATCCTCCCTGTCTGCCTCTGTGGGTGA

CCGCGTCACCATCACCTGCCGCGCATCTCAGTCCATTAGCAATAATCTGA

ACTGGTATCAGCAGAAGCCAGGCAAAGCCCCAAAACTCCTGATCTACTAC

ACCTCACGCTTCCACTCAGGTGTCCCATCACGCTTCAGTGGCAGTGGCTC

TGGTACAGATTTCACCTTCACCATTAGCAGCCTGCAACCAGAAGATATTG

CCACTTATTACTGCCAACAGGAGCATACCCTTCCATATACCTTCGGTCAA

GGCACCAAGCTGGAGATCAAACGCACTGTGGCTGCACCATCTGTCTTCAT

CTTTCCTCCATCTGATGAGCAGTTGAAATCCGGAACTGCCTCTGTTGTGT

GCCTGCTGAATAACTTCTATCCACGCGAGGCCAAAGTACAGTGGAAGGTG

GATAACGCCCTCCAATCCGGTAACTCCCAGGAGAGTGTCACAGAGCAGGA

CAGCAAGGACAGCACCTACAGCCTCAGCAGCACCCTGACCCTGAGCAAAG

CAGACTACGAGAAACACMAAGTCTACGCCTGCGAAGTCACCCATCAGGGC

CTGAGTTCTCCAGTCACAAAGAGCTTCAACCGCGGTGAGTGCTAA 3E light chain variable domain nucleotide sequence
(SEQ ID NO: 68)
GATATCCAGATGACACAGTCCCCATCCTCCCTGTCTGCCTCTGTGGGTGA

CCGCGTCACCATCACCTGCCGCGCATCTCAGTCCATTAGCAATAATCTGA

ACTGGTATCAGCAGAAGCCAGGCAAAGCCCCAAAACTCCTGATCTACTAC

ACCTCACGCTTCCACTCAGGTGTCCCATCACGCTTCAGTGGCAGTGGCTC

TGGTACAGATTTCACCTTCACCATTAGCAGCCTGCAACCAGAAGATATTG

CCACTTATTACTGCCAACAGGAGCATACCCTTCCATATACCTTCGGTCAA

GGCACCAAGCTGGAGATCAAACGC

The above sequences and other sequences described herein are provided in the attached sequence listing.

Sequence Listing Free Text

Sequences identified by SEQ ID Nos. 1-8, 15-68, 70-72, 74-77 in the attached sequence listing have the free text "synthetic construct".

It is understood that the examples and embodiments described herein are for illustrative purposes only and that various modifications or changes in light thereof will be suggested to persons skilled in the art and are to be included within the spirit and purview of this application.

The invention claimed is:

1. A method for treating urinary urgency associated with interstitial cystitis and/or painful bladder syndrome and/or bladder pain syndrome in a subject, comprising administering an effective amount of an anti-NGF antagonist antibody, thereby reducing total O'Leary-Sant Interstitial Cystitis Symptom Index (ICSI) score.

2. A method for treating urinary urgency associated with interstitial cystitis and/or painful bladder syndrome and/or bladder pain syndrome in a subject, comprising administering an effective amount of an anti-NGF antibody to the subject which:
   (a) binds NGF with a $K_D$ of less than about 2 nM;
   (b) inhibits human NGF-dependent survival of mouse E13.5 trigeminal neurons with an IC50 of about 100 pM or less, wherein the IC50 is measured in the presence of about 15 pM human NGF; and
   (c) inhibits human NGF-dependent survival of mouse E13.5 trigeminal neurons with an IC50 of about 10 pM or less, wherein the IC50 is measured in the presence of about 1.5 pM of NGF,
thereby reducing total O'Leary-Sant Interstitial Cystitis Symptom Index (ICSI) score.

3. A method for treating urgency associated with interstitial cystitis and/or painful bladder syndrome and/or bladder pain syndrome in a subject, comprising administering an effective amount of an anti-NGF antagonist antibody comprising a heavy chain variable region comprising:
   (a) a CDR1 region shown in SEQ ID NO: 3;
   (b) a CDR2 region shown in SEQ ID NO:4; and
   (c) a CDR3 region shown in SEQ ID NO:5; and
a light chain variable region comprising:
   (a) a CDR1 region shown in SEQ ID NO: 6;
   (b) a CDR2 region shown in SEQ ID NO:7; and
   (c) a CDR3 region shown in SEQ ID NO:8,
   wherein the antibody binds specifically to NGF,
thereby reducing total O'Leary-Sant Interstitial Cystitis Symptom Index (ICSI) score.

4. The method of any one of claims 1-3, wherein the subject is a human.

5. The method of claim 1 or 2, wherein the antibody is a monoclonal antibody.

6. The method of claim 1 or 2, wherein the antibody is a humanized antibody.

7. The method of claim 1 or 2, wherein the antibody binds human NGF.

* * * * *

SEQUENCE LISTING

```
<160> NUMBER OF SEQ ID NOS: 77

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Gln Glu Ser Gly Pro Gly Leu Val Lys Pro Ser Glu
 1               5                  10                  15

Thr Leu Ser Leu Thr Cys Thr Val Ser Gly Phe Ser Leu Ile Gly Tyr
            20                  25                  30

Asp Leu Asn Trp Ile Arg Gln Pro Pro Gly Lys Gly Leu Glu Trp Ile
        35                  40                  45

Gly Ile Ile Trp Gly Asp Gly Thr Thr Asp Tyr Asn Ser Ala Val Lys
    50                  55                  60

Ser Arg Val Thr Ile Ser Lys Asp Thr Ser Lys Asn Gln Phe Ser Leu
65                  70                  75                  80
```

-continued

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser
        115                 120

<210> SEQ ID NO 2
<211> LENGTH: 109
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr
            100                 105

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Phe Ser Leu Ile Gly Tyr Asp Leu Asn
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Ile Ile Trp Gly Asp Gly Thr Thr Asp Tyr Asn Ser Ala Val Lys Ser
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Gly Gly Tyr Trp Tyr Ala Thr Ser Tyr Tyr Phe Asp Tyr
1               5                   10

```
<210> SEQ ID NO 6
<211> LENGTH: 11
<212> TYPE: PRT
<213> ORGANISM: Artificial Sequence
<220> FEATURE:
<223> OTHER INFORMATION: Synthetic Construct

<400> SEQUENCE: 6

Arg Ala Ser Gln Ser Ile Ser Asn Asn Leu Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic Construct

<400> SEQUENCE: 7

Tyr Thr Ser Arg Phe His Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Gln Gln Glu His Thr Leu Pro Tyr Thr
1               5

<210> SEQ ID NO 9
<211> LENGTH: 10
<212> TYPE: PRT
<213> ORGANISM: Mus musculus

<400> SEQUENCE: 9

Gly Phe Ser Leu Ile Gly Tyr Asp Ile Asn
1               5                   10

<210> SEQ ID NO 10
<211> LENGTH: 16
<212> TYPE: PRT
<213> ORGANISM: Mus musculus

<400> SEQUENCE: 10

Met Ile Trp Gly Asp Gly Thr Thr Asp Tyr Asn Ser Ala Leu Lys Ser
1               5                   10                  15

<210> SEQ ID NO 11
<211> LENGTH: 13
<212> TYPE: PRT
<213> ORGANISM: Mus musculus

<400> SEQUENCE: 11

Gly Gly Tyr Tyr Tyr Gly Thr Ser Tyr Tyr Phe Asp Tyr
1               5                   10

<210> SEQ ID NO 12
<211> LENGTH: 11
<212> TYPE: PRT
<213> ORGANISM: Mus musculus

<400> SEQUENCE: 12

Arg Ala Ser Gln Asp Ile Ser Asn His Leu Asn
```

<210> SEQ ID NO 13
<211> LENGTH: 7
<212> TYPE: PRT
<213> ORGANISM: Mus musculus

<400> SEQUENCE: 13

Tyr Ile Ser Arg Phe His Ser
1               5

<210> SEQ ID NO 14
<211> LENGTH: 9
<212> TYPE: PRT
<213> ORGANISM: Mus musculus

<400> SEQUENCE: 14

Gln Gln Ser Lys Thr Leu Pro Tyr Thr
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic Construct

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 447
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
                20                  25                  30

Asp Leu Asn Trp Ile Arg Gln Pro Pro Gly Lys Gly Leu Glu Trp Ile
            35                  40                  45

Gly Ile Ile Trp Gly Asp Gly Thr Thr Asp Tyr Asn Ser Ala Val Lys
        50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Trp Tyr Ala Thr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

```
Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 17
<211> LENGTH: 214
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Glu His Thr Leu Pro Tyr
                85                  90                  95

Thr Phe Gly Gln Gly Thr Lys Leu Glu Ile Lys Arg Thr Val Ala Ala
```

```
                    100                 105                 110
Pro Ser Val Phe Ile Phe Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct

<400> SEQUENCE: 18

Arg Ala Ser Gln Ser Ile Ser Asn Asn Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Tyr Thr Ser Arg Phe His Ser
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Arg Ala Ser Gln Tyr Ile Ser Asn His Leu Asn
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Synthetic Construct

<400> SEQUENCE: 21

Tyr Thr Ser Arg Phe His Ser
1               5

<210> SEQ ID NO 22
<211> LENGTH: 11
<212> TYPE: PRT
<213> ORGANISM: Artificial Sequence
```

```
<220> FEATURE:
<223> OTHER INFORMATION: Synthetic Construct

<400> SEQUENCE: 22

Arg Ala Ser Gln Ser Ile Ser Asn Gln Leu Asn
 1               5                  10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Tyr Val Ser Arg Phe His Ser
 1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Arg Ala Phe Gln Ala Ile Ser Asn Gln Leu Asn
 1               5                  10

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Tyr Ile Ser Arg Phe His Thr
 1               5

<210> SEQ ID NO 26
<211> LENGTH: 11
<212> TYPE: PRT
<213> ORGANISM: Artificial Sequence
<220> FEATURE:
<223> OTHER INFORMATION: Synthetic Construct

<400> SEQUENCE: 26

Arg Ala Phe Gln Ser Ile Ser Asn Gln Leu Asn
 1               5                  10

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27

Tyr Ala Ser Arg Phe His Ser
 1               5

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 28

Gly Phe Ser Leu Ile Gly Tyr Asp Ser Asn
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Ile Ile Trp Gly Asp Gly Thr Thr Asp Tyr Asn Ser Ala Leu
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Gly Phe Ser Leu Ile Gly Tyr Asp Leu Asn
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Ile Ile Trp Gly Asp Gly Thr Thr Asp Tyr Asn Ser Ala Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Gly Phe Ser Leu Ile Gly Tyr Asp Val Thr
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Gly Ile Trp Gly Asp Gly Thr Thr Asp Tyr Asn Ser Ala Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34
```

```
Gly Phe Ser Leu Ile Gly Tyr Asp Val Thr
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Gly Ile Trp Gly Asp Gly Thr Thr Asp Tyr Asn Ser Ser Val
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Gly Phe Ser Leu Ile Gly Tyr Asp Ala Thr
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Synthetic Construct

<400> SEQUENCE: 37

Gly Ile Trp Gly Asp Gly Thr Thr Asp Tyr Asn Ser Ala Val
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Gly Phe Ser Leu Ile Gly Tyr Asp Val Ser
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Ile Ile Trp Gly Asp Gly Thr Thr Asp Tyr Asn Ser Ser Val
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Construct

<400> SEQUENCE: 40

Gly Phe Ser Leu Ile Gly Tyr Asp Ile Ser
```

```
<210> SEQ ID NO 41
<211> LENGTH: 14
<212> TYPE: PRT
<213> ORGANISM: Artificial Sequence
<220> FEATURE:
<223> OTHER INFORMATION: Synthetic Construct

<400> SEQUENCE: 41

Gln Ile Trp Gly Asp Gly Thr Thr Asp Tyr Asn Ser Ser Val
 1               5                  10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Phe Ser Leu Ile Gly Tyr Asp Ala Ser
 1               5                  10

<210> SEQ ID NO 43
<211> LENGTH: 14
<212> TYPE: PRT
<213> ORGANISM: Artificial Sequence
<220> FEATURE:
<223> OTHER INFORMATION: Synthetic Construct

<400> SEQUENCE: 43

Gly Ile Trp Gly Asp Gly Thr Thr Asp Tyr Asn Ser Ser Val
 1               5                  10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gly Phe Ser Leu Ile Gly Tyr Asp Ser Thr
 1               5                  10

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Ser Ile Trp Gly Asp Gly Thr Thr Asp Tyr Asn Ser Ala Leu
 1               5                  10

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Gly Gly Tyr Trp Tyr Gly Thr Ser Tyr Tyr Phe Asp Tyr
 1               5                  10
```

```
<210> SEQ ID NO 47
<211> LENGTH: 13
<212> TYPE: PRT
<213> ORGANISM: Artificial Sequence
<220> FEATURE:
<223> OTHER INFORMATION: Synthetic Construct

<400> SEQUENCE: 47

Gly Gly Tyr Tyr Tyr Gly Thr Ala Tyr Tyr Phe Asp Tyr
 1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthetic Construct

<400> SEQUENCE: 48

Gly Gly Tyr Tyr Tyr Gly Thr Thr Tyr Tyr Phe Asp Tyr
 1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic Construct

<400> SEQUENCE: 49

Gly Gly Tyr Tyr Tyr Ala Thr Ser Tyr Tyr Phe Asp Tyr
 1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Gln Gln Glu Lys Thr Leu Pro Tyr Thr
 1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic Construct

<400> SEQUENCE: 51

Gln Gln Glu Ala Thr Leu Pro Tyr Thr
 1               5

<210> SEQ ID NO 52
<211> LENGTH: 13
<212> TYPE: PRT
<213> ORGANISM: Artificial Sequence
<220> FEATURE:
<223> OTHER INFORMATION: Synthetic Construct

<400> SEQUENCE: 52

Gly Gly Tyr Trp Tyr Ala Thr Ser Tyr Tyr Phe Asp Tyr
 1               5                   10

<210> SEQ ID NO 53
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

Gln Gln Glu Arg Thr Leu Pro Tyr Thr
1               5

<210> SEQ ID NO 54
<211> LENGTH: 13
<212> TYPE: PRT
<213> ORGANISM: Artificial Sequence
<220> FEATURE:
<223> OTHER INFORMATION: Synthetic Construct

<400> SEQUENCE: 54

Gly Gly Tyr Trp Tyr Ala Thr Ser Tyr Tyr Phe Asp Tyr
1               5                   10

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Glu His Thr Leu Pro Tyr Thr
1               5

<210> SEQ ID NO 56
<211> LENGTH: 13
<212> TYPE: PRT
<213> ORGANISM: Artificial Sequence
<220> FEATURE:
<223> OTHER INFORMATION: Synthetic Construct

<400> SEQUENCE: 56

Gly Gly Tyr Trp Tyr Ala Thr Ser Tyr Tyr Phe Asp Tyr
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Gln Glu Ser Thr Leu Pro Tyr Thr
1               5

<210> SEQ ID NO 58
<211> LENGTH: 13
<212> TYPE: PRT
<213> ORGANISM: Artificial Sequence
<220> FEATURE:
<223> OTHER INFORMATION: Synthetic Construct

<400> SEQUENCE: 58

Gly Gly Tyr Trp Tyr Ser Thr Ser Tyr Tyr Phe Asp Tyr
1               5                   10

<210> SEQ ID NO 59
<211> LENGTH: 9
<212> TYPE: PRT
```

<213> ORGANISM: Artificial Sequence
<220> FEATURE:
<223> OTHER INFORMATION: Synthetic Construct

<400> SEQUENCE: 59

Gln Gln Glu Lys Thr Leu Pro Tyr Thr
1               5

<210> SEQ ID NO 60
<211> LENGTH: 13
<212> TYPE: PRT
<213> ORGANISM: Artificial Sequence
<220> FEATURE:
<223> OTHER INFORMATION: Synthetic Construct

<400> SEQUENCE: 60

Gly Gly Tyr Tyr Tyr Ala Thr Ser Tyr Tyr Phe Asp Tyr
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Glu Arg Thr Leu Pro Tyr Thr
1               5

<210> SEQ ID NO 62
<211> LENGTH: 13
<212> TYPE: PRT
<213> ORGANISM: Artificial Sequence
<220> FEATURE:
<223> OTHER INFORMATION: Synthetic Construct

<400> SEQUENCE: 62

Gly Gly Tyr Trp Tyr Ala Thr Ser Tyr Tyr Phe Asp Tyr
1               5                   10

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Gln Gln Glu Arg Thr Leu Pro Tyr Thr
1               5

<210> SEQ ID NO 64
<211> LENGTH: 13
<212> TYPE: PRT
<213> ORGANISM: Artificial Sequence
<220> FEATURE:
<223> OTHER INFORMATION: Synthetic Construct

<400> SEQUENCE: 64

Gly Gly Tyr Tyr Tyr Ala Thr Ser Tyr Tyr Phe Asp Tyr
1               5                   10

<210> SEQ ID NO 65
<211> LENGTH: 1344
<212> TYPE: DNA
<213> ORGANISM: Artificial Sequence
<220> FEATURE:

<223> OTHER INFORMATION: Synthetic Construct

<400> SEQUENCE: 65

| | |
|---|---|
| caggtgcagc tgcaggagtc tggcccagga ctggtgaagc cttccgagac cctgtccctc | 60 |
| acctgcactg tctctgggtt ctcacttatc ggctatgatc ttaactggat ccgacagcct | 120 |
| ccagggaagg gactggagtg gattgggatt atctggggtg atggaaccac agactataat | 180 |
| tcagctgtca aatcccgcgt caccatctca aaagacacct ccaagaacca gttctccctg | 240 |
| aagctgagct ctgtgaccgc cgcggacacg gccgtgtatt actgtgcgag aggaggttat | 300 |
| tggtacgcca ctagctacta ctttgactac tggggccagg gcaccctggt caccgtctcc | 360 |
| tcagcctcca ccaagggccc atctgtcttc ccactggccc catgctcccg cagcacctcc | 420 |
| gagagcacag ccgccctggg ctgcctggtc aaggactact cccagaaacc tgtgaccgtg | 480 |
| tcctggaact ctggcgctct gaccagcggc gtgcacacct cccagctgt cctgcagtcc | 540 |
| tcaggtctct actccctcag cagcgtggtg accgtgccat ccagcaactt cggcacccag | 600 |
| acctacacct gcaacgtaga tcacaagcca agcaacacca aggtcgacaa gaccgtggag | 660 |
| agaaagtgtt gtgtggagtg tccaccttgt ccagccctc cagtggccgg accatccgtg | 720 |
| ttcctgttcc ctccaaagcc aaaggacacc ctgatgatct ccagaacccc agaggtgacc | 780 |
| tgtgtggtgg tggacgtgtc ccacgaggac ccagaggtgc agttcaactg gtatgtggac | 840 |
| ggagtggagg tgcacaacgc caagaccaag ccaagagagg agcagttcaa ctccaccttc | 900 |
| agagtggtga gcgtgctgac cgtggtgcac caggactggc tgaacggaaa ggagtataag | 960 |
| tgtaaggtgt ccaacaaggg actgccatcc agcatcgaga gaccatctc caagaccaag | 1020 |
| ggacagccaa gagagccaca ggtgtatacc ctgccaccat ccagagagga gatgaccaag | 1080 |
| aaccaggtgt ccctgacctg tctggtgaag ggattctatc catccgacat cgccgtggag | 1140 |
| tgggagtcca acggacagcc agagaacaac tataagacca cccctccaat gctggactcc | 1200 |
| gacggatcct tcttcctgta ttccaagctg accgtggaca gtccagatg gcagcaggga | 1260 |
| aacgtgttct cttgttccgt gatgcacgag gccctgcaca accactatac ccagaagagc | 1320 |
| ctgtccctgt ctccaggaaa gtaa | 1344 |

<210> SEQ ID NO 66
<211> LENGTH: 363
<212> TYPE: DNA
<213> ORGANISM: Artificial Sequence
<220> FEATURE:
<223> OTHER INFORMATION: Synthetic Construct

<400> SEQUENCE: 66

| | |
|---|---|
| caggtgcagc tgcaggagtc tggcccagga ctggtgaagc cttccgagac cctgtccctc | 60 |
| acctgcactg tctctgggtt ctcacttatc ggctatgatc ttaactggat ccgacagcct | 120 |
| ccagggaagg gactggagtg gattgggatt atctggggtg atggaaccac agactataat | 180 |
| tcagctgtca aatcccgcgt caccatctca aaagacacct ccaagaacca gttctccctg | 240 |
| aagctgagct ctgtgaccgc cgcggacacg gccgtgtatt actgtgcgag aggaggttat | 300 |
| tggtacgcca ctagctacta ctttgactac tggggccagg gcaccctggt caccgtctcc | 360 |
| tca | 363 |

<210> SEQ ID NO 67
<211> LENGTH: 645
<212> TYPE: DNA
<213> ORGANISM: Artificial Sequence
<220> FEATURE:

-continued

<223> OTHER INFORMATION: Synthetic Construct

<400> SEQUENCE: 67

```
gatatccaga tgacacagtc cccatcctcc ctgtctgcct ctgtgggtga ccgcgtcacc        60
atcacctgcc gcgcatctca gtccattagc aataatctga actggtatca gcagaagcca       120
ggcaaagccc caaaactcct gatctactac acctcacgct tccactcagg tgtcccatca       180
cgcttcagtg gcagtggctc tggtacagat ttcaccttca ccattagcag cctgcaacca       240
gaagatattg ccacttatta ctgccaacag gagcataccc ttccatatac cttcggtcaa       300
ggcaccaagc tggagatcaa cgcactgtg gctgcaccat ctgtcttcat ctttcctcca        360
tctgatgagc agttgaaatc cggaactgcc tctgttgtgt gcctgctgaa taacttctat       420
ccacgcgagg ccaaagtaca gtggaaggtg gataacgccc tccaatccgg taactcccag       480
gagagtgtca cagagcagga cagcaaggac agcacctaca gcctcagcag caccctgacc       540
ctgagcaaag cagactacga gaaacacmaa gtctacgcct gcgaagtcac ccatcagggc       600
ctgagttctc cagtcacaaa gagcttcaac cgcggtgagt gctaa                       645
```

<210> SEQ ID NO 68
<211> LENGTH: 324
<212> TYPE: DNA
<213> ORGANISM: Artificial Sequence
<220> FEATURE:
<223> OTHER INFORMATION: Synthetic Construct

<400> SEQUENCE: 68

```
gatatccaga tgacacagtc cccatcctcc ctgtctgcct ctgtgggtga ccgcgtcacc        60
atcacctgcc gcgcatctca gtccattagc aataatctga actggtatca gcagaagcca       120
ggcaaagccc caaaactcct gatctactac acctcacgct tccactcagg tgtcccatca       180
cgcttcagtg gcagtggctc tggtacagat ttcaccttca ccattagcag cctgcaacca       240
gaagatattg ccacttatta ctgccaacag gagcataccc ttccatatac cttcggtcaa       300
ggcaccaagc tggagatcaa acgc                                              324
```

<210> SEQ ID NO 69
<211> LENGTH: 98
<212> TYPE: PRT
<213> ORGANISM: Homo sapiens

<400> SEQUENCE: 69

```
Gln Val Gln Leu Gln Glu Ser Gly Pro Gly Leu Val Lys Pro Ser Glu
  1               5                  10                  15
Thr Leu Ser Leu Thr Cys Thr Val Ser Gly Gly Ser Ile Ser Ser Tyr
             20                  25                  30
Tyr Trp Ser Trp Ile Arg Gln Pro Pro Gly Lys Gly Leu Glu Trp Ile
         35                  40                  45
Gly Tyr Ile Tyr Tyr Ser Gly Ser Thr Asn Tyr Asn Pro Ser Leu Lys
     50                  55                  60
Ser Arg Val Thr Ile Ser Val Asp Thr Ser Lys Asn Gln Phe Ser Leu
 65                  70                  75                  80
Lys Leu Ser Ser Val Thr Ala Ala Asp Thr Ala Val Tyr Tyr Cys Ala
                 85                  90                  95
Arg Gly
```

<210> SEQ ID NO 70
<211> LENGTH: 120
<212> TYPE: PRT

<213> ORGANISM: Artificial Sequence
<220> FEATURE:
<223> OTHER INFORMATION: Synthetic Construct

<400> SEQUENCE: 70

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Ile Asn Trp Ile Arg Gln Pro Pro Gly Lys Gly Leu Glu Trp Ile
        35                  40                  45

Gly Met Ile Trp Gly Asp Gly Thr Thr Asp Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Tyr Tyr Gly Thr Ser Tyr Tyr Phe Asp Tyr Trp Gly
            100                 105                 110

Gln Gly Thr Leu Val Thr Val Ser
        115                 120

<210> SEQ ID NO 71
<211> LENGTH: 120
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

Asp Ile Asn Trp Ile Arg Gln Pro Pro Gly Lys Gly Leu Glu Trp Ile
        35                  40                  45

Gly Met Ile Trp Gly Asp Gly Thr Thr Asp Tyr Asn Ser Ala Leu Lys
    50                  55                  60

Ser Arg Val Thr Ile Ser Lys Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Tyr Tyr Tyr Gly Thr Ser Tyr Tyr Phe Asp Tyr Trp Gly
            100                 105                 110

Gln Gly Thr Leu Val Thr Val Ser
        115                 120

<210> SEQ ID NO 72
<211> LENGTH: 120
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Gly Tyr
            20                  25                  30

```
Asp Leu Asn Trp Ile Arg Gln Pro Pro Gly Lys Gly Leu Glu Trp Ile
             35                  40                  45

Gly Ile Ile Trp Gly Asp Gly Thr Thr Asp Tyr Asn Ser Ala Val Lys
 50                  55                  60

Ser Arg Val Thr Ile Ser Lys Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Tyr Tyr Gly Thr Ser Tyr Tyr Phe Asp Tyr Trp Gly
                100                 105                 110

Gln Gly Thr Leu Val Thr Val Ser
            115                 120

<210> SEQ ID NO 73
<211> LENGTH: 95
<212> TYPE: PRT
<213> ORGANISM: Homo sapiens

<400> SEQUENCE: 73

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro
                 85                  90                  95

<210> SEQ ID NO 74
<211> LENGTH: 109
<212> TYPE: PRT
<213> ORGANISM: Artificial Sequence
<220> FEATURE:
<223> OTHER INFORMATION: Synthetic Construct

<400> SEQUENCE: 74

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn His
             20                  25                  30

Leu Asn Trp Tyr Gln Gln Lys Pro Gly Lys Ala Pro Lys Leu Leu Ile
             35                  40                  45

Tyr Tyr Ile Ser Arg Phe His Ser Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Ser Lys Thr Leu Pro Tyr
                 85                  90                  95

Thr Phe Gly Gln Gly Thr Lys Leu Glu Ile Lys Arg Thr
                100                 105

<210> SEQ ID NO 75
<211> LENGTH: 109
<212> TYPE: PRT
<213> ORGANISM: Artificial Sequence
```

<220> FEATURE:
<223> OTHER INFORMATION: Synthetic Construct

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Phe His Ser Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Lys Thr Leu Pro Tyr
                85                  90                  95

Thr Phe Gly Gln Gly Thr Lys Leu Glu Ile Lys Arg Thr
            100                 105

<210> SEQ ID NO 76
<211> LENGTH: 1429
<212> TYPE: DNA
<213> ORGANISM: Artificial Sequence
<220> FEATURE:
<223> OTHER INFORMATION: Synthetic construct

<400> SEQUENCE: 76

```
atggccaccg actccagaac ctcctggctg ctgacagtgt ccctgctgtg tctgctgtgg      60
ccacaggagg ccagcgctca ggtgcagctg caggagtctg gcccaggact ggtgaagcct     120
tccgagaccc tgtccctcac ctgcactgtc tctggttct cacttatcgg ctatgatctt      180
aactggatcc gacagcctcc agggaaggga ctggagtgga ttgggattat ctggggtgat     240
ggaaccacag actataattc agctgtcaaa tcccgcgtca ccatctcaaa agacacctcc     300
aagaaccagt tctccctgaa gctgagctct gtgaccgccg cggacacggc cgtgtattac     360
tgtgcgagag gaggttattg gtacgccact agctactact ttgactactg gggccagggc     420
accctggtca ccgtctcctc agcctccacc aagggcccat ctgtcttccc actggcccca     480
tgctcccgca gcacctccga gagcacagcc gccctgggct gcctggtcaa ggactacttc     540
ccagaacctg tgaccgtgtc ctggaactct ggcgctctga ccagcggcgt gcacaccttc     600
ccagctgtcc tgcagtcctc aggtctctac tccctcagca gcgtggtgac cgtgccatcc     660
agcaacttcg gcacccagac ctacacctgc aacgtagatc acaagccaag caacaccaag     720
gtcgacaaga ccgtggagag aaagtgttgt gtggagtgtc caccttgtcc agcccctcca     780
gtggccggac catccgtgtt cctgttccct ccaaagccaa aggacaccct gatgatctcc     840
agaaccccag aggtgacctg tgtggtggtg acgtgtccc acgaggaccc agaggtgcag     900
ttcaactggt atgtggacgg agtggaggtg cacaacgcca agaccaagcc aagagaggag     960
cagttcaact ccaccttcag agtggtgagc gtgctgaccg tggtgcacca ggactggctg    1020
aacggaaagg agtataagtg taaggtgtcc aacaagggac tgccatccag catcgagaag    1080
accatctccc agaccaaggg acagccaaga gagccacagg tgtataccct gccaccatcc    1140
agagaggaga tgaccaagaa ccaggtgtcc ctgacctgtc tggtgaaggg attctatcca    1200
tccgacatcg ccgtggagtg ggagtccaac ggacagccag agaacaacta taagaccacc    1260
cctccaatgc tggactccga cggatccttc ttcctgtatt ccaagctgac cgtggacaag    1320
```

-continued

```
tccagatggc agcagggaaa cgtgttctct tgttccgtga tgcacgaggc cctgcacaac    1380
cactataccc agaagagcct gtccctgtct ccaggaaagt aattctaga               1429

<210> SEQ ID NO 77
<211> LENGTH: 729
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: 646
<223> OTHER INFORMATION: m = A or C

<400> SEQUENCE: 77
atggccaccg actccagaac ctcctggctg ctgacagtgt ccctgctgtg tctgctgtgg     60
ccacaggagg ccagcgctga tatccagatg acacagtccc catcctccct gtctgcctct    120
gtgggtgacc gcgtcaccat cacctgccgc gcatctcagt ccattagcaa taatctgaac    180
tggtatcagc agaagccagg caaagcccca aaactcctga tctactacac ctcacgcttc    240
cactcaggtg tcccatcacg cttcagtggc agtggctctg gtacagattt caccttcacc    300
attagcagcc tgcaaccaga agatattgcc acttattact gccaacagga gcatacccctt    360 ccatatacct tcggtcaagg caccaagctg gagatcaaac gcactgtggc tgcaccatct    420
gtcttcatct ttcctccatc tgatgagcag ttgaaatccg gaactgcctc tgttgtgtgc    480
ctgctgaata acttctatcc acgcgaggcc aaagtacagt ggaaggtgga taacgccctc    540
caatccggta actcccagga gagtgtcaca gagcaggaca caaggacag cacctacagc    600 ctcagcagca ccctgaccct gagcaaagca gactacgaga aacacmaagt ctacgcctgc    660
gaagtcaccc atcagggcct gagttctcca gtcacaaaga gcttcaaccg cggtgagtgc    720
taattctag                                                           729
```